United States Patent
Rudd et al.

(10) Patent No.: US 10,894,775 B2
(45) Date of Patent: Jan. 19, 2021

(54) PIPERIDINE DERIVATIVES AS LIVER X RECEPTOR BETA AGONISTS, COMPOSITIONS, AND THEIR USE

(71) Applicants: Merck Sharp & Dohme Corp., Rahway, NJ (US); Michael T. Rudd, Collegeville, PA (US); Zhaoyang Meng, Ambler, PA (US); Jenny Wai, Harleysville, PA (US); David Jonathan Bennett, Winchester, MA (US); Edward J. Brnardic, Lansdale, PA (US); Nigel J. Liverton, Harleysville, PA (US); Shawn J. Stachel, Perkasie, PA (US); Yongxin Han, Needham, MA (US); Paul Tempest, Taipei (TW); Jiuxiang Zhu, Shanghai (CN); Xuewang Xu, Shanghai (CN); Bin Zhu, Shanghai (CN); Chuanman Huang, Shanghai (CN)

(72) Inventors: Michael T. Rudd, Collegeville, PA (US); Zhaoyang Meng, Ambler, PA (US); Jenny Wai, Harleysville, PA (US); David Jonathan Bennett, Winchester, MA (US); Edward J. Brnardic, Lansdale, PA (US); Nigel J. Liverton, Harleysville, PA (US); Shawn J. Stachel, Perkasie, PA (US); Yongxin Han, Needham, MA (US); Paul Tempest, Taipei (TW); Jiuxiang Zhu, Shanghai (CN); Xuewang Xu, Shanghai (CN); Bin Zhu, Shanghai (CN); Chuanman Huang, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/341,591

(22) PCT Filed: Oct. 9, 2017

(86) PCT No.: PCT/US2017/055688
§ 371 (c)(1),
(2) Date: Apr. 12, 2019

(87) PCT Pub. No.: WO2018/071315
PCT Pub. Date: Apr. 19, 2018

(65) Prior Publication Data
US 2019/0375716 A1 Dec. 12, 2019

(30) Foreign Application Priority Data

Oct. 14, 2016 (WO) ................ PCT/CN2016/102097

(51) Int. Cl.
*C07D 221/20* (2006.01)
*C07D 211/16* (2006.01)
*C07D 211/96* (2006.01)

(52) U.S. Cl.
CPC .......... *C07D 221/20* (2013.01); *C07D 211/16* (2013.01); *C07D 211/96* (2013.01)

(58) Field of Classification Search
CPC .... C07D 221/20; C07D 211/16; C07D 211/96
(Continued)

(56) References Cited

U.S. PATENT DOCUMENTS 10,239,849 B2 * 3/2019 Rudd .................. C07D 401/04
2006/0189650 A1 8/2006 Cumming et al.
(Continued)

FOREIGN PATENT DOCUMENTS

WO 2004056773 A1 7/2004
WO 2007003962 A2 1/2007
(Continued)

OTHER PUBLICATIONS

Chemical Abstracts STN Registry Database, record for RN 1026453-41-7, entered on Jun. 8, 2008. (Year: 2008).*
(Continued)

*Primary Examiner* — Daniel R Carcanague
(74) *Attorney, Agent, or Firm* — Sylvia A. Ayler; Catherine D. Fitch

(57) ABSTRACT

In its many embodiments, the present invention provides certain piperidine compounds of the Formula (I): and pharmaceutically acceptable salts thereof, wherein X, Y, $R^1$, $R^2$, $R^3$, L, $R^4$, $L_1$, Q, and $R^5$ are as defined herein. The novel compounds of the invention, and pharmaceutically acceptable compositions comprising a compound thereof, are useful as Liver X-β receptor (LXRβ) agonists, and may be useful for treating or preventing pathologies related thereto. Such pathologies include, but are not limited to, inflammatory diseases and diseases characterized by defects in cholesterol and lipid metabolism, such as Alzheimer's disease.

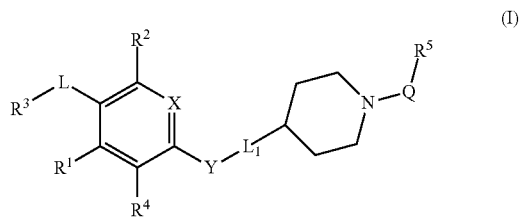

12 Claims, No Drawings

(58) Field of Classification Search
USPC .......................................................... 546/245
See application file for complete search history.

(56) References Cited

U.S. PATENT DOCUMENTS

| | | | | |
|---|---|---|---|---|
| 2008/0247964 A1* | 10/2008 | Xu | ........................ | A61P 25/08 424/45 |
| 2009/0203710 A1 | 8/2009 | Ohtake et al. | | |
| 2010/0075987 A1 | 3/2010 | Wood et al. | | |
| 2012/0172358 A1* | 7/2012 | Bradley | ............... | C07D 211/20 514/235.5 |
| 2013/0165422 A1* | 6/2013 | Bartsch | ............... | C07D 239/42 514/210.18 |
| 2018/0305332 A1* | 10/2018 | Stachel | ............... | A61K 31/451 |
| 2018/0327374 A1* | 11/2018 | Rudd | ................... | C07D 401/04 |
| 2018/0354901 A1* | 12/2018 | Rudd | ................... | C07D 211/44 |
| 2020/0039951 A1* | 2/2020 | Rudd | ................... | C07D 211/38 |

FOREIGN PATENT DOCUMENTS

| | | | | |
|---|---|---|---|---|
| WO | 2007092065 | A2 | 8/2007 | |
| WO | 2009138438 | A1 | 11/2009 | |
| WO | 2011051282 | A1 | 5/2011 | |
| WO | 2011151808 | A1 | 12/2011 | |
| WO | WO-2013062835 | A1 * | 5/2013 | ............... A61P 3/10 |
| WO | 2017083216 | A1 | 5/2017 | |
| WO | 2017083219 | A1 | 5/2017 | |
| WO | 2017095758 | A1 | 6/2017 | |
| WO | 2018071313 | A1 | 4/2018 | |
| WO | 2018071317 | A1 | 4/2018 | |

OTHER PUBLICATIONS

Chemical Abstracts STN Registry Database, record for RN 1712765-86-0, entered on May 26, 2015. (Year: 2015).*
Chemical Abstracts STN Registry Database, record for RN 1714542-07-0, entered on May 28, 2015. (Year: 2015).*
Chemical Abstracts STN Registry Database, record for RN 1715786-90-5, entered on May 29, 2015. (Year: 2015).*
Chemical Abstracts STN Registry Database, record for RN 1773460-99-3, entered on Jun. 4, 2015. (Year: 2015).*
Chemical Abstracts STN Registry Database, record for RN 1775940-40-3, entered on Jun. 8, 2015. (Year: 2015).*
Skerrett; J. Biol. Chem. 2015, 290, 21591-21602. (Year: 2015).*
Stachel; J. Med. Chem. 2016, 59, 3489-3498. (Year: 2016).*
International Search Report for PCT/CN2016/102097 dated Jul. 12, 2017, 18 pages.

* cited by examiner

PIPERIDINE DERIVATIVES AS LIVER X RECEPTOR BETA AGONISTS, COMPOSITIONS, AND THEIR USE

FIELD OF THE INVENTION

The present invention provides certain piperidine derivatives of formula (I), and compositions comprising these compounds, as Liver X receptor β (LXRβ) agonists, which may be useful for treating or preventing pathologies related thereto. Such pathologies include, but are not limited to, inflammatory diseases and diseases characterized by defects in cholesterol and lipid metabolism, such as Alzheimer's disease.

BACKGROUND OF THE INVENTION

Alzheimer's disease is a common neurodegenerative disease affecting the elderly, resulting in progressive memory impairment, loss of language and visuospatial skills, and behavior deficits. Clinical, genetic, epidemiological and biochemical evidence suggest that dysfunctional cholesterol metabolism is implicated in the pathogenesis of Alzheimer's Disease. Hypercholesterolemia and low levels of high density lipoprotein are well-established risk factors for Alzheimer's Disease. It has been suggested that vascular, genetic and amyloid factors, in combination with diet and lifestyle, contribute to the cause and progression of Alzheimer's Disease. Hooijmans et al, *Eur J Pharmacol* 585 (2008), 176-196.

The liver X receptor (LXR) is a member of the nuclear receptor family of transcription factors, and is a part of the cholesterol regulation pathway. There are two identified isoforms of LXRs. LXRα is found in liver, intestine and in macrophages, while LXRβ is widely expressed in many tissues and is considered a ubiquitous receptor. Typically, the activity of nuclear receptors is controlled by small lipophilic moieties, such as hormones, fatty acids, bile acids, cholesterol precursors and oxysterols. Lala, *Curr Opinions Invest Drugs* 2005, 6:934-943. Cholesterol precursors such as desmosterol and oxysterols are known to bind and activate LXRs.

LXRs have demonstrated a role in the physiological metabolism of lipid and cholesterol, and thus are believed to have an important role in metabolic disorders such as hyperlipidemia and atherosclerosis. Activation of LXRs reduces cholesterol absorption, thereby reducing the ability of the body to take up cholesterol. Consistently, deletion of LXRs in mice leads to impaired cholesterol and bile acid metabolism. See Peet et al, *Cell* 1998, 93(5): 693-704. Activation of LXRs also increase peripheral cholesterol efflux systems, and impact the elimination of cholesterol by regulating cholesterol excretion into bile. See Cao et al, *Drug News Perspect* 20004, 17(1), 35-41.

LXRs also regulate lipid homeostasis in the brain. The connection between metabolic disorders and Alzheimer's Disease suggests that LXRs may have a role in the Alzheimer's disease pathway. Activation of LXRs also inhibit inflammation and pro-inflammatory expression in the body. Zelcer et al, *J Clin Invest* 2006, 116:3 (607-614). Thus, LXRs may serve as targets for the treatment of inflammatory diseases. However, activation of hepatic LXRα is believed to be the underlying cause of liver steatosis and hyperlipidemia associated with dual LXRα/β small agonist molecules developed to date.

LXRs have also been proposed as possible therapeutics to treat a number of cancers e.g. prostate, breast, ovarian, melanoma, pancreas, lung, colon and hematological malignancy (Lin, C-Y and Gustafsson, J-A, (2015) Nature Reviews Cancer 15, 216-224).

LXRβ is the predominant brain isoform. See Song et al, *Ann NY Acad Sci* 195, 761:38-49. LXRβ knockout male mice demonstrated adult-onset motor neuron degeneration. (Andersson et al, *Proc Nat'l Acad Sci USA* 2005, 8; 1902 (1)):3857-3862), and the LXRα and LXRβ double knockout mice develop neurodegenerative changes in brain tissue. (Wang et al, Proc Natl Acad Sci USA. 2002, 99(21):13878-83). Therefore development of selective LXRβ agonists could be a therapeutic approach to neurodegenerative diseases such as AD and avoid the peripheral adverse lipid effects that have been linked to LXRα.

Applicants have now discovered a series of LXRβ selective agonists. Thus, the compounds of the invention, which are selective LXRβ agonists, may be useful in the treatment of Alzheimer's disease, inflammatory diseases, and diseases characterized by defects in cholesterol and lipid metabolism.

SUMMARY OF THE INVENTION

The present invention provides certain piperidine derivatives, which are collectively or individually referred to herein as "compound(s) of the invention", as described herein. The compounds of the invention are selective agonists of LXRβ, and may be useful for treating or preventing diseases or pathologies related thereto.

In one embodiment, the compounds of the invention have the structural Formula (I):

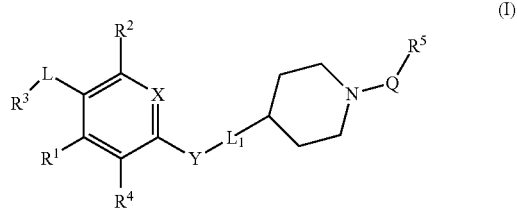

or a pharmaceutically acceptable salt thereof, wherein:
X is selected from CH and N;
Y is selected from NH, N(CH$_3$), S, S(O), S(O)$_2$ and CH$_2$;
R$^1$ is selected from H, methyl, and halogen;
R$^2$ is selected from H, halogen, cyano, cyclopropyl, —CH$_3$, and —OCH$_3$;
R$^4$ is selected from H, halogen, and methyl;
-L- is selected from —C(O)— and —S(O)$_2$—;
R$^3$ is —N(R$^{N1}$)(R$^{N2}$), wherein:
  R$^{N1}$ is selected from H and —(C$_1$-C$_6$)alkyl; and
  R$^{N2}$ is selected from H, —(C$_1$-C$_6$)alkyl, cyclopropyl, —O—(C$_1$-C$_6$)alkyl, —OH, halogen, —CN, and —(C$_1$-C$_6$)alkyl which is substituted with 1 or 2 groups independently selected from:
    —OH, halogen, —CN,
    optionally substituted phenyl, (wherein said optional substitutents on said phenyl
    are 1 to 3 groups independently selected from OH, CN, —(C$_1$-C$_4$)alkyl, —(C$_1$C$_4$)alkoxyl),
    optionally substituted heteroaryl, (wherein said optional substituents on said
    heteroaryl are 1 to 3 groups independently selected from —(C$_1$-C$_6$)alkyl, —(C$_1$C$_4$)alkoxyl, and cyclopropyl), optionally substituted cyclopropyl (wherein said optional substituents on said
cyclopropyl are 1 to 3 groups independently selected from —(C$_1$-C$_6$)alkyl), and
optionally substituted heterocycloalkyl (wherein said optional substitutents on said heterocycloalkyl are 1 to 3 groups independently selected from halogen, —OH, oxo, CN, and —(C$_1$-C$_6$)alkyl),
or, alternatively, R$^{N1}$ and R$^{N2}$ are taken together with the nitrogen atom to which they are shown attached to form a 4-, 5-, or 6-membered fully saturated heterocyclic ring comprising (including the nitrogen atom) 1, 2, or 3 ring heteroatoms selected from N, N-oxide, O, S, and S-oxide,
wherein said heterocyclic ring is unsubstituted or substituted with 1, 2, or 3 substituents independently selected from halogen, —OH, oxo, CN, —(C$_1$-C$_6$)alkyl, amino-substituted —(C$_1$-C$_6$)alkyl (wherein said amino is 1, 2, or 3 groups independently selected from —NH$_2$, —N(C$_1$-C$_4$alkyl)$_2$, and —NH(C$_1$-C$_4$alkyl)), —O—(C$_1$-C$_6$)alkyl, —(C$_1$-C$_6$)alkyl-OH, —(C$_1$-C$_6$)haloalkyl, —C(O)O—(C$_1$-C$_6$)alkyl, cyclopropyl, spirocyclopropyl, —CH$_2$—NHC(O)O—(C$_1$-C$_6$)alkyl, —CH$_2$—N(CH$_3$)C(O)O—(C$_1$-C$_6$)alkyl, phenyl, benzyl, —NHC(O)-phenyl, heteroaryl, and —(C$_1$-C$_4$)alkylheteroaryl, heterocycloalkyl;

-L$_1$- is a divalent moiety selected from:

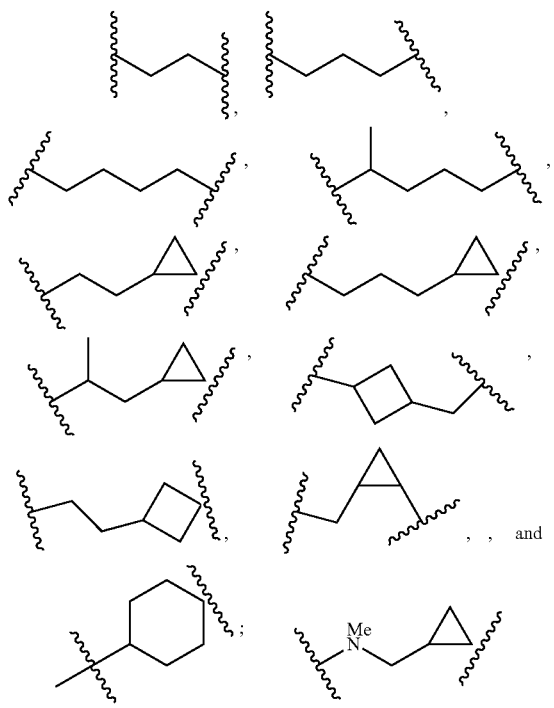
, , and ;

Q is a bond or a divalent moiety selected from —C(O)—, —S(O)$_2$—, and —C(O)O—; and
R$^5$ is —C(R$^{5A}$)(R$^{5B}$)(R$^{5C}$), wherein:
each of R$^{5A}$, R$^{5B}$ and R$^{5C}$ is independently selected from:
H, halogen, OH, NH$_2$, NHCH$_3$, —(C$_1$-C$_6$)alkyl, —(C$_1$-C$_6$)haloalkyl, —(C$_1$-C$_6$)alkenyl, —(C$_1$-C$_6$)alkynyl, —(C$_3$-C$_6$)cycloalkyl, —(C$_3$-C$_6$)cycloalkyl substituted with —(C$_1$-C$_6$)alkyl, —(C$_1$-C$_6$)alkenyl, —(C$_1$-C$_6$)alkynyl, phenyl, and phenyl substituted with from 1 to 3 groups independently selected from halogen, OH, —NH$_2$, —(C$_1$-C$_6$)alkyl, —O—(C$_1$-C$_6$)alkyl, cyclopropyl, —O—(C$_1$-C$_6$)haloalkyl, —O-cyclopropyl, and —C(O)O—(C$_1$-C$_6$)alkyl,
or R$^5$ is

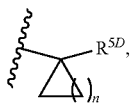

wherein n is an integer from 1 to 4;
wherein R$^{5D}$ is selected from H, —(C$_1$-C$_6$)alkyl, —(C$_1$-C$_6$)haloalkyl, phenyl, and phenyl substituted with from 1 to 3 groups independently selected from OH, halogen, —(C$_1$-C$_6$)alkyl, and —O—(C$_1$-C$_6$)alkyl,
or R$^5$ is selected from phenyl and benzyl, wherein:
said phenyl and said benzyl are unsubstituted or substituted with 1, 2, or 3 groups independently selected from halogen, CN, —(C$_1$-C$_6$)alkyl, and —(C$_1$-C$_6$)haloalkyl.

In other embodiments, the invention provides compositions, including pharmaceutical compositions, comprising one or more compounds of the invention (e.g., one compound of the invention) or a pharmaceutically acceptable salt thereof, optionally together with one or more additional therapeutic agents, optionally in an acceptable (e.g., pharmaceutically acceptable) carrier or diluent.

In another embodiment, the invention is directed to methods of treating an inflammatory disease or a disease characterized by defects in cholesterol or lipid metabolism, in a patient in need thereof by administering to the patient a compound of the invention or a pharmaceutically acceptable salt thereof. Non-limiting examples of such inflammatory diseases and diseases characterized by defects in cholesterol or lipid metabolism are described below.

In another embodiment, the invention provides for the use of a compound of the invention in the manufacture of a medicament for treating an inflammatory disease or a disease characterized by defects in cholesterol or lipid metabolism in a patient in need thereof. Non-limiting examples of such inflammatory diseases and diseases characterized by defects in cholesterol or lipid metabolism are described below.

In another embodiment, the invention is directed to a method of treating cancer in a patient in need thereof comprising administering to the patient a compound of the invention or a pharmaceutically acceptable salt thereof. Such cancers include prostate, breast, ovarian, melanoma, pancreas, lung, colon and hematological malignancy.

In another embodiment, the invention provides for the use of a compound of the invention in the manufacture of a medicament for treating cancer in a patient in need thereof comprising administering to the patient a compound of the invention or a pharmaceutically acceptable salt thereof. Such cancers include prostate, breast, ovarian, melanoma, pancreas, lung, colon and hematological malignancy.

In another embodiment, the invention provides for the use of any of the compounds of the invention for use as a medicament, or in medicine, or in therapy.

These and other embodiments of the invention, which are described in detail below or will become readily apparent to those of ordinary skill in the art, are included within the scope of the invention.

DETAILED DESCRIPTION

For each of the following embodiments, any variable not explicitly defined in the embodiment is as defined in Formula (I). In each of the embodiments described herein, each variable is selected independently of the other unless otherwise noted.

In one embodiment, the compounds of the invention have the structural Formula (I) as described above, and pharmaceutically acceptable salts thereof.

In another embodiment, in Formula (I), X is CH.

In another embodiment, in Formula (I), X is N.

The following alternative embodiments of L apply to Formula (I) and also to each of the embodiments and alternative embodiments, and all combinations of embodiments, described hereinabove.

In another embodiment, in Formula (I): L is C(O).

In another embodiment, in Formula (I): L is $SO_2$.

The following alternative embodiments of $R^3$ apply to Formula (I) and also to each of the embodiments and alternative embodiments, and all combinations of embodiments, described hereinabove.

In another embodiment, in Formula (I), $R^3$ is —N($R^{N1}$)($R^{N2}$), wherein:

$R^{N1}$ is selected from H and —($C_1$-$C_6$)alkyl; and $R^{N2}$ is selected from H, —($C_1$-$C_6$)alkyl, cyclopropyl, —O—($C_1$-$C_6$)alkyl, —OH, halogen, —CN, and —($C_1$-$C_6$)alkyl which is substituted with 1 or 2 groups independently selected from:

—OH, halogen, —CN, optionally substituted phenyl, (wherein said optional substitutents on said phenyl are 1 to 3 groups independently selected from OH, CN, —($C_1$-$C_4$)alkyl, —($C_1$-$C_4$)alkoxyl), optionally substituted heteroaryl, (wherein said optional substituents on said heteroaryl are 1 to 3 groups independently selected from —($C_1$-$C_6$)alkyl, —($C_1$-$C_4$)alkoxyl, and cyclopropyl), optionally substituted cyclopropyl (wherein said optional substituents on said cyclopropyl are 1 to 3 groups independently selected from —($C_1$-$C_6$)alkyl), and optionally substituted heterocycloalkyl (wherein said optional substitutents on said heterocycloalkyl are 1 to 3 groups independently selected from halogen, —OH, oxo, CN, and —($C_1$-$C_6$)alkyl).

In another embodiment, in Formula (I):

$R^3$ is —N($R^{N1}$)($R^{N2}$), wherein:

$R^{N1}$ is selected from H, methyl, and ethyl; and $R^{N2}$ is H, methyl, ethyl, —O-methyl, —O-ethyl, OH, fluoro, chloro, —CN, substituted methyl, or substituted ethyl, wherein each said substituent is 1 or 2 groups independently selected from:

OH, fluoro, chloro, —CN, optionally substituted phenyl, (wherein said optional substitutents on said phenyl are 1 to 3 groups independently selected from OH, CN, methyl, ethyl, —O-methyl, and —O-ethyl), optionally substituted heteroaryl, (wherein said optional substituents on said heteroaryl are 1 to 3 groups independently selected from methyl, ethyl, —O— methyl, —O-ethyl, and cyclopropyl), optionally substituted cyclopropyl (wherein said optional substituents on said cyclopropyl are 1 to 3 groups independently selected from methyl and ethyl), optionally substituted heterocycloalkyl (wherein said optional substitutents on said heterocycloalkyl are 1 to 3 groups independently selected from halogen, —OH, oxo, CN, methyl, ethyl, —O-methyl, —O-ethyl, —OH, F, Cl, and —CN).

In each of these embodiments, non-limiting examples of said heteroaryl (which is optionally substituted) include: pyridyl, pyrazinyl, furanyl, thienyl, pyrimidinyl, isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, oxindolyl, indolyl, azaindolyl, imidazolyl, thienopyridyl, imidazopyridyl, isoquinolinyl, benzoazaindolyl, and triazinyl. In one embodiment, said optionally substituted heteroaryl is isoxazolyl, oxadiazolyl, or thiazolyl.

In each of these embodiments, non-limiting examples of said optionally substituted heterocycloalkyl include: tetrahydrofuranyl and morpholinyl.

In each of these embodiments, non-limiting examples of said optionally substituted cycloalkyl include cyclopropyl, cyclobutyl, cyclopentyl and cyclohexyl.

In another embodiment, in Formula (I), $R^3$ is —N($R^{N1}$)($R^{N2}$), wherein $R^{N1}$ and $R^{N2}$ are each independently selected from H, methyl, ethyl, n-propyl, i-propyl, —$CH_2CH_2$—OH, cyclopropyl, —$CH_2$-oxadiazolyl, —$CH_2$-triazolyl (wherein said oxadiazolyl and said triazolyl are each optionally substituted with methyl or cyclopropyl). In another such embodiment, L is —C(O)—.

In another embodiment, in Formula (I), and in each of the embodiments and alternative embodiments described hereinabove, L is —C(O)—; and $R^3$ is —N($CH_3$)$_2$ or —NH($CH_3$).

In another embodiment, in Formula (I), $R^3$ is —N($R^{N1}$)($R^{N2}$), wherein:

$R^{N1}$ and $R^{N2}$ are taken together with the nitrogen atom to which they are shown attached to form a 4-, 5-, or 6-membered fully saturated heterocyclic ring comprising (including the nitrogen atom) 1, 2, or 3 ring heteroatoms selected from N, N-oxide, O, S, and S-oxide, wherein said heterocyclic ring is unsubstituted or substituted with 1, 2, or 3 substituents independently selected from halogen, —OH, oxo, CN, —($C_1$-$C_6$)alkyl, amino-substituted —($C_1$-$C_6$)alkyl (wherein said amino is 1, 2, or 3 groups independently selected from —$NH_2$, —N($C_1$-$C_4$alkyl)$_2$, and —NH($C_1$-$C_4$alkyl)), —O—($C_1$-$C_6$)alkyl, —($C_1$-$C_6$)alkyl-OH, —($C_1$-$C_6$)haloalkyl, —C(O)O—($C_1$-$C_6$)alkyl, cyclopropyl, spirocyclopropyl, —$CH_2$—NHC(O)O—($C_1$-$C_6$)alkyl, —$CH_2$—N($CH_3$)C(O)O—($C_1$-$C_6$)alkyl, phenyl, benzyl, —NHC(O)-phenyl, heteroaryl, and —($C_1$-$C_4$)alkylheteroaryl, heterocycloalkyl;

In the immediately preceding embodiment, non-limiting examples of said unsubstituted or substituted heterocyclic ring include azetidinyl, pyrrolidinyl, piperidinyl, and morpholinyl.

In an alternative of each of the preceding embodiments of $R^3$, L is —C(O)—.

The following alternative embodiments of $R^1$ apply to Formula (I) and also to each of the embodiments and alternative embodiments, and all combinations of embodiments, described hereinabove.

In another embodiment, in Formula (I), $R^1$ is selected from H, methyl, F, and Cl.

In another embodiment, in Formula (I), $R^1$ is H.

The following alternative embodiments of $R^2$ apply to Formula (I) and also to each of the embodiments and alternative embodiments, and all combinations of embodiments, described hereinabove.

In another embodiment, in Formula (I), $R^2$ is selected from H, Cl, cyano, cyclopropyl, —$CH_3$, and —$OCH_3$.

In another embodiment, in Formula (I), $R^2$ is Cl.

In another embodiment, in Formula (I), $R^2$ is cyano.

In another embodiment, in Formula (I), $R^2$ is cyclopropyl.

In another embodiment, in Formula (I), $R^2$ is $CH_3$.

In another embodiment, in Formula (I), $R^2$ is $OCH_3$.

The following alternative embodiments of $R^4$ apply to Formula (I) and also to each of the embodiments and alternative embodiments, and all combinations of embodiments, described hereinabove.

In another embodiment, in Formula (I), $R^4$ is H, —$CH_3$, or chloro.

The following alternative embodiments of Y apply to Formula (I) and also to each of the embodiments and alternative embodiments, and all combinations of embodiments, described hereinabove.

In another embodiment, in Formula (I), Y is selected from NH and $N(CH_3)$.

In another embodiment, in Formula (I), Y is S.

In another embodiment, in Formula (I), Y is S(O).

In another embodiment, in Formula (I), Y is —$S(O)_2$—.

In another embodiment, in Formula (I), Y is $CH_2$.

The following alternative embodiments of $R^5$ apply to Formula (I) and also to each of the embodiments and alternative embodiments, and all combinations of embodiments, described hereinabove.

In one embodiment, in Formula (I):

$R^5$ is —$C(R^{5A})(R^{5B})(R^{5C})$, wherein each of $R^{5A}$, $R^{5B}$ and $R^{5C}$ is independently selected from H, F, Cl, OH, $NH_2$, $NHCH_3$, —$(C_1$-$C_6)$alkyl, —$(C_1$-$C_6)$haloalkyl, —$(C_1$-$C_6)$alkenyl, —$(C_1$-$C_6)$alkynyl, —$(C_3$-$C_6)$cycloalkyl, —$(C_3$-$C_6)$cycloalkyl substituted with —$(C_1$-$C_6)$alkyl, —$(C_1$-$C_6)$alkenyl, —$(C_1$-$C_6)$alkynyl, phenyl, phenyl substituted with from 1 to 3 groups independently selected from F, Cl, —$(C_1$-$C_6)$alkyl, —O—$(C_1$-$C_6)$alkyl, and —C(O)O—$(C_1$-$C_6)$alkyl.

In an alternative of the immediately preceding embodiment, $R^{5A}$ is OH;

$R^{5B}$ is —$(C_1$-$C_3)$fluoroalkyl; and $R^{5C}$ is selected from $NH_2$, $NHCH_3$, —$(C_1$-$C_6)$alkyl, —$(C_1$-$C_4)$fluoroalkyl, phenyl, (wherein said phenyl is substituted with from 1-3 groups independently selected from halogen —$(C_1$-$C_6)$alkyl, and —$(C_1$-$C_6)$alkoxy), cyclopropyl (wherein said cyclopropyl is optionally substituted with —$(C_1$-$C_6)$alkyl, cyclobutyl (wherein said cyclobutyl is optionally substituted with —$(C_1$-$C_6)$alkyl, ethenyl, and ethynyl).

In another embodiment, in Formula (I), $R^5$ is

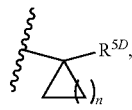

wherein n is an integer from 1 to 4; and $R^{5D}$ is as defined in Formula (I).

In another embodiment, in Formula (I), $R^5$ is selected from phenyl and benzyl, wherein said phenyl and said benzyl are unsubstituted or substituted with 1, 2, or 3 groups independently selected from halogen, CN, —$(C_1$-$C_6)$alkyl, and —$(C_1$-$C_6)$haloalkyl.

The following alternative embodiments of Q apply to Formula (I) and also to each of the embodiments and alternative embodiments, and all combinations of embodiments, described hereinabove.

In another embodiment, Q is a bond. In another embodiment, Q is —C(O)—. In another embodiment, Q is —$S(O)_2$—. In another embodiment, Q is —C(O)O—.

Specific non-limiting embodiments of compounds of the invention are shown in the examples and claims below. All valences not shown explicitly filled in the pictured example compounds of the invention are assumed to be filled by hydrogen such that all valences are satisfied unless otherwise indicated.

In another embodiment, 1 to 3 carbon atoms of the compounds of the invention may be replaced with 1 to 3 silicon atoms so long as all valence requirements are satisfied.

In another embodiment, there is provided a composition comprising a compound of the invention and a pharmaceutically acceptable carrier or diluent.

In one embodiment, the invention is directed to methods of treating a patient (preferably a human) for inflammatory diseases and diseases characterized by defects in cholesterol or lipid metabolism, by administering to the patient a compound of the invention or a pharmaceutically acceptable salt thereof.

The invention is also directed to the use of a compound of the invention for treating inflammatory diseases and diseases characterized by defects in cholesterol or lipid metabolism, by administering to a patient (preferably a human) a compound of the invention or a pharmaceutically acceptable salt thereof.

The invention is also directed to medicaments or pharmaceutical compositions for treating inflammatory diseases and diseases characterized by defects in cholesterol or lipid metabolism, by administering to a patient (preferably a human) a compound of the invention, or a pharmaceutically acceptable salt thereof, and a pharmaceutically acceptable carrier.

The invention is further directed to a the manufacture of a medicament or a composition for inflammatory diseases and diseases characterized by defects in cholesterol or lipid metabolism, by administering to a patient (preferably a human) a compound of the invention or a pharmaceutically acceptable salt thereof, with one or more pharmaceutically acceptable carriers.

Exemplary inflammatory diseases and diseases characterized by defects in cholesterol or lipid metabolism for which the compounds of the invention are useful include neurodegenerative and neurological diseases, such as Alzheimer's Disease, Neimann-Pick disease type C1, Parkinson's Disease, amyotrophic lateral sclerosis, stroke, age-related macular degeneration, psychiatric disorders such as schizophrenia and depression, and metabolic disorders such as cardiovascular disease, obesity and diabetes.

The present invention is directed to the use of the compounds of the invention as LXRβ agonists in a patient or subject such as a mammal in need of such activity, comprising the administration of an effective amount of the compound. In addition to humans, a variety of other mammals can be treated according to the method of the present invention.

The compounds of the invention may have utility in treating or ameliorating Alzheimer's disease. The compounds may also be useful in treating or ameliorating other inflammatory diseases and diseases characterized by defects in cholesterol and lipid metabolism, such as Neimann-Pick disease type C1, Parkinson's Disease, amyotrophic lateral sclerosis, stroke, age-related macular degeneration, psychiatric disorders such as schizophrenia and depression, and metabolic disorders such as cardiovascular disease, obesity and diabetes.

For example, the compounds of the invention may be useful for the prevention of dementia of the Alzheimer's type, as well as for the treatment of early stage, intermediate stage or late stage dementia of the Alzheimer's type.

Potential cardiovascular conditions or disorders for which the compounds of the invention may be useful include atherosclerosis, hypertension, hyperlipidemia, coronary heart disease, peripheral vascular disease, dyslipidemia, hyperbetalipoproteinemia, hypoalphalipoproteinemia, hypercholesterolemia, hypertriglyceridemia, familial-hypercholesterolemia, angina, ischemia, cardiac ischemia, stroke, myocardial infarction, reperfusion injury, angioplastic restenosis, vascular complications of diabetes, obesity (including abdominal obesity) and endotoxemia.

The compounds of the invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease.

The compounds of the invention may also be useful for the treatment of Type 2 diabetes, and conditions and disorders related to Type 2 diabetes, such as (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component.

The compounds of the invention may also have utility in treating certain kinds of cancers which are affected by the LXR mechanism. Such cancers include, but are not limited to, prostate, breast, ovarian, melanoma, pancreas, lung, colon and hematological malignancy. (Lin, C—Y and Gustafsson, J-A, (2015) Nature Reviews Cancer 15, 216-224).

The compounds of the invention may be used in combination with one or more other drugs in the treatment of diseases or conditions for which the compounds of the invention have utility, where the combination of the drugs together are safer or more effective than either drug alone. Additionally, the compounds of the invention may be used in combination with one or more other drugs that treat, prevent, control, ameliorate, or reduce the risk of side effects or toxicity of the compounds of the invention. Such other drugs may be administered, by a route and in an amount commonly used contemporaneously or sequentially with the compounds of the invention. Accordingly, the pharmaceutical compositions of the present invention include those that contain one or more other active ingredients, in addition to the compounds of the invention. The combinations may be administered as part of a unit dosage form combination product, or as a kit or treatment protocol wherein one or more additional drugs are administered in separate dosage forms as part of a treatment regimen.

Examples of combinations of the compounds of the invention include combinations with anti-Alzheimer's Disease agents, for example: other LXRβ agonists; beta-secretase inhibitors including verubecestat (N-[3-[(5R)-3-amino-2,5-dimethyl-1,1-dioxo-6H-1,2,4-thiadiazin-5-yl]-4-fluorophenyl]-5-fluoropyridine-2-carboxamide); alpha 7 nicotinic agonists; ADAM 10 ligands or activators; gamma-secretase inhibitors, such as LY450139 and TAK 070; gamma secretase modulators; tau phosphorylation inhibitors; glycine transport inhibitors; ApoE4 conformational modulators; NR2B antagonists; androgen receptor modulators; blockers of Aβ 13 cortico formation; 5-HT4 agonists, such as PRX-03140; 5-HT6 antagonists, such as xaliproden; 5-HT1a antagonists, such as lecozotan; p25/CDK5 inhibitors; NK1/NK3 receptor antagonists; COX-2 inhibitors; HMG-CoA reductase inhibitors; NSAIDs including ibuprofen; vitamin E; anti-amyloid antibodies (including anti-amyloid humanized monoclonal antibodies), such as bapineuzumab; anti-inflammatory compounds such as I-flurbiprofen, nitroflurbiprofen; PPAR gamma agonists, such as pioglitazone and rosiglitazone; CB-1 receptor antagonists or CB-1 receptor inverse agonists; antibiotics such as doxycycline and rifampin; N-methyl-D-aspartate (NMDA) receptor antagonists, such as memantine, neramexane and EVT101; cholinesterase inhibitors such as galantamine, rivastigmine, donepezil, tacrine, phenserine and ladostigil; growth hormone secretagogues such as ibutamoren, ibutamoren mesylate, and capromorelin; histamine H3 receptor antagonists; AMPA agonists or AMPA modulators; PDE IV inhibitors; GABAA inverse agonists; GSK3β inhibitors; neuronal nicotinic agonists; selective M1 agonists; HDAC inhibitors; and microtubule affinity regulating kinase (MARK) ligands; dimebon; or other drugs that affect receptors or enzymes that either increase the efficacy, safety, convenience, or reduce unwanted side effects or toxicity of the compounds of the invention.

Other examples of combinations of the compounds of the invention include combinations with anti-obesity agents such as apolipoprotein-B secretion/microsomal triglyceride transfer protein (apo-B/MTP) inhibitors, 11β-hydroxy steroid dehydrogenase-1 (11 β-HSD type 1) inhibitors, peptide $YY_{3-36}$ or analogs thereof, MCR-4 agonists, cholecystokinin-A (CCK-A) agonists, monoamine reuptake inhibitors (such as sibutramine), sympathomimetic agents, $β_3$ adrenergic receptor agonists, dopamine agonists (such as bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (such as tetrahydrolipstatin, i.e. orlistat), anorectic agents (such as a bombesin agonist), neuropeptide-Y antagonists (e.g., NPY Y5 receptor antagonists) thyromimetic agents, dehydroepiandrosterone or an analog thereof, glucocorticoid receptor agonists or antagonists, orexin receptor antagonists, glucagon-like peptide-1 receptor agonists, ciliary neurotrophic factors (such as Axokine™, available from Regeneron Pharmaceuticals, Inc., Tarrytown, N.Y. and Procter &

Gamble Company, Cincinnati, Ohio), human agouti-related proteins (AGRP), ghrelin receptor antagonists, histamine 3 receptor antagonists or inverse agonists, neuromedin U receptor agonists and the like.

Other examples of combinations of the compounds of the invention include combinations with antihypertensive agents; anti-inflammatory agents (e.g., COX-2 inhibitors); antidepressants (e.g., fluoxetine hydrochloride (Prozac™)); cognitive improvement agents (e.g., donepezil hydrochloride (Aricept™) and other acetylcholinesterase inhibitors); neuroprotective agents (e.g., memantine); antipsychotic medications (e.g., ziprasidone (Geodon™), risperidone and olanzapine); insulin and insulin analogs (e.g., LysPro insulin); GLP-1 (7-37) (insulinotropin) and GLP-1 (7-36)-NH$_2$; sulfonylureas and analogs thereof: chlorpropamide, glibenclamide, tolbutamide, tolazamide, acetohexamide, Glypizide™, glimepiride, repaglinide, meglitinide; biguanides: metformin, phenformin, buformin; alpha2-antagonists and imidazolines: midaglizole, isaglidole, deriglidole, idazoxan, efaroxan, fluparoxan; other insulin secretagogues: linogliride, A-4166; glitazones: ciglitazone, pioglitazone, englitazone, troglitazone, darglitazone, Avandia™; fatty acid oxidation inhibitors: clomoxir, etomoxir; alpha-glucosidase inhibitors: acarbose, miglitol, emiglitate, voglibose, MDL-25,637, camiglibose, MDL-73,945; β-agonists: BRL 35135, BRL 37344, RO 16-8714, ICI D7114, CL 316,243; phosphodiesterase inhibitors: L-386,398; lipid-lowering agents: benfluorex: fenfluramine; vanadate and vanadium complexes (e.g., Naglivan™) and peroxovanadium complexes; amylin antagonists; glucagon antagonists; gluconeogenesis inhibitors; somatostatin analogs; antilipolytic agents: nicotinic acid, acipimox, WAG 994, pramlintide (Symlin™), AC 2993, nateglinide, aldose reductase inhibitors (e.g., zopolrestat), glycogen phosphorylase inhibitors, sorbitol dehydrogenase inhibitors, sodium-hydrogen exchanger type 1 (NHE-1) inhibitors and/or cholesterol biosynthesis inhibitors or cholesterol absorption inhibitors, especially a HMG-CoA reductase inhibitor, or a HMG-CoA synthase inhibitor, or a HMG-CoA reductase or synthase gene expression inhibitor, a CETP inhibitor, a bile acid sequesterant, a fibrate, an ACAT inhibitor, a squalene synthetase inhibitor, an anti-oxidant or niacin. Non-limiting examples of HMG-CoA reductase inhibitors include statins in their lactonized or dihydroxy open acid forms and pharmaceutically acceptable salts and esters thereof, including but not limited to lovastatin; simvastatin; dihydroxy open-acid simvastatin, particularly the ammonium or calcium salts thereof; pravastatin, particularly the sodium salt thereof; fluvastatin, particularly the sodium salt thereof; atorvastatin, particularly the calcium salt thereof; cerivastatin, particularly the sodium salt thereof, and nisvastatin.

The compounds of the invention may also be administered in combination with a naturally occurring compound that acts to lower plasma cholesterol levels. Such naturally occurring compounds are commonly called nutraceuticals and include, for example, garlic extract, Hoodia plant extracts, and niacin.

Other examples of combinations of the compounds of the invention include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, corticotrophi, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be used in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the compounds of the invention may be used in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Other examples of combinations of the compounds of the invention include combinations with agents for the treatment of stroke or stroke recovery. Examples of such second agents for treatment of stroke include, but are not limited to, aspirin, intercellular adhesion molecule (ICAM)-I and LFA-I antagonists including antibodies such as enlimomab (an anti-ICAM-1 monoclonal antibody), and anti-CD18 and anti-CD 11a antibodies, human anti-leukocytic antibodies such as Hu23F2G, glycoprotein lib IIIa antagonists such as eptifibatide (INTEGRELIN™), direct thrombin inhibitors, external or local ultrasound, mechanical clot retrieval or inaceration, fibrinolytic agents, neuronal wound healing agents such as basic fibroblast growth factor (e.g., FIBLAST™), neuroprotective agents such as citicoline, magnesium, nalmefene, dizocilpine, nimodipine, lamotrigine, sipatrigine, lubeluzole, mexiletine, clomethiazole, calcium and sodium channel blocking agents, beta-amino-3-hydroxy-5-methylisoxazole-4-proprionic acid antagonist, a serotonin agonist, a transmembrane potassium channel modulator, agents that inhibit astrocyte activation (e.g., ONO 2506), antioxidants (e.g., MCI-186), anti-adhesion monoclonal antibodies and antagonists and antibodies inhibiting platelet aggregation such as argatroban and abciximab (REOPRO™), phenytoin, nitrogen oxides, CNS-protective therapies, free-radical scavengers such as tirilazad, reactive oxygen metabolites, and antioxidants, and other thrombolytic agents than tenecteplase, as defined below, such as, for example, acylated plasminogen-streptokinase activator complex (APSAC), single-chain urokinase-plasminogen activator (scu-PA), thrombin-like enzymes from snake venoms such as ancrod, streptokinase (e.g., SAKSTAR™), urokinase, anistreplase, alteplase, saruplase, reteplase, lanoteplase (SUN-9216; Genetics Institute Inc.), plasmin, a truncated form of plasmin (microplasmin; ThromboGenics Ltd), a direct-acting thrombolytic with non-thrombolytic-related neuroprotective activities, recombinant desmodus rotundus salivary plasminogen activator (rDSPA) alpha-1 (Schering/Teijin Pharmaceuticals), a mutant fibrin-activated human plasminogen (BB 101 53; British Biotech Inc.), staphylokinase, fibrolase, prourokinase (intra-arterial administration directly into M1 or M2 arterial thrombus), monteplase (modified rtPA), pamiteplase, tisokinase, and vampire bat plasminogen activator, a spin-trap agent such as NXY-059 (cerovive), clopidogrel, n-methyl-dextro-aspartic acid receptor blocking agent, an anticonvulsive agent, a caspase 3 inhibitor, ((tert butylimino)methyl) 1,3 (benzene-disulfonate disodium n oxide), ebselen, glutathione peroxidase, norphenazone, rovelizumab, lactacystin beta-lactone, tsukubaenolide, 4 phosphonomethylpipecolic acid, eliprodil, antibodies to ganglioside GM1; and thrombolytic agents, including streptokinase, acylated plasminogen-streptokinase activator complex (APSAC), urokinase, single-chain urokinase-plasminogen activator (scu-PA), thrombin-like enzymes from snake venoms such as ancrod (Bell, W. "Defibrinogenating enzymes" In Colman et al (eds), *Hemostasis and Thrombosis Lippincott, Philadelphia* (1987) p. 886), tPA, and biologically active variants of each of the above.

Other examples of combinations of the compounds of the invention include combinations with agents for the treatment of depression or anxiety, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), alpha-adrenoreceptor antagonists, atypical anti-depressants, benzodiazepines, 5-$HT_{1A}$ agonists or antagonists, especially 5-$HT_{1A}$ partial agonists, orticotrophin releasing factor (CRF) antagonists, and pharmaceutically acceptable salts thereof.

Other examples of combinations of the compounds of the invention include combinations with agents for the treatment of diabetes or diabetes conditions, including dipeptidyl peptidase IV (DPP-IV) inhibitors (including isoleucine, thiazolidide, vildagliptin, stigaliptin, and saxagliptin); SGLT inhibitors (e.g., gliflozins such as dapagliflozin, empagliflozin, canagliflozin, ipragliflozin, tofogliflozin, sergliflozin etabonate, remogliflozin etabonate, ertugliflozin, and luseogliflozin/TS-071), insulin sensitizers, including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, tesaglitazar, TAK-559, PPARU agonists, such as fenofibric acid derivatives (gemfibrozil, clofibrate, fenofibrate and bezafibrate), and selective PPAR gamma modulators (SPPARγM's); (ii) biguanides such as metformin and phenformin, and (iii) protein tyrosine phosphatase-1B (PTP-1B) inhibitors; insulin or insulin mimetics; sulfonylureas and other insulin secretagogues, such as tolbutamide, glyburide, glipizide, glimepiride, and meglitinides, such as nateglinide and repaglinide; α-glucosidase inhibitors (such as acarbose and miglitol); glucagon receptor antagonists; GLP-1, GLP-1 analogues or mimetics, and GLP-1 receptor agonists, such as exendin-4 (exenatide), liraglutide; GIP and GIP mimetics and GIP receptor agonists; PACAP, PACAP mimetics, and PACAP receptor agonists; cholesterol lowering agents; PPAR delta agonists; antiobesity agents; ileal bile acid transporter inhibitors; agents intended for use in inflammatory conditions such as aspirin, non-steroidal anti-inflammatory drugs (NSAIDs), glucocorticoids, azulfidine, and selective cyclooxygenase-2 (COX-2) inhibitors; antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers; glucokinase activators (GKAs); inhibitors of 11-j3-hydroxysteroid dehydrogenase type 1; inhibitors of cholesteryl ester transfer protein (CETP), such as torcetrapib; and inhibitors of fructose 1,6-bisphosphatase.

The subject or patient to whom the compounds of the invention is administered is generally a human being, male or female, in whom LXRβ agonism is desired, but may also encompass other mammals, such as dogs, cats, mice, rats, cattle, horses, sheep, rabbits, monkeys, chimpanzees or other apes or primates, for which treatment of the above noted disorders is desired.

Definitions

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, and they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" (or "halo") means fluorine, chlorine, bromine, or iodine. Preferred are fluorine, chlorine and bromine.

"Alkyl" means an aliphatic hydrocarbon group, which may be straight or branched, comprising 1 to 10 carbon atoms. "Lower alkyl" means a straight or branched alkyl group comprising 1 to 4 carbon atoms. Branched means that one or more lower alkyl groups such as methyl, ethyl or propyl, are attached to a linear alkyl chain or to the same methyl group. Non-limiting examples of suitable alkyl groups include methyl, ethyl, n-propyl, isopropyl, n-butyl, i-butyl, and t-butyl.

"Haloalkyl" means an alkyl as defined above wherein one or more hydrogen atoms on the alkyl is replaced by a halo group defined above.

"Alkenyl" means an aliphatic hydrocarbon group containing at least one carbon-carbon double bond and which may be straight or branched and comprising 2 to 10 carbon atoms in the straight or branched chain. Branched means that one or more lower alkyl groups such as methyl, ethyl propyl, ethenyl or propenyl are attached to a linear or branched_alkenyl chain. "Lower alkenyl" means 2 to 4 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising 2 to 10 carbon atoms in the chain. Branched means that one or more lower alkyl groups such as methyl, ethyl or propyl, or lower alkenyl or lower alkynyl groups, are attached to a linear alkynyl chain. "Lower alkynyl" means 2 to 4 carbon atoms in the chain which may be straight or branched. Non-limiting examples of suitable alkynyl groups include ethynyl, propynyl, 2-butynyl and 3-methylbutynyl.

"Aryl" means an aromatic monocyclic or multicyclic ring system comprising 6 to 14 carbon atoms, preferably 6 to 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from N, O, and S, and oxides thereof. The point of attachment to the parent moiety is to any available ring carbon or ring heteroatom. Non-limiting examples of monocyclic heteroaryl moieties include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic monocyclic or multicyclic ring system comprising 3 to 10 carbon atoms, preferably 3 to 6 carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of multicyclic cycloalkyls include [1.1.1]-bicyclopentane, 1-decalinyl, norbornyl, adamantyl and the like.

"Heterocycloalkyl" (or "heterocyclyl") means a non-aromatic saturated monocyclic or multicyclic ring system comprising 3 to 10 ring atoms, preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain 5 to 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). (Such =O groups may be referred to herein as "oxo", further described below.) As used herein, the term "monocyclic heterocycloalkyl" refers monocyclic versions of the heterocycloalkyl moities described herein and include a 4- to 7-membered monocyclic heterocycloalkyl groups comprising from 1 to 4 ring heteroatoms, said ring heteroatoms being independently selected from N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

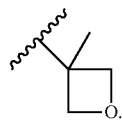

"Oxo" is defined as a oxygen atom that is double bonded to a ring carbon in a cycloalkyl, cycloalkenyl, heterocyclyl, heterocyclenyl, or other ring described herein, e.g.,

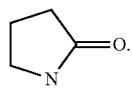

It should be noted that in hetero-atom containing ring systems of this invention, there are no hydroxyl groups on carbon atoms adjacent to a N, O or S, as well as there are no N or S groups on carbon adjacent to another heteroatom.

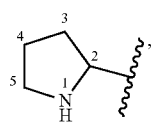

there is no —OH attached directly to carbons marked 2 and 5.

"Alkoxy" means an —O-alkyl group in which the alkyl group is as previously described. Non-limiting examples of alkoxy groups include methoxy, ethoxy, n-propoxy, isopropoxy and n-butoxy. The bond to the parent moiety is through the oxygen.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., R$^6$ in —N(R$^6$)$_2$, or a variable appears more than once in a structure presented herein, the variables can be the same or different.

The compounds of Formula I may have one or more chiral (asymmetric) centers. The present invention encompasses all stereoisomeric forms of the compounds of Formula I. Centers of asymmetry that are present in the compounds of Formula I can all independently of one another have (R) or (S) configuration. When bonds to a chiral carbon are depicted as straight lines in the structural Formulas of the invention, or when a compound name is recited without an (R) or (S) chiral designation for a chiral carbon, it is understood that both the (R) and (S) configurations of each such chiral carbon, and hence each enantiomer or diastereomer and mixtures thereof, are embraced within the formula or by the name.

The line ———, as a bond generally indicates a mixture of, or either of, the possible isomers, e.g., containing (R)- and (S)-stereochemistry. For example:

means

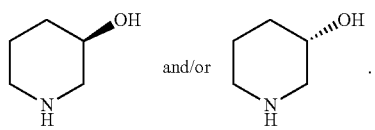

The wavy line ∿∿∿, as used herein, indicates a point of attachment to the rest of the compound. Lines drawn into the ring systems, such as, for example:

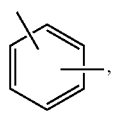

indicate that the indicated line (bond) may be attached to any of the substitutable ring carbon atoms.

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

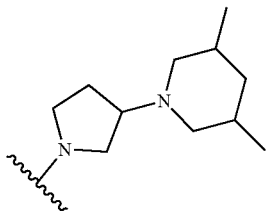 [SMILES: *N1CCC(N2CC(C)CC(C)C2)C1]

represents

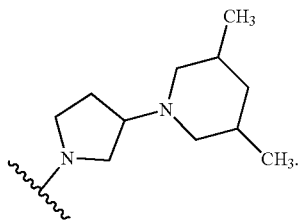 [SMILES: *N1CCC(N2CC(C)CC(C)C2)C1]

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer thereof, or pharmaceutically acceptable salt of said compound or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in organic Synthesis (1991), Wiley, New York.

Those skilled in the art will recognize those instances in which the compounds of the invention may be converted to prodrugs and/or solvates, another embodiment of the present invention. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms where they exist. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "salt(s)", as employed herein, denotes any of the following: acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also potentially useful. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered as potentially useful alternatives to the free forms of the corresponding compounds for purposes of the invention.

Another embodiment which may be useful includes pharmaceutically acceptable esters of the compounds of the invention. Such esters may include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

As mentioned herein, under certain conditions the compounds of the invention may form tautomers. Such tautomers, when present, comprise another embodiment of the invention. It shall be understood that all tautomeric forms of such compounds are within the scope of the compounds of the invention. For example, all keto-enol and imine-enamine forms of the compounds, when present, are included in the invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric. For example, if a compound of the invention incorporates a double bond or a fused ring, both the cis- and trans-forms, as well as mixtures, are embraced within the scope of the invention.

Where various stereoisomers of the compounds of the invention are possible, another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment which may be useful include isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from 0.001 to 500 mg/kg of body weight/day of the compound of the invention. In one embodiment, the dosage is from 0.01 to 25 mg/kg of body weight/day of a compound of the invention, or a pharmaceutically acceptable salt or solvate of said compound. In another embodiment, the quantity of active compound in a unit dose of preparation may be varied or adjusted from 1 mg to 100 mg, preferably from 1 mg to 50 mg, more preferably from 1 mg to 25 mg, according to the particular application. In another embodiment, a typical recommended daily dosage regimen for oral administration can range from 1 mg/day to 500 mg/day, preferably 1 mg/day to 200 mg/day, in two to four divided doses.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. Non-limiting examples which may be useful include water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment which may be useful includes compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Other embodiment which may be useful includes compositions comprising a compound of the invention formulated for subcutaneous delivery or for oral delivery. In some embodiments, it may be advantageous for the pharmaceutical preparation comprising one or more compounds of the invention be prepared in a unit dosage form. In such forms, the preparation may be subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

PREPARATIVE EXAMPLES

The compounds of the invention can be made according to procedures that will be apparent to those of ordinary skill in the art. Several methods for preparing the compounds of this invention are illustrated in the Schemes and examples herein. Starting materials are available commercially or are made according to procedures known in the art or as illustrated herein. The following examples are provided so that the invention might be more fully understood. These examples are illustrative only and should not be construed as limiting the scope of the invention.

General Scheme A outlines a method for preparing compounds of the type A-5. A suitably protected amino ketone or aldehyde (A-1) can be reacted with amine A-2 to form A-3 and then deprotected and coupled to desired activated species to yield amide, sulfonamides or carbamates A-5.

Scheme A

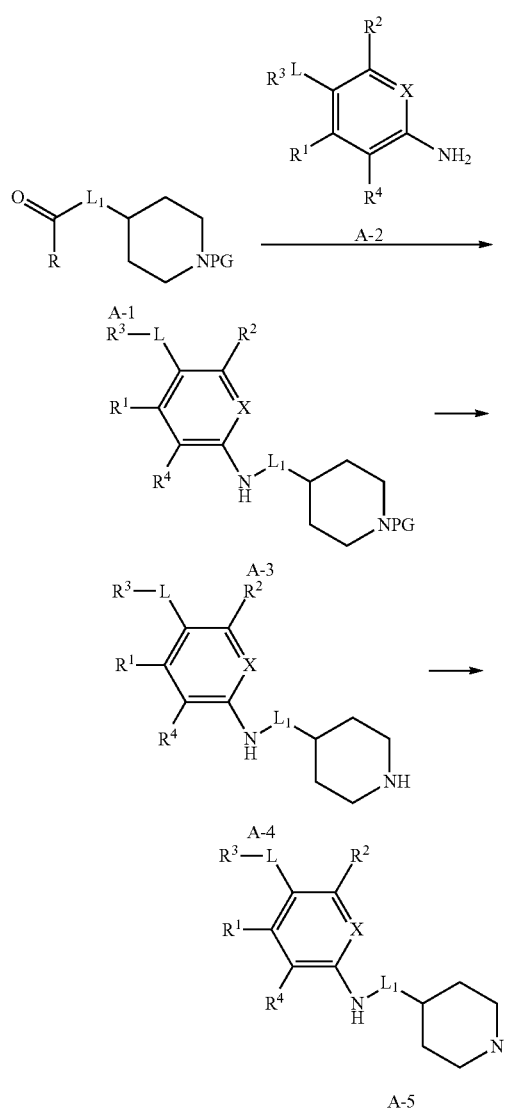

General Scheme B outlines a method for preparing compounds of the type B-5. A suitably protected diamine (B-1) can be reacted with halo/pseudohalo-heterocycle B-2 to form B-3 and then deprotected and coupled to desired activated species to yield amide, sulfonamides or carbamates A-5.

Scheme B

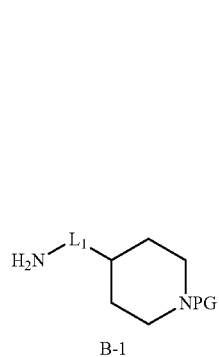

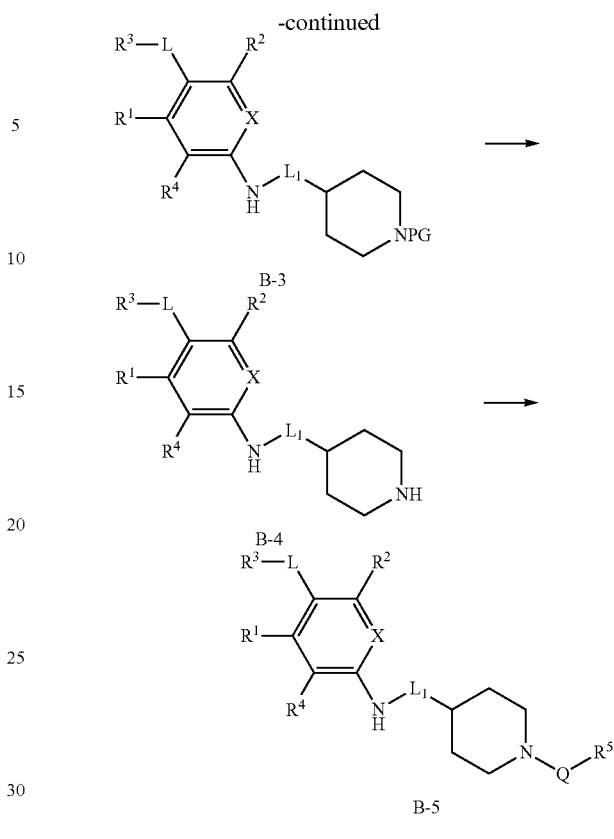

General Scheme C outlines a method for preparing compounds of the type C-2. Amino compound C-1 can be alkylated to yield tertiary amino compound C-2.

Scheme C

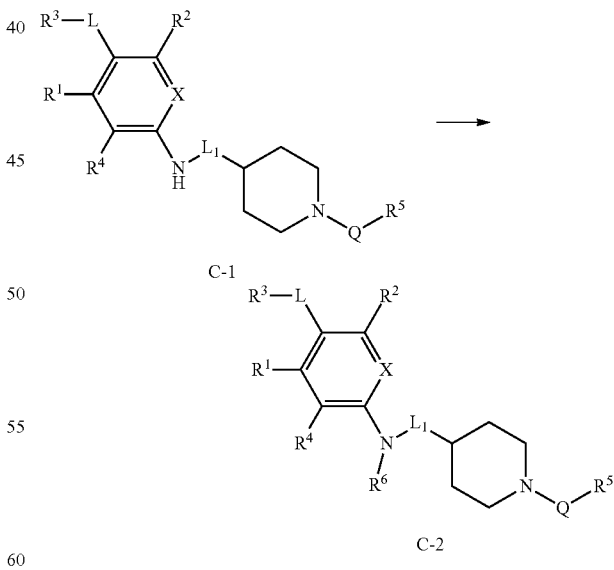

General Scheme D outlines a method for preparing compounds of the type D-5. A suitably protected alkynyl amine (D-1) can be reacted with halo/pseudohalo-heterocycle B-2 to form D-2. The resulting alkyne can then be reduced, the amine deprotected, and coupled to desired activated species to yield amide, sulfonamides or carbamates D-5.

Scheme D

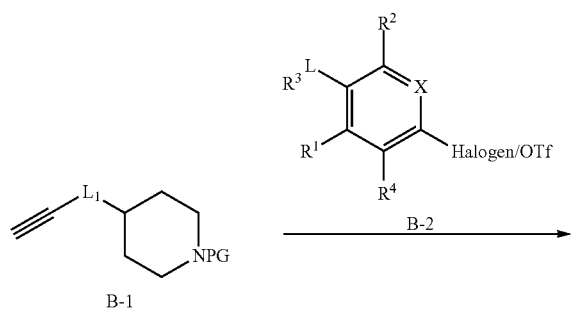

B-1

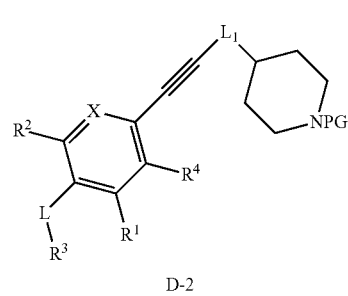

D-2

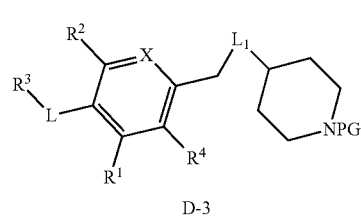

D-3

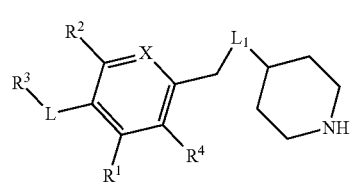

D-4

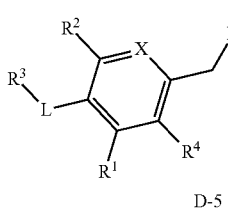

D-5

Scheme E

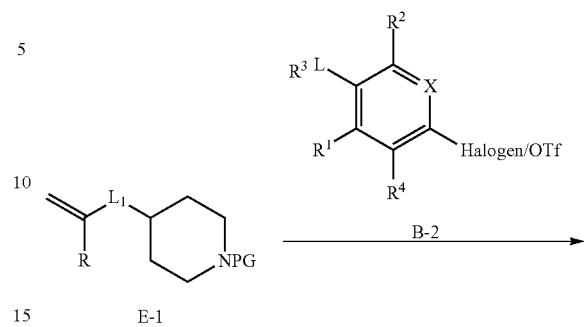

E-1

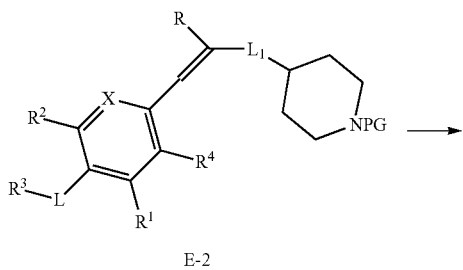

E-2

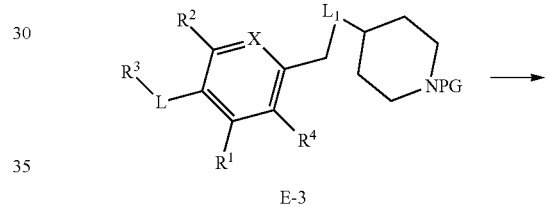

E-3

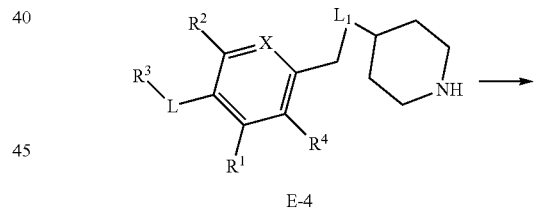

E-4

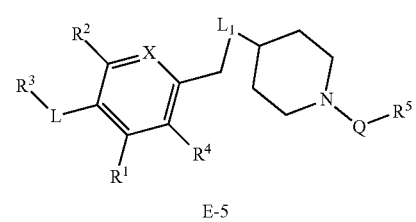

E-5

General Scheme E outlines a method for preparing compounds of the type E-5. A suitably protected alkenyl amine (E-1) can be reacted with halo/pseudohalo-heterocycle B-2 to form E-2. The resulting alkene can then be reduced, the amine deprotected, and coupled to desired activated species to yield amide, sulfonamides or carbamates E-5.

General Scheme F outlines a method for preparing compounds of the type F-6. A suitably protected amino alcohol (F-1) can be reacted with potassium thioacetate to form F-2. Following hydrolysis/dimerization, the thiol can be coupled with halo/pseudohalo-heterocycle B-2 to yield F-4, which after deprotection and coupling to desired activated species to yield amide, sulfonamides or carbamates F-6.

Scheme F
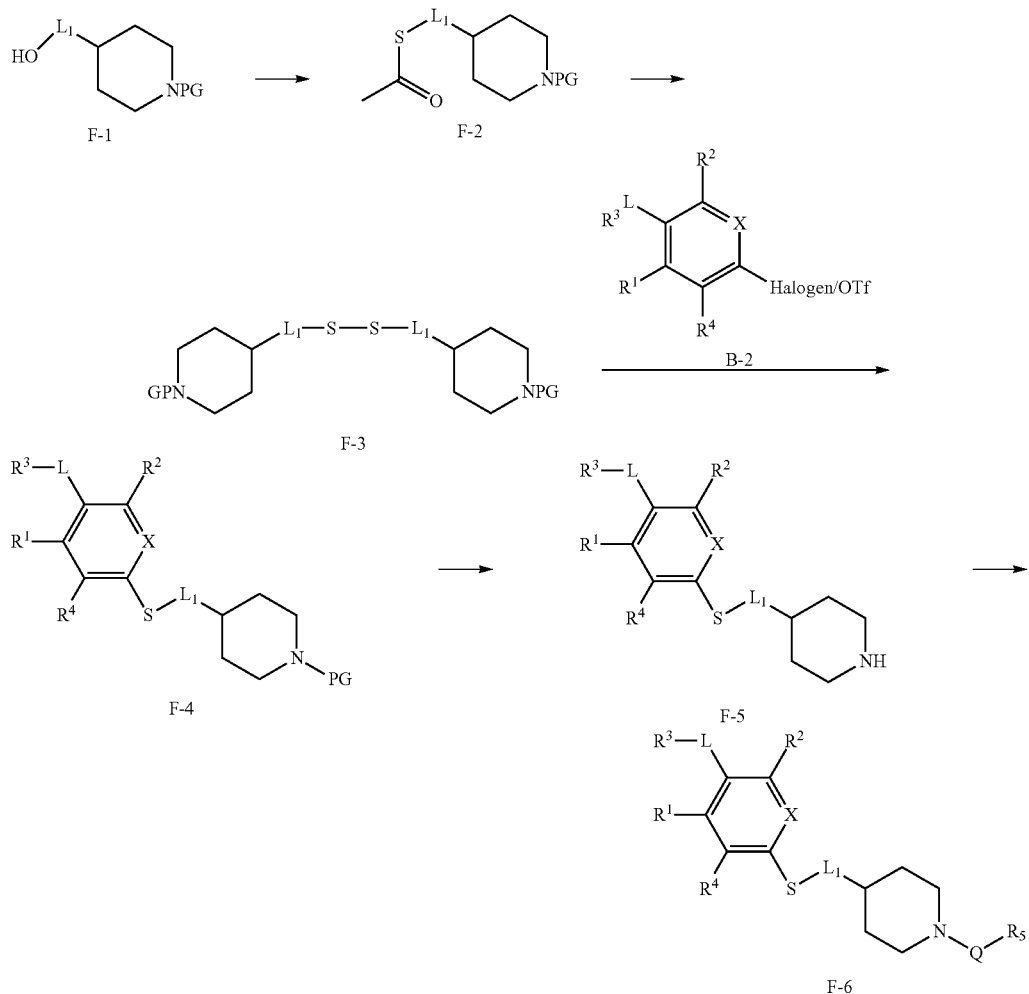
General Scheme G outlines a method for preparing compounds of the type G-10 and G-11. Aniline G-1 can be converted to thiol analog G-2, and after dimerization and alkylation with activated alcohol G-4, G-5 can be produced. Following oxidation and deprotection, coupling with appropriate activated species to yield amide, sulfonamides or carbamates G-10 and G-11.
Scheme G
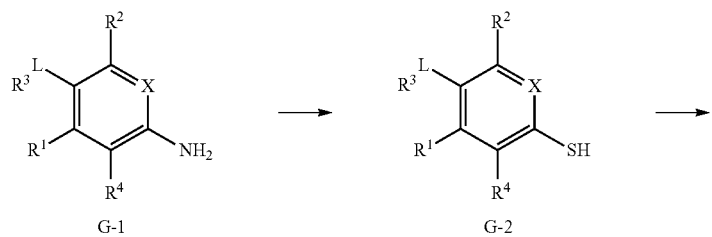

-continued

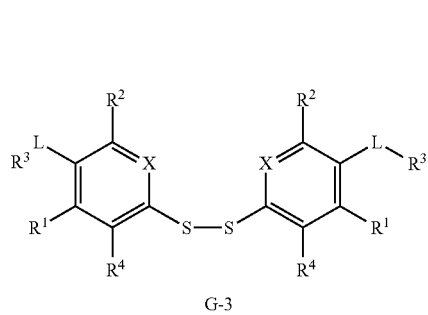
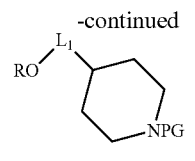
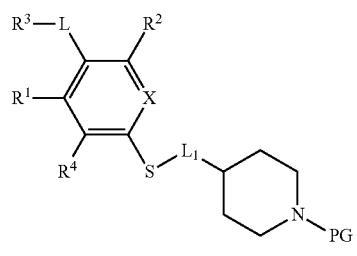

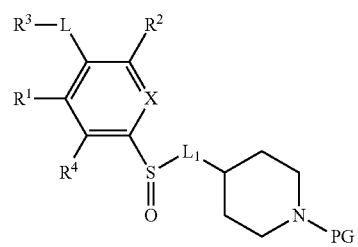
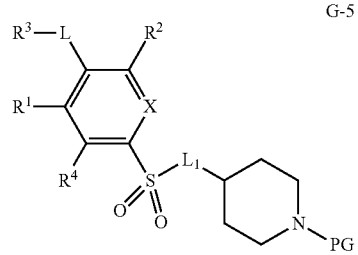

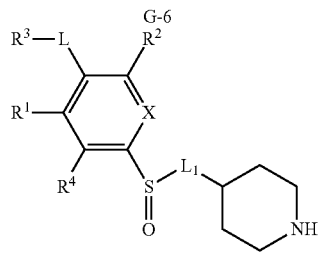
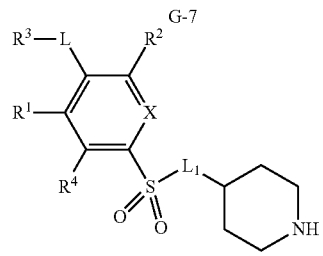

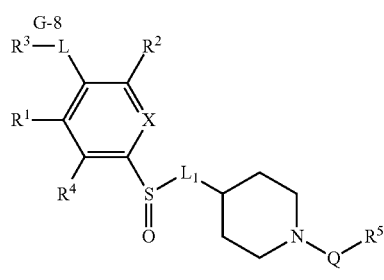
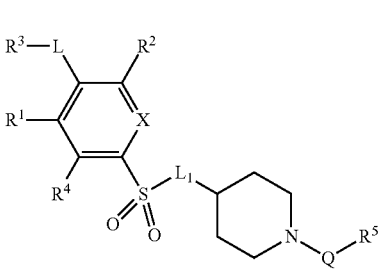

List of Abbreviations
BOP (benzotriazol-1-yloxy)tris(dimethylamino)phosphonium hexafluorophosphate
$Br_2BH$—$SMe_2$ dibromoborane-methylsulfide complex
CDI N,N'-carbonyldiimidazole
$Cs_2CO_3$ cesium carbonate
DCC N,N'-dicyclohexylcarbodiimide
DCE dichloroethane
DCM dichloromethane
DIAD diisopropyl azodicarboxylate
DIBAL-H diisobutylaluminum hydride
DIEA diisopropylethylamine
DMF dimethylformamide
DMSO dimethyl sulfoxide
Dppf diphenylphosphinoferrocene
EDC N-(3-dimethylaminopropyl)-N'-ethylcarbodiimide
$Et_2O$ diethyl ether
$Et_3N$ triethylamine
EtOAc ethyl acetate
EtOH ethanol
HATU O-(7-azabenzotriazol-1-yl)-N,N,N',N'-tetramethyluronium hexafluorophosphate
HCl hydrochloric acid
$(HF)_3$-$Et_3N$ triethylamine trihydrofluoride
IPA isopropanol
$K_2CO_3$ potassium carbonate
$KHSO_4$ potassium bisulfate
LiOH lithium hydroxide
MeCN acetonitrile
MeOH methanol
$MgSO_4$ magnesium Sulfate
$Na_2SO_4$ sodium sulfate
$NaHCO_3$ sodium bicarbonate
NaOH sodium hydroxide
n-BuLi n-butyl lithium
NIS N-iodosuccinimide
$Pd(Ph_3P)_4$ tetrakis(triphenylphosphine) palladium (0)
Pd/C palladium on carbon
$PdCl_2$(dppf)-$CH_2Cl_2$ adduct dichloro[1,1'-bis(diphenylphosphino)ferrocene]palladium (II) dichloromethane adduct
PE petroleum ether
$POCl_3$ phosphorous oxychloride
$PPh_3$ triphenylphosphine RT, r.t., rt room temperature
TBTU O-benzotriazol-1-yl-N,N,N',N'-tetramethyluronium tetrafluoroborate
Tf$_2$O triflic anhydride
TFA trifluoroacetic acid
TfOH trifluoromethanesulfonic acid
THF tetrahydofuran For the examples below, where single isomer is drawn, enantiomers were separated but absolute configuration was not established.

Example 1-1

(R or S)-2-chloro-N-methyl-4-(4-(1-(3,3,3-trifluoro-2-hydroxy-2-(3-methoxyphenyl)propanoyl)piperidin-4-yl)butylamino)benzamide

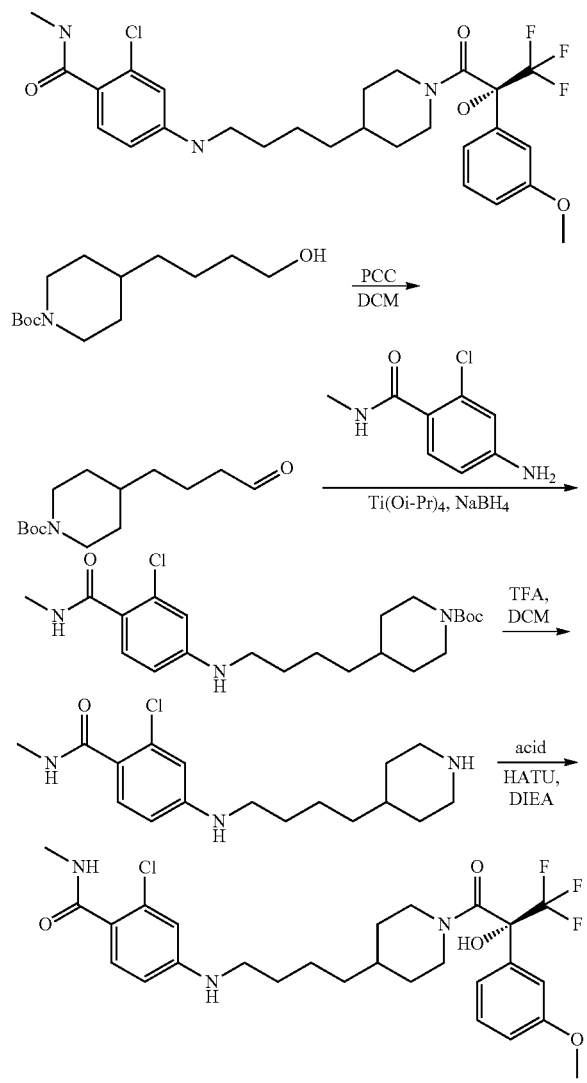

tert-butyl 4-(4-oxobutyl)piperidine-1-carboxylate

To a solution of tert-butyl 4-(4-hydroxybutyl)piperidine-1-carboxylate (400 mg, 1.37 mmol, 1.0 eq) in DCM (10 mL) was added PCC (450 mg, 2.1 mmol, 1.5 eq) and 900 mg of silica gel (100-200 mesh). The mixture was stirred at rt for 1 h. Then the mixture was concentrated in vacuo to give crude product, which was purified by column chromatography (PE:EtOAc=10:1) to give tert-butyl 4-(4-oxobutyl)piperidine-1-carboxylate. LRMS m/z (M-99) 156.2 found, 156.1 required.

tert-butyl 4-(4-(3-chloro-4-(methylcarbamoyl)phenylamino)butyl)piperidine-1-carboxylate To the solution of tert-butyl 4-(4-oxobutyl)piperidine-1-carboxylate (255 mg, 1.0 mmol, 1.0 eq) and 4-amino-2-chloro-N-methylbenzamide (184 mg, 1.0 mmol, 1.0 eq) in DCE (10 mL) was added Ti(Oi-Pr)$_4$ (568 mg, 2.0 mmol, 2.0 eq) at 0° C. under N$_2$ atmosphere. After being stirred for 4 h, NaBH$_4$ (114 mg, 3.0 mmol, 3.0 eq) was added and the resulting mixture was stirred for another 1 h at RT. The reaction mixture was poured into 20 mL of 6N HCl at 0° C. carefully and stirred for 1 h. The aqueous phase was basified with aqueous NaOH and extracted with DCM/MeOH (10:1, 50 ml*3). The combined organic layers were dried over MgSO$_4$ and concentrated. The residue was purified by reverse phase chromatography (Mobile phase: methanol/water (10 mM NH$_4$HCO$_3$)) to give tert-butyl 4-(4-(3-chloro-4-(methylcarbamoyl)phenylamino)butyl)piperidine-1-carboxylate. LRMS m/z (M-99) 325.1 found, 325.2 required.

2-chloro-N-methyl-4-(4-(piperidin-4-yl)butylamino)benzamide

To a solution of tert-butyl 4-(4-(3-chloro-4-(methylcarbamoyl)phenylamino)butyl)piperidine-1-carboxylate (425 mg, 1.0 mmol, 1.0 eq) in dry DCM (2 ml) was added TFA (1.0 ml) at 0° C. The mixture was stirred at 0° C. for 40 min and monitored by TLC. The mixture was concentrated in vacuo to afford the crude product 2-chloro-N-methyl-4-(4-(piperidin-4-yl)butylamino)benzamide. The crude product was used directly in the next step without purification.

(R or S)-2-chloro-N-methyl-4-(4-(1-(3,3,3-trifluoro-2-hydroxy-2-(3-methoxyphenyl)propanoyl)piperidin-4-yl)butylamino)benzamide A mixture of 2-chloro-N-methyl-4-(4-(piperidin-4-yl)butylamino)benzamide (32.5 mg, 0.1 mmol, 1.0 eq), (R or S)-3,3,3-trifluoro-2-hydroxy-2-(3-methoxyphenyl)propanoic acid (30 mg, 0.12 mmol, 1.2 eq), HATU (46 mg, 0.12 mmol, 1.2 eq), and DIEA (39 mg, 0.3 mmol, 3.0 eq) in THF (2 mL) was stirred at rt overnight. The mixture was directly purified by reverse phase chromatography (mobile phase: methanol/water (10 mM NH$_4$HCO$_3$)) to afford (R or S)-2-chloro-N-methyl-4-(4-(1-(3,3,3-trifluoro-2-hydroxy-2-(3-methoxyphenyl)propanoyl)piperidin-4-yl)butylamino)benzamide. LRMS m/z (M+H) 556.1 found, 556.2 required.

Using the same procedure described above, but replacing (R or S)-3,3,3-trifluoro-2-hydroxy-2-(3-methoxyphenyl)propanoic acid with the appropriate acid or replacing 4-amino-2-chloro-N-methylbenzamide with 4-amino-2-chloro-N,N-dimethylbenzamide in the second step and replacing (R or S)-3,3,3-trifluoro-2-hydroxy-2-(3-methoxyphenyl) propanoic acid with 2,6-dichlorobenzene-1-sulfonyl chloride in the last step, or replacing tert-butyl 4-(4-hydroxybutyl)piperidine-1-carboxylate with benzyl 4-(2-hydroxyethyl)piperidine-1-carboxylate in the first step, and replacing 4-amino-2-chloro-N-methylbenzamide with 4-amino-2-chloro-N,N-dimethylbenzamide in the second step, or replacing tert-butyl 4-(4-hydroxybutyl)piperidine-1- carboxylate with benzyl 4-(4-hydroxybutyl)piperidine-1-carboxylate in the first step, and replacing 4-amino-2-chloro-N-methylbenzamide with 4-amino-2-chloro-N,N-dimethylbenzamide in the second step, or replacing 4-amino-2-chloro-N-methylbenzamide with 4-amino-2-chloro-N,N-dimethylbenzamide in the second step, replacing (R or S)-3,3,3-trifluoro-2-hydroxy-2-(3-methoxyphenyl)propanoic acid with (S or R)-3,3,3-trifluoro-2-hydroxy-2-phenylpropanoic acid in the last step, the examples in the table below were prepared.

| Example | Structure | IUPAC | LRMS found [M + H]+ |
|---|---|---|---|
| 1-2 | 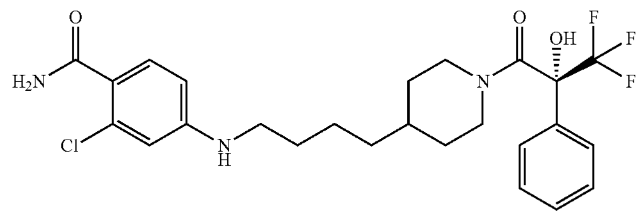 [SMILES: NC(=O)c1ccc(NCCCCC2CCN(C(=O)[C@](O)(c3ccccc3)C(F)(F)F)CC2)cc1Cl] | (R or S)-2-chloro-4-(4-(1-(3,3,3-trifluoro-2-hydroxy-2-phenylpropanoyl)piperidin-4-yl)butylamino)benzamide | 512.1 |
| 1-3 | 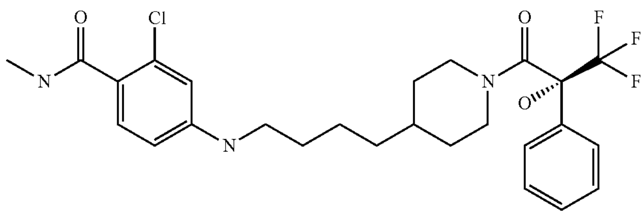 | (R or S)-2-chloro-N-methyl-4-(4-(1-(3,3,3-trifluoro-2-hydroxy-2-phenylpropanoyl)piperidin-4-yl)butylamino)benzamide | 527.1 |
| 1-4 | 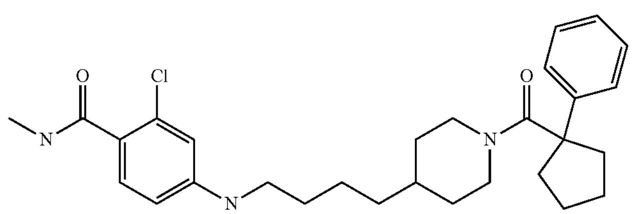 [SMILES: CNC(=O)c1ccc(NCCCCC2CCN(C(=O)C3(c4ccccc4)CCCC3)CC2)cc1Cl] | 2-chloro-N-methyl-4-(4-(1-(1-phenylcyclopentanecarbonyl)piperidin-4-yl)butylamino)benzamide | 496.1 |
| 1-5 | 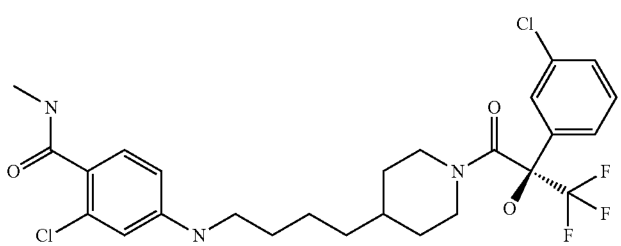 [SMILES: CNC(=O)c1ccc(NCCCCC2CCN(C(=O)[C@](O)(c3cccc(Cl)c3)C(F)(F)F)CC2)cc1Cl] | (R or S)-2-chloro-4-(4-(1-(2-(3-chlorophenyl)-3,3,3-trifluoro-2-hydroxypropanoyl)piperidin-4-yl)butylamino)-N-methylbenzamide | 560.2 |
| 1-6 | 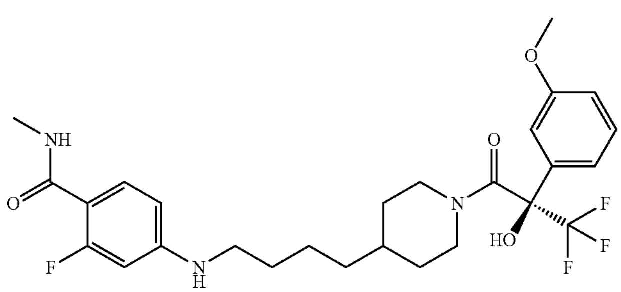 [SMILES: CNC(=O)c1ccc(NCCCCC2CCN(C(=O)[C@](O)(c3cccc(OC)c3)C(F)(F)F)CC2)cc1F] | (R or S)-2-fluoro-N-methyl-4-(4-(1-(3,3,3-trifluoro-2-hydroxy-2-(3-methoxyphenyl)propanoyl)piperidin-4-yl)butylamino)benzamide | 540.2 |
| 1-7 | 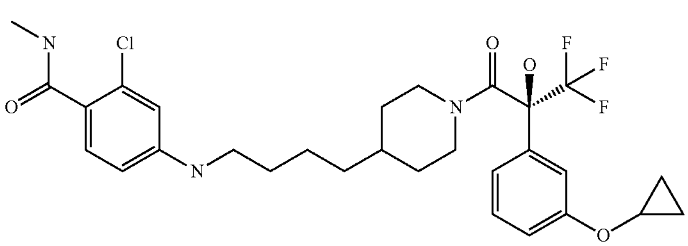 [SMILES: CNC(=O)c1ccc(NCCCCC2CCN(C(=O)[C@@](O)(c3cccc(OC4CC4)c3)C(F)(F)F)CC2)cc1Cl] | (S or R)-2-chloro-4-(4-(1-(2-(3-cyclopropoxyphenyl)-3,3,3-trifluoro-2-hydroxypropanoyl)piperidin-4-yl)butylamino)-N-methylbenzamide | 582.2 |

-continued

| Example | Structure | IUPAC | LRMS found [M + H]+ |
|---|---|---|---|
| 1-8 | 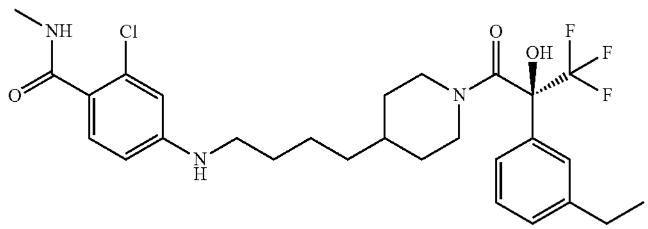 [SMILES: CCc1cccc([C@](O)(C(=O)N2CCC(CCCCNc3ccc(C(=O)NC)c(Cl)c3)CC2)C(F)(F)F)c1] | (S or R)-2-chloro-4-(4-(1-(2-(3-ethylphenyl)-3,3,3-trifluoro-2-hydroxypropanoyl)piperidin-4-yl)butylamino)-N-methylbenzamide | 554.2 |
| 1-9 | 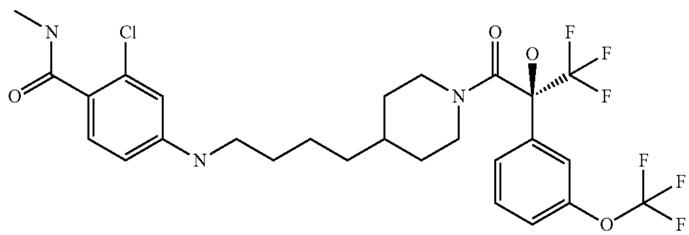 [SMILES: CNC(=O)c1ccc(NCCCCC2CCN(C(=O)[C@@](O)(c3cccc(OC(F)(F)F)c3)C(F)(F)F)CC2)cc1Cl] | (S or R)-2-chloro-N-methyl-4-(4-(1-(3,3,3-trifluoro-2-hydroxy-2-(3-(trifluoromethoxy)phenyl)propanoyl)piperidin-4-yl)butylamino)benzamide | 610.1 |
| 1-10 | 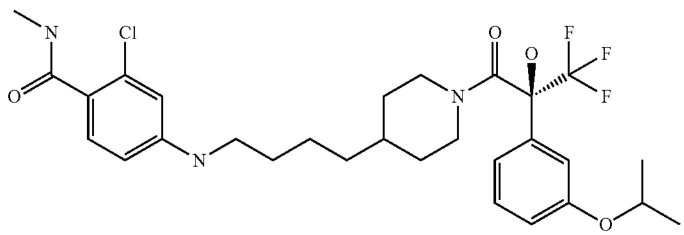 [SMILES: CNC(=O)c1ccc(NCCCCC2CCN(C(=O)[C@@](O)(c3cccc(OC(C)C)c3)C(F)(F)F)CC2)cc1Cl] | (S or R)-2-chloro-N-methyl-4-(4-(1-(3,3,3-trifluoro-2-hydroxy-2-(3-isopropoxyphenyl)propanoyl)piperidin-4-yl)butylamino)benzamide | 584.2 |
| 1-11 | 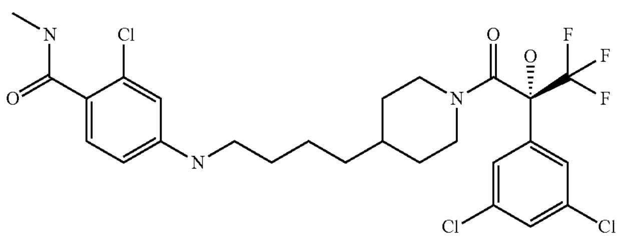 [SMILES: CNC(=O)c1ccc(NCCCCC2CCN(C(=O)[C@](O)(c3cc(Cl)cc(Cl)c3)C(F)(F)F)CC2)cc1Cl] | (R or S)-2-chloro-4-(4-(1-(2-(3,5-dichlorophenyl)-3,3,3-trifluoro-2-hydroxypropanoyl)piperidin-4-yl)butylamino)-N-methylbenzamide | 594.1 |
| 1-12 | 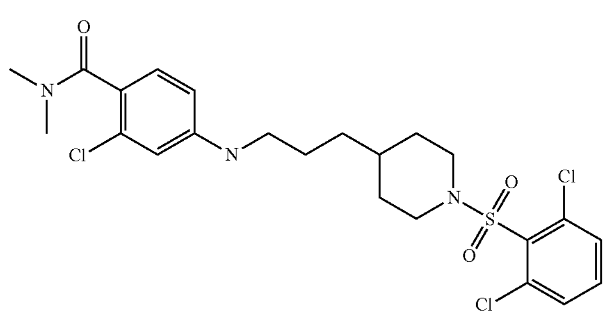 [SMILES: CN(C)C(=O)c1ccc(NCCCC2CCN(S(=O)(=O)c3c(Cl)cccc3Cl)CC2)cc1Cl] | 2-chloro-4-(3-(1-(2,6-dichlorophenylsulfonyl)piperidin-4-yl)propylamino)-N,N-dimethylbenzamide | 534.1 |
| 1-13 | 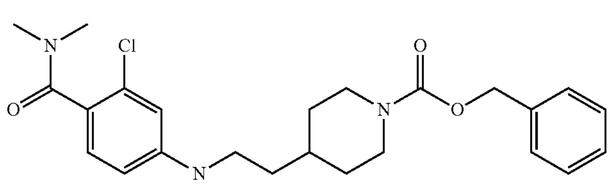 [SMILES: CN(C)C(=O)c1ccc(NCCC2CCN(C(=O)OCc3ccccc3)CC2)cc1Cl] | benzyl 4-(2-(3-chloro-4-(dimethylcarbamoyl)phenylamino)ethyl)piperidine-1-carboxylate | 444.1 |

| Example | Structure | IUPAC | LRMS found [M + H]+ |
|---|---|---|---|
| 1-14 | 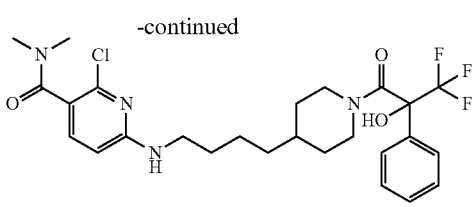 (upper) | benzyl 4-(4-(3-chloro-4-(dimethylcarbamoyl)phenylamino)butyl)piperidine-1-carboxylate | 472.1 |
| 1-15 | 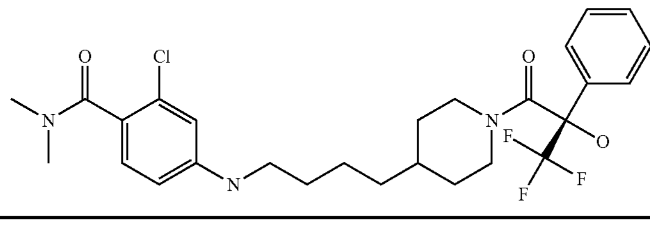 | (S or R)-2-chloro-N,N-dimethyl-4-(4-(1-(3,3,3-trifluoro-2-hydroxy-2-phenylpropanoyl)piperidin-4-yl)butylamino)benzamide | 540.1 |

Example 2-1

2-chloro-N,N-dimethyl-6-(4-(1-(3,3,3-trifluoro-2-hydroxy-2-phenylpropanoyl)piperidin-4-yl)butylamino)nicotinamide

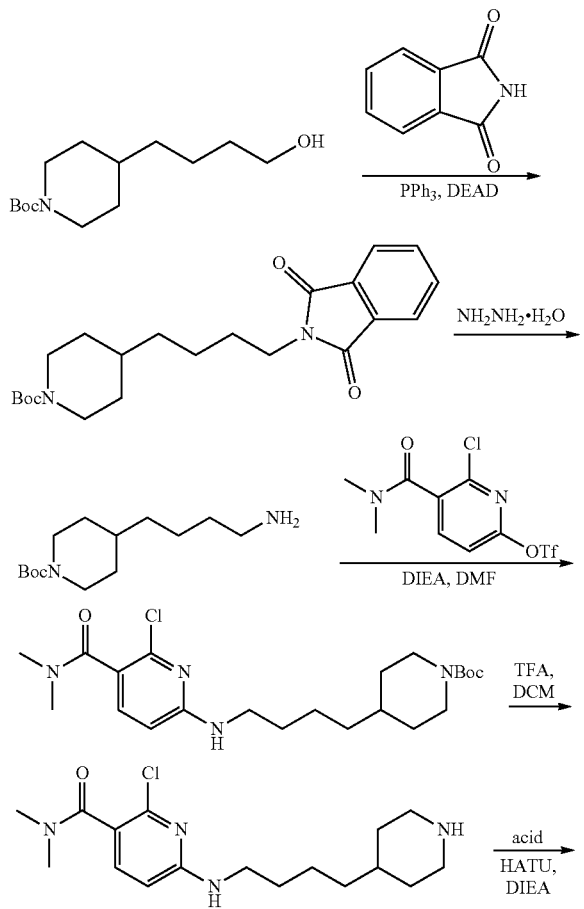

tert-butyl 4-(4-(1,3-dioxoisoindolin-2-yl)butyl)piperidine-1-carboxylate

A mixture of tert-butyl 4-(4-hydroxybutyl)piperidine-1-carboxylate (2 g, 7.8 mmol), isoindoline-1,3-dione (1.37 g, 9.3 mmol), PPh$_3$ (6.1 g, 23.3 mmol) and DEAD (4 g, 23.3 mmol) in THF (20 mL) was stirred at rt overnight. The mixture was concentrated and the residue was purified by reverse phase HPLC (Mobile phase: methanol/water (10 mM NH$_4$HCO$_3$)) to give -butyl 4-(4-(1,3-dioxoisoindolin-2-yl)butyl)piperidine-1-carboxylate. LRMS m/z (M-99) 287.0 found, 287.2 required.

tert-butyl 4-(4-aminobutyl)piperidine-1-carboxylate

A mixture of -butyl 4-(4-(1,3-dioxoisoindolin-2-yl)butyl)piperidine-1-carboxylate (470 mg, 1.2 mmol) and hydrazine (10 mL, 40% in water) in EtOH (5 mL) was stirred at rt for 2 h. The mixture was filtered and the filtrate was concentrated to give tert-butyl 4-(4-aminobutyl)piperidine-1-carboxylate which was used in next step without purification. LRMS m/z (M+H) 257.2 found, 257.2 required.

tert-butyl 4-(4-(6-chloro-5-(dimethylcarbamoyl)pyridin-2-ylamino)butyl)piperidine-1-carboxylate A mixture of tert-butyl 4-(4-aminobutyl)piperidine-1-carboxylate (257 mg, 1 mmol), 6-chloro-5-(dimethylcarbamoyl)pyridin-2-yl trifluoromethanesulfonate (333 mg, 1 mmol) and DIEA (260 mg, 2 mmol) in CH$_3$CN (10 mL) was refluxed overnight. The mixture was concentrated and the crude was purified by chromatography (silica gel: 300-400 mesh, DCM/MeOH=50/1 to 10/1 to afford tert-butyl 4-(4-(6-chloro-5-(dimethylcarbamoyl)pyridin-2-ylamino)butyl)piperidine-1-carboxylate. LRMS m/z (M+H) 439.0 found, 439.2 required.

2-chloro-N,N-dimethyl-6-(4-(piperidin-4-yl)butylamino)nicotinamide

A mixture of tert-butyl 4-(4-(6-chloro-5-(dimethylcarbamoyl)pyridin-2-ylamino)butyl)piperidine-1-carboxylate (190 mg, 0.43 mmol) and 4M HCl/dioxane (2.2 mL) in DCM (5 mL) was stirred at rt for 3 h. The mixture was concentrated to give crude 2-chloro-N,N-dimethyl-6-(4-(piperidin-4-yl)butylamino)nicotinamide. LRMS m/z (M+H) 339.0 found, 339.2 required.

2-chloro-N,N-dimethyl-6-(4-(1-(3,3,3-trifluoro-2-hydroxy-2-phenylpropanoyl)piperidin-4-yl)butylamino)nicotinamide A mixture of 2-chloro-N,N-dimethyl-6-(4-(piperidin-4-yl)butylamino)nicotinamide (45 mg, 0.1 mmol), 3,3,3-trifluoro-2-hydroxy-2-phenylpropanoic acid (26 mg, 0.12 mmoL), HATU (46 mg, 0.12 mmol) and DIEA (26 mg, 0.2 mmol) in THF (2 mL) was stirred at rt overnight. The mixture was directly purified by reverse phase HPLC (Mobile phase: methanol/water (10 mM $NH_4HCO_3$)) to afford 2-chloro-N,N-dimethyl-6-(4-(1-(3,3,3-trifluoro-2-hydroxy-2-phenylpropanoyl)piperidin-4-yl)butylamino)nicotinamide. LRMS m/z (M+H) 541.2 found, 541.2 required.

Example 3-1

(S or R)-2-chloro-N,N-dimethyl-4-(methyl(3-(1-(3,3,3-trifluoro-2-hydroxy-2-phenylpropanoyl)piperidin-4-yl)propyl)amino)benzamide

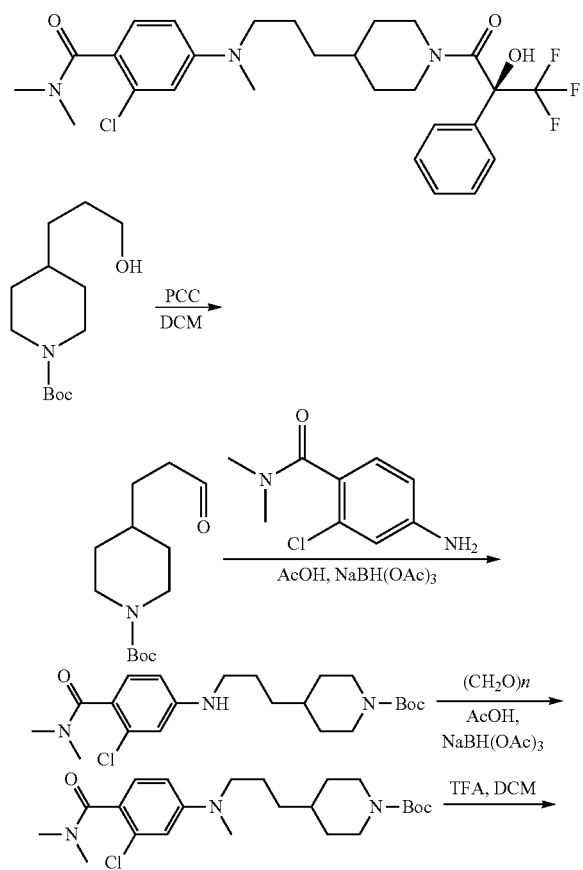

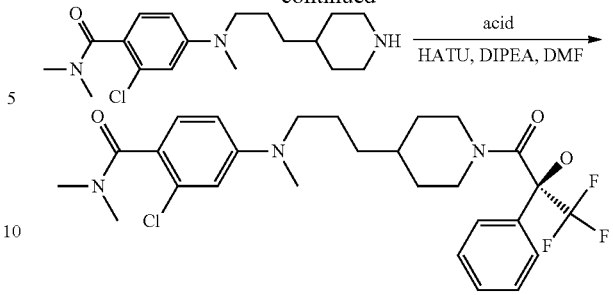

tert-butyl 4-(3-oxopropyl)piperidine-1-carboxylate

A mixture of tert-butyl 4-(3-hydroxypropyl)piperidine-1-carboxylate (800 mg, 3.29 mmol), PCC (2129 mg, 9.88 mmol) in dichloromethane (25 mL) was stirred at rt for 2 h and diluted with dichloromethane (300 mL). The mixture was filtered through a celite pad, and the filtrate was concentrated to give crude product which was purified by column chromatography (silica gel: 200-300 mesh, PE/EtOAc=5/1, v/v) to afford tert-butyl 4-(3-oxopropyl)piperidine-1-carboxylate. LRMS m/z (M-55) 186.1 found, 186.1 required.

tert-butyl 4-(3-(3-chloro-4-(dimethylcarbamoyl)phenylamino)propyl)piperidine-1-carboxylate A solution of tert-butyl 4-(3-oxopropyl)piperidine-1-carboxylate (685 mg, 2.84 mmol), 4-amino-2-chloro-N,N-dimethylbenzamide (620 mg, 3.13 mmol), $NaBH(OAc)_3$ (1809 mg, 8.53 mmol) and AcOH (0.3 mL) in DCE (25 mL) was stirred for 2 h at rt under nitrogen atmosphere. The mixture was concentrated and re-dissolved with dichloromethane (500 ml), washed with saturated $NaHCO_3$ (50 mL*2), brine (50 mL). The organic layer was dried over anhydrous $Na_2SO_4$, filtered and concentrated to afford crude product tert-butyl 4-(3-(3-chloro-4-(dimethylcarbamoyl)phenylamino)propyl)piperidine-1-carboxylate. LRMS m/z (M-55) 368.3 found, 368.2 required.

tert-butyl 4-(3-((3-chloro-4-(dimethylcarbamoyl)phenyl)(methyl)amino)propyl)piperidine-1-carboxylate A solution of crude tert-butyl 4-(3-(3-chloro-4-(dimethylcarbamoyl)phenylamino)propyl)piperidine-1-carboxylate (1000 mg, 2.36 mmol), paraformaldehyde (1064 mg, 11.82 mmol), $NaBH(OAc)_3$ (1504 mg, 7.10 mmol) and AcOH (0.5 mL) in DCE (25 mL) was stirred for 2 h at 50° C. under nitrogen atmosphere. The mixture was diluted with EtOAc (450 mL) and washed with brine (20 mL), and dried over anhydrous $Na_2SO_4$, filtered and concentrated to afford tert-butyl 4-(3-((3-chloro-4-(dimethylcarbamoyl)phenyl)(methyl)amino)propyl)piperidine-1-carboxylate. LRMS m/z (M+H) 438.3 found, 438.2 required.

2-chloro-N,N-dimethyl-4-(methyl(3-(piperidin-4-yl)propyl)amino)benzamide

A solution of tert-butyl 4-(3-((3-chloro-4-(dimethylcarbamoyl)phenyl)(methyl)amino)propyl)piperidine-1-carboxylate (500 mg, 1.14 mmol), TFA (3 mL) in DCM (10 mL) was stirred for 1.5 h at rt. The mixture was concentrated. The pH value was adjusted to 9.0 with saturated NaHCO₃. The aqueous was extracted with DCM/CH₃OH (10/1, 300 mL*2) and washed with brine (20 mL), and dried over anhydrous Na₂SO₄, filtered and concentrated to afford 2-chloro-N,N-dimethyl-4-(methyl(3-(piperidin-4-yl)propyl) amino)benzamide. LRMS m/z (M+H) 338.3 found, 338.2 required.

(S or R)-2-chloro-N,N-dimethyl-4-(methyl(3-(1-(3,3,3-trifluoro-2-hydroxy-2-phenylpropanoyl)piperidin-4-yl)propyl)amino)benzamide A solution of 2-chloro-N,N-dimethyl-4-(methyl(3-(piperidin-4-yl)propyl)amino)benzamide (350 mg, 1.04 mmol), (S or R)-3,3,3-trifluoro-2-hydroxy-2-phenylpropanoic acid (343 mg, 1.56 mmol), HATU (593 mg, 1.56 mmol), DIPEA (201 mg, 1.56 mmol) in DMF (3 mL) was stirred overnight at rt. The mixture was purified by reverse phase HPLC (mobile phase: methanol/water (10 mM NH₄HCO₃)) to afford (S or R)-2-chloro-N,N-dimethyl-4-(methyl(3-(1-(3,3,3-trifluoro-2-hydroxy-2-phenylpropanoyl)piperidin-4-yl) propyl)amino)benzamide. LRMS m/z (M+H) 540.1 found, 540.2 required.

Example 4-1

2-chloro-N,N-dimethyl-4-((S or R)-5-(1-((R or S)-3,3,3-trifluoro-2-hydroxy-2-(3-methoxyphenyl)propanoyl)piperidin-4-yl)pentan-2-ylamino)benzamide

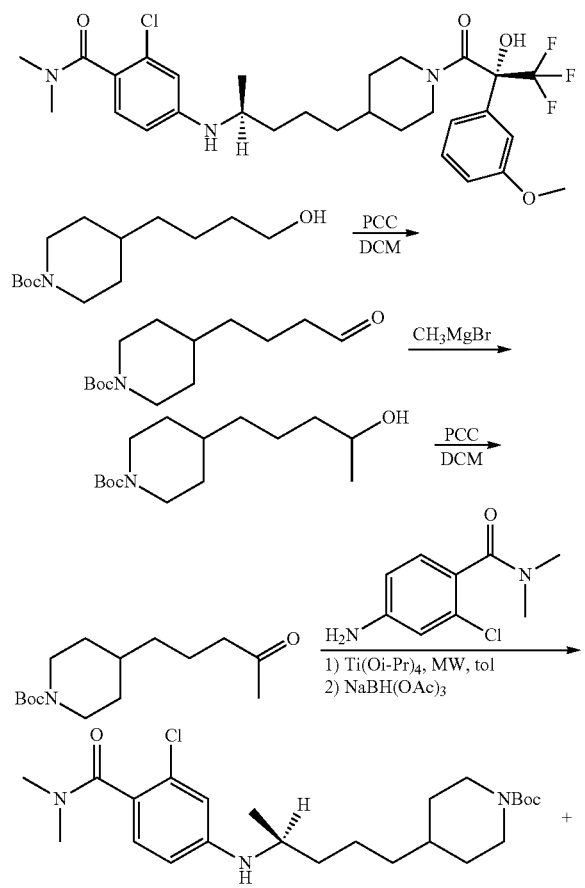

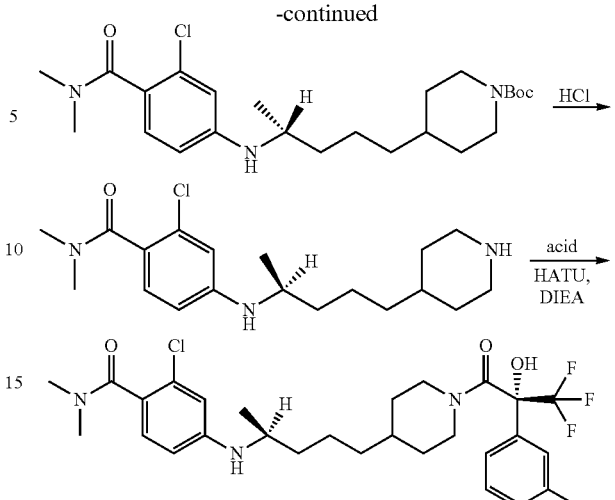

tert-butyl 4-(4-oxobutyl)piperidine-1-carboxylate

To a solution of tert-butyl 4-(4-hydroxybutyl)piperidine-1-carboxylate (1 g, 3.9 mmol) in DCM (40 ml) was added PCC (1.68 g, 7.78 mmol) at rt. The mixture was stirred at rt for 3 h and monitored by LC-MS. The mixture was washed with water (50 ml×2). The organic phase was washed with brine (10 mL). After concentration, the residue was purified by column chromatography (EtOAc: PE=5/95) to afford tert-butyl 4-(4-oxobutyl)piperidine-1-carboxylate. LRMS m/z (M+H) 256.2 found, 256.2 required.

Tert-butyl-4-(4-hydroxypentyl)piperidine-1-carboxylate

To a solution of tert-butyl 4-(4-oxobutyl)piperidine-1-carboxylate (900 mg, 3.9 mmol) in THF (10 ml) at −78° C. was added methylmagnesium bromide (2 ml, 6 mmol, 3 M in diethyl ether). The mixture was then stirred at 0° C. for 2 h, and quenched with saturated NH₄Cl (20 mL), extracted with EtOAc (30 ml×3). The organic phase was washed with sat. NH₄Cl (10 mL), brine (10 mL), dried over anhydrous sodium sulfate, filtered and concentrated to afford tert-butyl-4-(4-hydroxypentyl)piperidine-1-carboxylate which was used in next step without purification. LRMS m/z (M+H) 272.2 found, 272.2 required.

Tert-butyl 4-(4-oxopentyl)piperidine-1-carboxylate

To a solution of tert-butyl-4-(4-hydroxypentyl)piperidine-1-carboxylate (900 mg, 3.6 mmol) in dry DCM (5.0 ml) was added PCC (1.68 g, 7.88 mmol). The mixture was stirred at rt for 3 h, concentrated. And the residue was purified by column chromatography (EtOAc/PE=1/9) to afford tert-butyl 4-(4-oxopentyl)piperidine-1-carboxylate. LRMS m/z (M+H) 270.2 found, 270.2 required.

(S or R)-tert-butyl 4-(4-(3-chloro-4-(dimethylcarbamoyl)phenylamino)pentyl)piperidine-1-carboxylate (5)

To a solution of tert-butyl 4-(4-oxopentyl)piperidine-1-carboxylate (600 mg, 3.6 mmol) in dry toluene (5.0 ml) was added 4-amino-2-chloro-N,N-dimethylbenzamide (500 mg, 3.88 mmol) and Ti(Oi-Pr)₄ (700 mg, 4.0 mmol). The mixture was heated to 150° C. under microwave for 4 h. Then the mixture was cooled to rt and NaBH(AcO)₃ (800 mg, 5.0 mmol) was added. The resulting mixture was stirred at 20° C. for 1 h, diluted with EtOAc (100 mL) and washed with water (50 ml×2). The organic phase was washed with brine (10 mL), dried over anhydrous Na₂SO₄, filtered and concentrated. The residue was purified by column chromatography (EtOAc/PE=5/95) to afford tert-butyl4-(4-(3-chloro-4-(dimethylcarbamoyl)phenylamino)pentyl)piperidine-1-carboxylate. LRMS m/z (M+H) 452.2 found, 452.3 required. The racemic product was resolved by chiral HPLC (column: AD-H (250*4.6 mm 5 um); mobile phase: SCF—CO₂:MeOH (0.1% DEA)=70:30; flow: 3 ml/min) to afford the (S or R)-tert-butyl 4-(4-(3-chloro-4-(dimethylcarbamoyl)phenylamino)pentyl)piperidine-1-carboxylate (RT=2.45 min) and (R or S)-tert-butyl 4-(4-(3-chloro-4-(dimethylcarbamoyl)phenylamino)pentyl)piperidine-1-carboxylate (RT=3.08 min). The absolute stereochemistry was not confirmed.

(S or R)-2-chloro-N,N-dimethyl-4-(5-(piperidin-4-yl)pentan-2-ylamino)benzamide

A mixture of (S or R)-tert-butyl 4-(4-(3-chloro-4-(dimethylcarbamoyl)phenylamino)pentyl)piperidine-1-carboxylate (200 mg, 1.42 mmol) in 4M HCl/dioxane (2 ml) was stirred at rt for 30 min. The mixture was concentrated to afford (S or R)-2-chloro-N,N-dimethyl-4-(5-(piperidin-4-yl)pentan-2-ylamino)benzamide. LRMS m/z (M+H) 352.2 found, 352.2 required 2-chloro-N,N-dimethyl-4-((S or R)-5-(1-((R or S)-3,3,3-trifluoro-2-hydroxy-2-(3-methoxyphenyl)propanoyl)piperidin-4-yl)pentan-2-ylamino)benzamide To a solution of (S or R)-2-chloro-N,N-dimethyl-4-(5-(piperidin-4-yl)pentan-2-ylamino)benzamide (20 mg, 0.042 mmol) in DMF (0.8 ml) was added DIEA (27 ul, 0.21 mmol) and HATU (18 mg, 0.046 mmol). The mixture was stirred at rt for 30 min before (R or S)-3,3,3-trifluoro-2-hydroxy-2-(3-methoxyphenyl)propanoic acid (12.5 mg, 0.050 mmol) in DMF (0.2 ml) was added. The mixture was allowed to stir at rt for 12 h. The target product was purified by reverse phase chromotography (Mobile phase: methanol/water (10 mM NH₄HCO₃))) to afford 2-chloro-N,N-dimethyl-4-((S or R)-5-(1-((R or S)-3,3,3-trifluoro-2-hydroxy-2-(3-methoxyphenyl)propanoyl)piperidin-4-yl)pentan-2-ylamino)benzamide. LRMS m/z (M+H) 584.2 found, 584.2 required Using the same procedure described for example 4-1, but replacing (R or S)-3,3,3-trifluoro-2-hydroxy-2-(3-methoxyphenyl)propanoic acid with the appropriate acid in the last step, or replacing (S or R)-tert-butyl 4-(4-(3-chloro-4-(dimethylcarbamoyl)phenylamino)pentyl)piperidine-1-carboxylate with (R or S)-tert-butyl 4-(4-(3-chloro-4-(dimethylcarbamoyl)phenylamino)pentyl)piperidine-1-carboxylate in the fourth step and replacing (R or S)-3,3,3-trifluoro-2-(3-methoxyphenyl)propanoic acid with the appropriate acid in the last step, the examples in the table below were prepared.

| Example | Structure | IUPAC Name | LRMS, found M + H]+ |
|---|---|---|---|
| 4-2 | 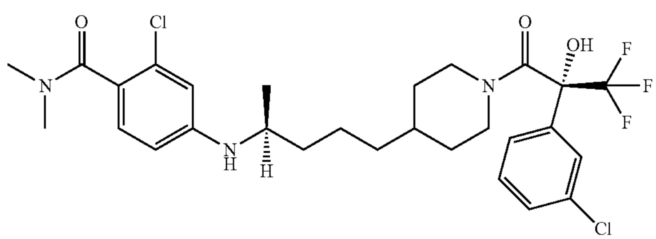 | 2-chloro-4-((S or R)-5-(1-((R or S)-2-(3-chlorophenyl)-3,3,3-trifluoro-2-hydroxypropanoyl)piperidin-4-yl)pentan-2-ylamino)-N,N-dimethylbenzamide | 588.3 |
| 4-3 | 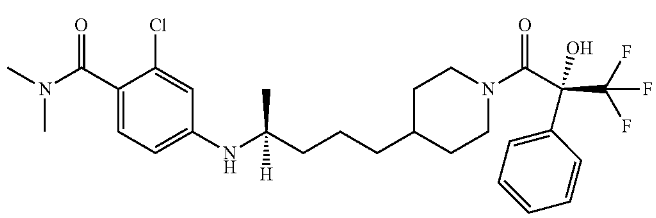 | 2-chloro-N,N-dimethyl-4-((S or R)-5-(1-((R or S)-3,3,3-trifluoro-2-hydroxy-2-phenylpropanoyl)piperidin-4-yl)pentan-2-ylamino)benzamide | 554.2 |
| 4-4 | 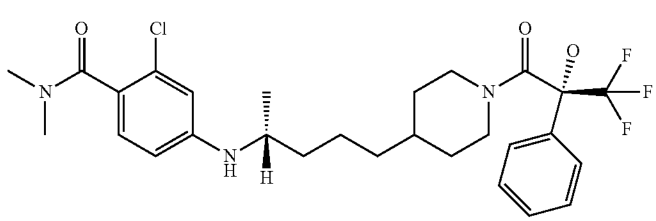 | 2-chloro-N,N-dimethyl-4-((R or S)-5-(1-((R or S)-3,3,3-trifluoro-2-hydroxy-2-phenylpropanoyl)piperidin-4-yl)pentan-2-ylamino)benzamide | 554.2 |

| Example | Structure | IUPAC Name | LRMS, found M + H]+ |
|---|---|---|---|
| 4-5 | 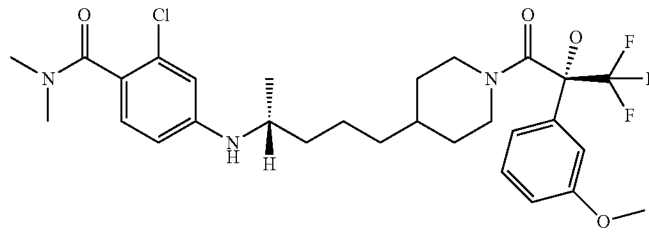 | 2-chloro-N,N-dimethyl-4-((R or S)-5-(1-((R or S)-3,3,3-trifluoro-2-hydroxy-2-(3-methoxyphenyl)propanoyl)piperidin-4-yl)pentan-2-ylamino)benzamide | 584.2 |

Example 5-1

2-chloro-N,N-dimethyl-4-(1-((S or R)-6-(1-phenyl-cyclobutanecarbonyl)-6-azaspiro[2.5]octan-1-yl)propan-2-ylamino)benzamide

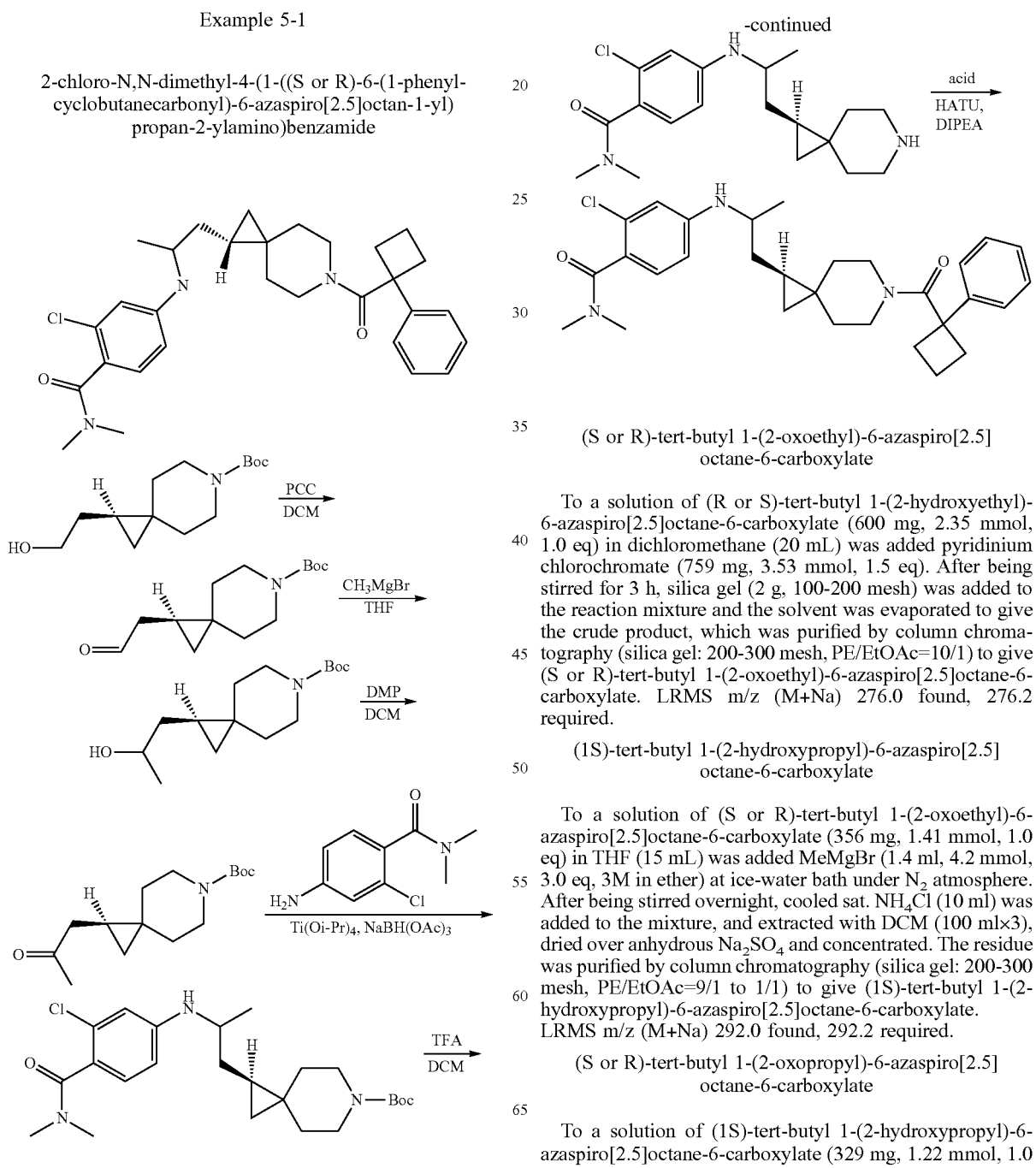

(S or R)-tert-butyl 1-(2-oxoethyl)-6-azaspiro[2.5]octane-6-carboxylate

To a solution of (R or S)-tert-butyl 1-(2-hydroxyethyl)-6-azaspiro[2.5]octane-6-carboxylate (600 mg, 2.35 mmol, 1.0 eq) in dichloromethane (20 mL) was added pyridinium chlorochromate (759 mg, 3.53 mmol, 1.5 eq). After being stirred for 3 h, silica gel (2 g, 100-200 mesh) was added to the reaction mixture and the solvent was evaporated to give the crude product, which was purified by column chromatography (silica gel: 200-300 mesh, PE/EtOAc=10/1) to give (S or R)-tert-butyl 1-(2-oxoethyl)-6-azaspiro[2.5]octane-6-carboxylate. LRMS m/z (M+Na) 276.0 found, 276.2 required.

(1S)-tert-butyl 1-(2-hydroxypropyl)-6-azaspiro[2.5]octane-6-carboxylate

To a solution of (S or R)-tert-butyl 1-(2-oxoethyl)-6-azaspiro[2.5]octane-6-carboxylate (356 mg, 1.41 mmol, 1.0 eq) in THF (15 mL) was added MeMgBr (1.4 ml, 4.2 mmol, 3.0 eq, 3M in ether) at ice-water bath under $N_2$ atmosphere. After being stirred overnight, cooled sat. $NH_4Cl$ (10 ml) was added to the mixture, and extracted with DCM (100 ml×3), dried over anhydrous $Na_2SO_4$ and concentrated. The residue was purified by column chromatography (silica gel: 200-300 mesh, PE/EtOAc=9/1 to 1/1) to give (1S)-tert-butyl 1-(2-hydroxypropyl)-6-azaspiro[2.5]octane-6-carboxylate. LRMS m/z (M+Na) 292.0 found, 292.2 required.

(S or R)-tert-butyl 1-(2-oxopropyl)-6-azaspiro[2.5]octane-6-carboxylate

To a solution of (1S)-tert-butyl 1-(2-hydroxypropyl)-6-azaspiro[2.5]octane-6-carboxylate (329 mg, 1.22 mmol, 1.0 eq) in DCM (15 ml) was added Dess-Martin periodinane (1.04 g, 2.45 mmol, 2 eq). After being stirred overnight, the reaction mixture was quenched by sat. NaHCO$_3$ (10 ml) and extracted with EtOAc (15 ml*3). The organic phase was dried over anhydrous Na$_2$SO$_4$ and concentrated. The residue was purified by column chromatography (silica gel: 200-300 mesh, PE/EtOAc=10/1) to give (S or R)-tert-butyl 1-(2-oxopropyl)-6-azaspiro[2.5]octane-6-carboxylate. LRMS m/z (M+Na) 290.0 found, 290.2 required.

(1S)-tert-butyl 1-(2-(3-chloro-4-(dimethylcarbamoyl)phenylamino)propyl)-6-azaspiro[2.5]octane-6-carboxylate A mixture of (S or R)-tert-butyl 1-(2-oxopropyl)-6-azaspiro[2.5]octane-6-carboxylate (163 mg, 0.61 mmol), 4-amino-2-chloro-N,N-dimethylbenzamide (181 mg, 0.92 mmol) and Ti(Oi-Pr)$_4$ (520 mg, 1.83 mmol) in toluene (3 ml) was heated to 150° C. under microwave for 2 h. After cooling to rt, NaBH(OAc)$_3$ was added at rt and the resulting mixture was stirred for another 1 h, quenched with water (5 ml), filtered. The filtrate was diluted with EtOAc (300 ml), washed with brine (50 ml) and concentrated. The residue was purified by prep-TLC (PE/EtOAc=5/1) to give (1S)-tert-butyl 1-(2-(3-chloro-4-(dimethylcarbamoyl)phenylamino)propyl)-6-azaspiro[2.5]octane-6-carboxylate. LRMS m/z (M+H) 450.0 found, 450.2 required.

4-(1-((S or R)-6-azaspiro[2.5]octan-1-yl)propan-2-ylamino)-2-chloro-N,N-dimethylbenzamide To a solution of (1S)-tert-butyl 1-(2-(3-chloro-4-(dimethylcarbamoyl)phenylamino)propyl)-6-azaspiro[2.5]octane-6-carboxylate (96 mg, 0.214 mmol) in 6 ml of DCM was added TFA (1 ml). The reaction was stirred at room temperature for 1 h. The solvent was removed under reduced pressure and the residue was basified to pH=7-8 with sat. NaHCO$_3$. The mixture was extracted with DCM (50 ml×3), washed with brine (20 ml), dried over anhydrous Na$_2$SO$_4$ and concentrated to give 4-(1-((S or R)-6-azaspiro[2.5]octan-1-yl)propan-2-ylamino)-2-chloro-N,N-dimethylbenzamide. LRMS m/z (M+H) 350.1 found, 350.2 required.

2-chloro-N,N-dimethyl-4-(1-((S or R)-6-(1-phenylcyclobutanecarbonyl)-6-azaspiro[2.5]octan-1-yl)propan-2-ylamino)benzamide To a solution of 1-phenylcyclobutanecarboxylic acid (15 mg, 0.09 mmol) in DMF (0.3 ml) was added a solution of HATU (33 mg, 0.09 mmol) in DMF (0.3 ml) at room temperature, followed by addition of 4-(1-((S or R)-6-azaspiro[2.5]octan-1-yl)propan-2-ylamino)-2-chloro-N,N-dimethylbenzamide (25 mg, 0.07 mmol) and DIPEA (18 mg, 0.14 mmol) in DMF (0.4 ml) at room temperature. The resulting mixture was stirred overnight and directly purified by reverse phase chromotography (mobile phase: methanol/water (10 mM NH$_4$HCO$_3$)) to afford 2-chloro-N,N-dimethyl-4-(1-((S or R)-6-(1-phenylcyclobutanecarbonyl)-6-azaspiro[2.5]octan-1-yl)propan-2-ylamino)benzamide. LRMS m/z (M+H) 508.4 found, 508.3 required. Absolute stereochemistry not confirmed.

Example 6-1

2-chloro-N,N-dimethyl-4-(3-((R or S)-6-((R or S)-3,3,3-trifluoro-2-hydroxy-2-phenylpropanoyl)-6-azaspiro[2.5]octan-1-yl)propylamino)benzamide

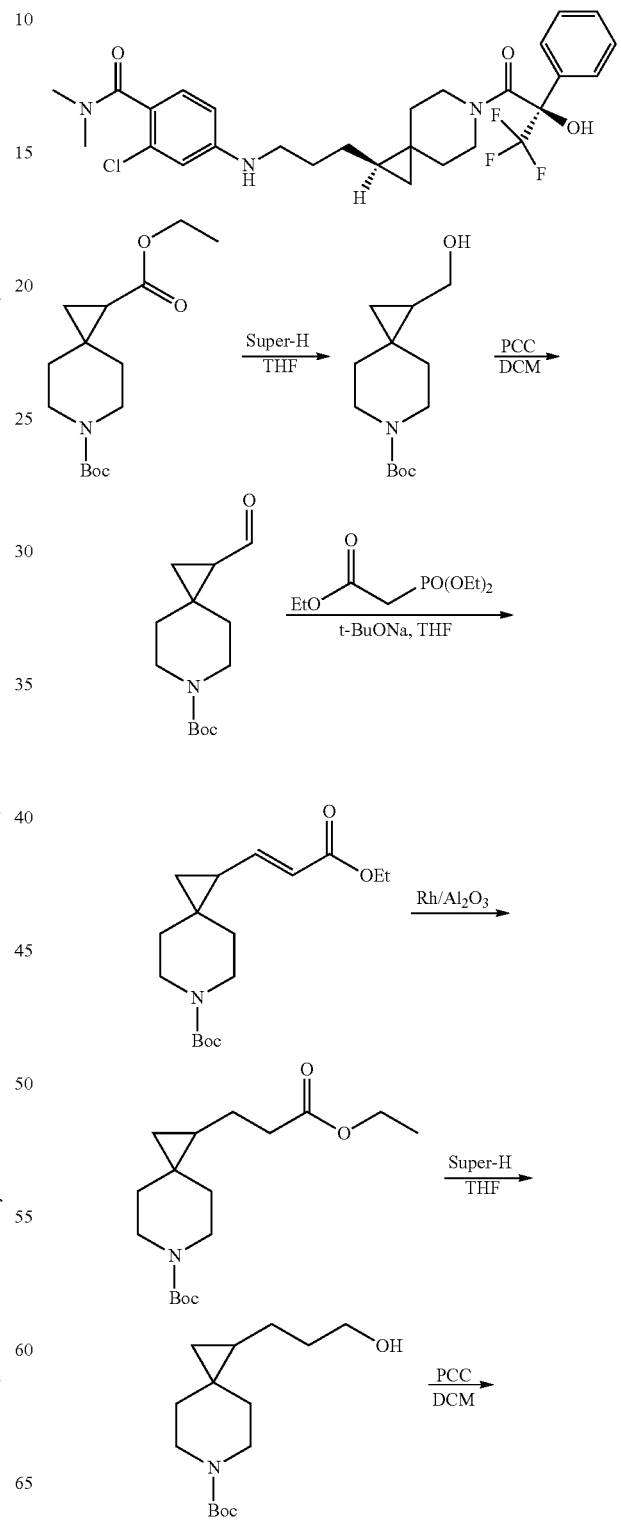

51
-continued

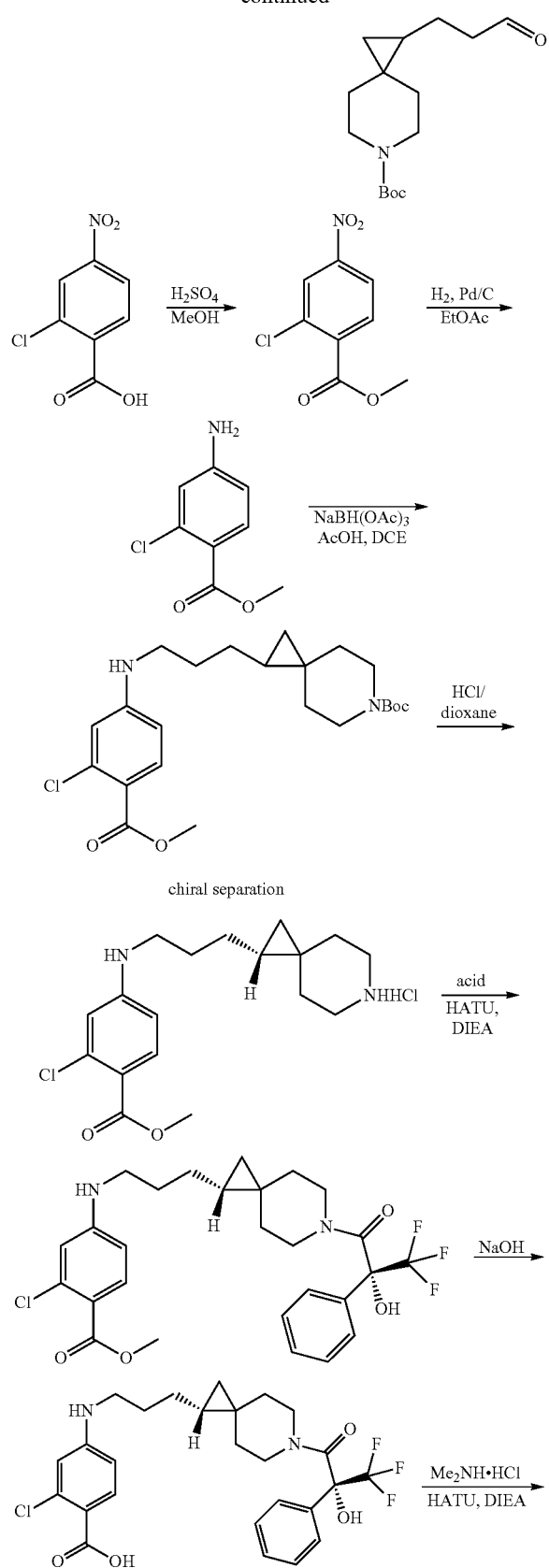

chiral separation

52
-continued

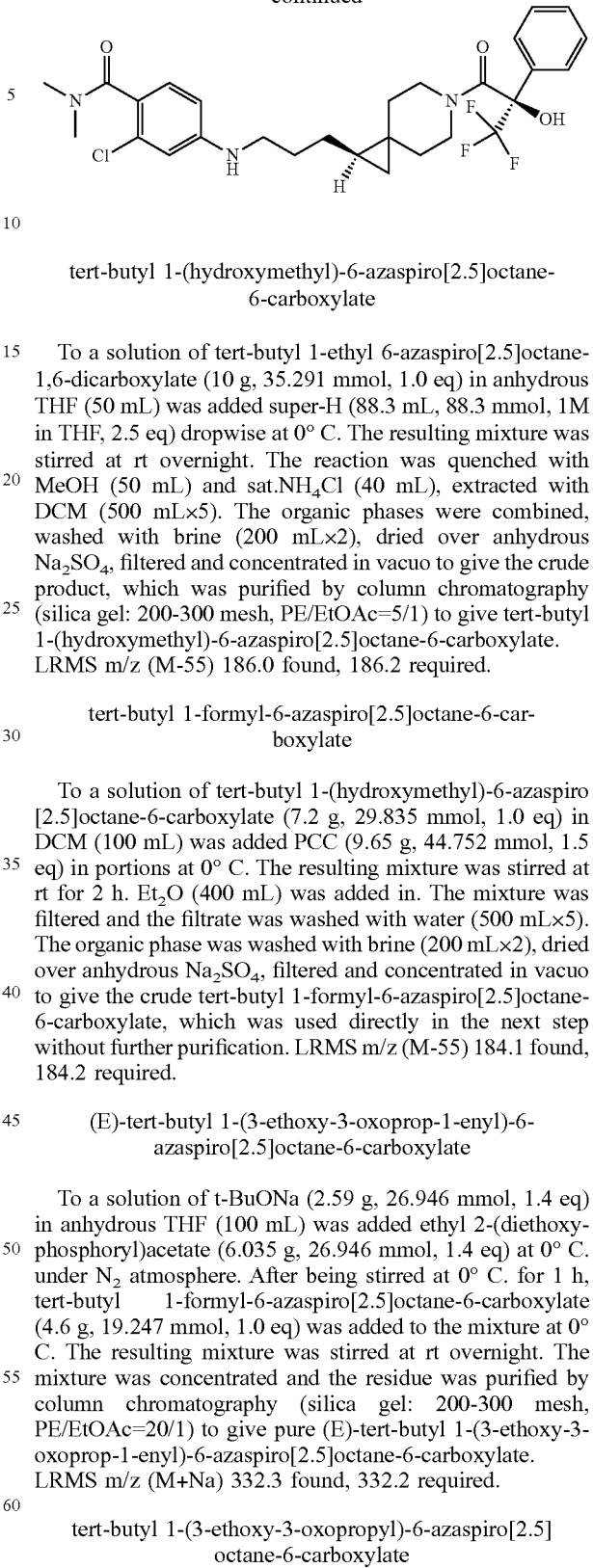

tert-butyl 1-(hydroxymethyl)-6-azaspiro[2.5]octane-6-carboxylate

To a solution of tert-butyl 1-ethyl 6-azaspiro[2.5]octane-1,6-dicarboxylate (10 g, 35.291 mmol, 1.0 eq) in anhydrous THF (50 mL) was added super-H (88.3 mL, 88.3 mmol, 1M in THF, 2.5 eq) dropwise at 0° C. The resulting mixture was stirred at rt overnight. The reaction was quenched with MeOH (50 mL) and sat.NH$_4$Cl (40 mL), extracted with DCM (500 mL×5). The organic phases were combined, washed with brine (200 mL×2), dried over anhydrous Na$_2$SO$_4$, filtered and concentrated in vacuo to give the crude product, which was purified by column chromatography (silica gel: 200-300 mesh, PE/EtOAc=5/1) to give tert-butyl 1-(hydroxymethyl)-6-azaspiro[2.5]octane-6-carboxylate. LRMS m/z (M-55) 186.0 found, 186.2 required.

tert-butyl 1-formyl-6-azaspiro[2.5]octane-6-carboxylate

To a solution of tert-butyl 1-(hydroxymethyl)-6-azaspiro[2.5]octane-6-carboxylate (7.2 g, 29.835 mmol, 1.0 eq) in DCM (100 mL) was added PCC (9.65 g, 44.752 mmol, 1.5 eq) in portions at 0° C. The resulting mixture was stirred at rt for 2 h. Et$_2$O (400 mL) was added in. The mixture was filtered and the filtrate was washed with water (500 mL×5). The organic phase was washed with brine (200 mL×2), dried over anhydrous Na$_2$SO$_4$, filtered and concentrated in vacuo to give the crude tert-butyl 1-formyl-6-azaspiro[2.5]octane-6-carboxylate, which was used directly in the next step without further purification. LRMS m/z (M-55) 184.1 found, 184.2 required.

(E)-tert-butyl 1-(3-ethoxy-3-oxoprop-1-enyl)-6-azaspiro[2.5]octane-6-carboxylate To a solution of t-BuONa (2.59 g, 26.946 mmol, 1.4 eq) in anhydrous THF (100 mL) was added ethyl 2-(diethoxyphosphoryl)acetate (6.035 g, 26.946 mmol, 1.4 eq) at 0° C. under N$_2$ atmosphere. After being stirred at 0° C. for 1 h, tert-butyl 1-formyl-6-azaspiro[2.5]octane-6-carboxylate (4.6 g, 19.247 mmol, 1.0 eq) was added to the mixture at 0° C. The resulting mixture was stirred at rt overnight. The mixture was concentrated and the residue was purified by column chromatography (silica gel: 200-300 mesh, PE/EtOAc=20/1) to give pure (E)-tert-butyl 1-(3-ethoxy-3-oxoprop-1-enyl)-6-azaspiro[2.5]octane-6-carboxylate. LRMS m/z (M+Na) 332.3 found, 332.2 required.

tert-butyl 1-(3-ethoxy-3-oxopropyl)-6-azaspiro[2.5]octane-6-carboxylate

A mixture of (E)-tert-butyl 1-(3-ethoxy-3-oxoprop-1-enyl)-6-azaspiro[2.5]octane-6-carboxylate (5.0 g, 16.181 mmol, 1.0 eq) and 5% Rh—Al$_2$O$_3$ (1.25 g) in EtOAc (100 mL) was stirred at rt overnight under H$_2$ balloon. The mixture was filtered and concentrated in vacuo to give crude tert-butyl 1-(3-ethoxy-3-oxopropyl)-6-azaspiro[2.5]octane-6-carboxylate, which was used directly in the next step without further purification. LRMS m/z (M-99) 212.2 found, 212.2 required.

tert-butyl 1-(3-hydroxypropyl)-6-azaspiro[2.5]octane-6-carboxylate

To a solution of tert-butyl 1-(3-ethoxy-3-oxopropyl)-6-azaspiro[2.5]octane-6-carboxylate (4.6 g, 14.791 mmol, 1.0 eq) in anhydrous THF (100 mL) was added super-Hydride (37 mL, 37 mmol, 1M in THF, 2.5 eq) in dropwise at 0° C. The resulting mixture was stirred at rt overnight and quenched with MeOH (80 mL) sat. $NH_4Cl$ (150 mL), extracted with DCM (100 mL×5). The organic phases were combined, washed with brine (100 mL×2), dried over anhydrous $Na_2SO_4$, filtered and concentrated in vacuo to give the crude product which was purified by column chromatography (silica gel: 200-300 mesh, PE/EtOAc=10/1) to give pure tert-butyl 1-(3-hydroxypropyl)-6-azaspiro[2.5]octane-6-carboxylate.

tert-butyl 1-(3-oxopropyl)-6-azaspiro[2.5]octane-6-carboxylate

To a solution of tert-butyl 1-(3-hydroxypropyl)-6-azaspiro[2.5]octane-6-carboxylate (3.0 g, 11.152 mmol, 1.0 eq) in DCM (80 mL) was added PCC (3.61 g, 16.729 mmol, 1.5 eq) in portions at 0° C. The resulting mixture was stirred at rt for 3 h. $Et_2O$ (400 mL) and diatomite (30 g) were added to the reaction mixture. The resulting mixture was stirred for 20 min, filtered and washed with water (100 mL). The organic phase was washed with brine (50 mL×2), dried over anhydrous $Na_2SO_4$, filtered and concentrated under reduced pressure to give the crude tert-butyl 1-(3-oxopropyl)-6-azaspiro[2.5]octane-6-carboxylate, which was used directly in the next step without further purification. LRMS m/z (M-55) 212.0 found, 212.2 required.

Methyl 2-chloro-4-nitrobenzoate

To a solution of 2-chloro-4-nitrobenzoic acid (3.0 g, 14.925 mmol, 1.0 eq) in MeOH (100 mL) was added $conc.H_2SO_4$ (10 mL) in dropwise. The mixture was refluxed for 6 h. Then solvent was removed in vacuo. $Sat.NaHCO_3$ (100 mL) was added and the reaction mixture was extracted with DCM (100 mL×5). The organic phases were combined, washed with brine (200 mL), dried over anhydrous $Na_2SO_4$, filtered and concentrated in vacuo to give the crude product which was purified by column chromatography (silica gel: 200-300 mesh, PE/DCM=8/1) to give pure methyl 2-chloro-4-nitrobenzoate.

Methyl 4-amino-2-chlorobenzoate

A mixture of methyl 2-chloro-4-nitrobenzoate (2.52 g, 11.721 mmol, 1.0 eq) and 5% Pd/C (252 mg) in EtOAc (100 mL) was stirred at rt for 2 h under $H_2$ atmosphere. The mixture was filtered and the filtrate was concentrated in vacuo to afford the crude product methyl 4-amino-2-chlorobenzoate. LRMS m/z (M+H) 186.1 found, 186.0 required.

tert-butyl 1-(3-(3-chloro-4-(methoxycarbonyl)phenylamino)propyl)-6-azaspiro[2.5]octane-6-carboxylate A mixture of methyl 4-amino-2-chlorobenzoate (1.73 g, 9.363 mmol, 1.0 eq), tert-butyl 1-(3-oxopropyl)-6-azaspiro [2.5]octane-6-carboxylate (2.5 g, 9.363 mmol, 1.0 eq), $NaBH(OAc)_3$ (4.96 g, 23.408 mmol, 2.5 eq) and HOAc (1 drop) in DCE (50 mL) was stirred at 35° C. overnight. The reaction was quenched with water (50 mL), extracted with DCM (50 mL×5). The organic phases were combined, washed with brine (100 mL), dried over anhydrous $Na_2SO_4$, filtered and concentrated in vacuo to afford the crude product which was purified by column chromatography (silica gel: 200-300 mesh, PE/DCM=20/1) to give tert-butyl 1-(3-(3-chloro-4-(methoxycarbonyl)phenylamino)propyl)-6-azaspiro[2.5]octane-6-carboxylate. LRMS m/z (M-99) 337.2 found, 337.2 required. The racemic product was resolved by Chiral HPLC (column: AS-H (250*4.6 mm 5 um); Mobile phase: SFC—$CO_2$:MeOH (0.1%DEA)=75:25; flow: 3 ml/min; temperature: 39.8° C.) to afford (R or S)-tert-butyl 1-(3-(3-chloro-4-(methoxycarbonyl)phenylamino)propyl)-6-azaspiro[2.5]octane-6-carboxylate (RT=4.2 min) and (S or R)-tert-butyl 1-(3-(3-chloro-4-(methoxycarbonyl)phenylamino)propyl)-6-azaspiro[2.5]octane-6-carboxylate (RT=5.53 min). The absolute stereochemistry was not confirmed.

(R or S)-methyl 4-(3-(6-azaspiro[2.5]octan-1-yl)propylamino)-2-chlorobenzoate hydrochloride A solution of (R or S)-tert-butyl 1-(3-(3-chloro-4-(methoxycarbonyl)phenylamino)propyl)-6-azaspiro[2.5]octane-6-carboxylate (peak 1) (500 mg, 1.147 mmol, 1.0 eq) in 4M HCl/1,4-dioxane (15 mL) was stirred at rt for 0.5 h. The mixture was concentrated in vacuo to afford (R or S)-methyl 4-(3-(6-azaspiro[2.5]octan-1-yl)propylamino)-2-chlorobenzoate hydrochloride. LRMS m/z (M+H) 337.2 found, 337.2 required.

Methyl 2-chloro-4-(3-((R or S)-6-((R or S)-3,3,3-trifluoro-2-hydroxy-2-phenylpropanoyl)-6-azaspiro [2.5]octan-1-yl)propylamino)benzoate A mixture of (R or S)-methyl 4-(3-(6-azaspiro[2.5]octan-1-yl)propylamino)-2-chlorobenzoate hydrochloride (200 mg, 0.5952 mmol, 1.0 eq), (R or S)-3,3,3-trifluoro-2-hydroxy-2-phenylpropanoic acid (131 mg, 0.5952 mmol, 1.0 eq), HATU (339 mg, 0.8929 mmol, 1.5 eq) and DIEA (230 mg, 1.7857 mmol, 3.0 eq) in anhydrous THF (4 mL) was stirred at rt overnight. The mixture was purified directly by reverse phase chromotography (Mobile phase: methanol/water (10 mM $NH_4HCO_3$)) to give methyl 2-chloro-4-(3-((R or S)-6-((R or S)-3,3,3-trifluoro-2-hydroxy-2-phenylpropanoyl)-6-azaspiro[2.5]octan-1-yl)propylamino)benzoate. LRMS m/z (M+H) 539.2 found, 539.2 required.

2-chloro-4-(3-((R or S)-6-((R or S)-3,3,3-trifluoro-2-hydroxy-2-phenylpropanoyl)-6-azaspiro[2.5]octan-1-yl)propylamino)benzoic Acid To a solution of methyl 2-chloro-4-(3-((R or S)-6-((R or S)-3,3,3-trifluoro-2-hydroxy-2-phenylpropanoyl)-6-azaspiro[2.5]octan-1-yl)propylamino)benzoate (120 mg, 0.223 mmol, 1.0 eq) in THF (3 mL) was added NaOH (3 mL, 1.35 mmol, 0.45M in water). The resulting mixture was stirred at rt overnight. The mixture was concentrated in vacuo, acidified with 1N HCl to pH=3 and extracted with DCM (10 mL×5). The organic phases were combined, washed with brine (20 mL), dried over anhydrous $Na_2SO_4$, filtered and concentrated in vacuo to give 2-chloro-4-(3-((R or S)-6-((R or S)-3,3,3-trifluoro-2-hydroxy-2-phenylpropanoyl)-6-azaspiro[2.5]octan-1-yl)propylamino)benzoic acid. LRMS m/z (M+Na) 547.0 found, 547.2 required.

2-chloro-N,N-dimethyl-4-(3-((R or S)-6-((R or S)-3,3,3-trifluoro-2-hydroxy-2-phenylpropanoyl)-6-azaspiro[2.5]octan-1-yl)propylamino)benzamide A mixture of 2-chloro-4-(3-((R or S)-6-((R or S)-3,3,3-trifluoro-2-hydroxy-2-phenylpropanoyl)-6-azaspiro[2.5]octan-1-yl)propylamino)benzoic acid (40 mg, 0.0763 mmol, 1.0 eq), dimethylamine hydrochloride (8 mg, 0.1 mmol, 1.2 eq), HATU (43.5 mg, 0.1145 mmol, 1.5 eq) and DIEA (29.5 mg, 0.229 mmol, 3.0 eq) in anhydrous THF (2.0 mL) was stirred at rt overnight. The mixture was purified directly by prep-HPLC (mobile phase: acetonitrile/water (10 mM NH₄HCO₃)) to give 2-chloro-N,N-dimethyl-4-(3-((R or S)-6-((R or S)-3,3,3-trifluoro-2-hydroxy-2-phenylpropanoyl)-6-azaspiro[2.5]octan-1-yl)propylamino)benzamide. LRMS m/z (M+H) 552.1 found, 552.2 required.

Using the same procedure described in example 6-1, but replacing propan-2-amine with the appropriate amines in the last step and replacing (R or S)-3,3,3-trifluoro-2-hydroxy-2-phenylpropanoic acid with the appropriate acid in the twelfth step, the compounds in the table below were prepared.

| Example | Structure | IUPAC Name | LRMS, found [M + H]+ |
|---|---|---|---|
| 6-2 | 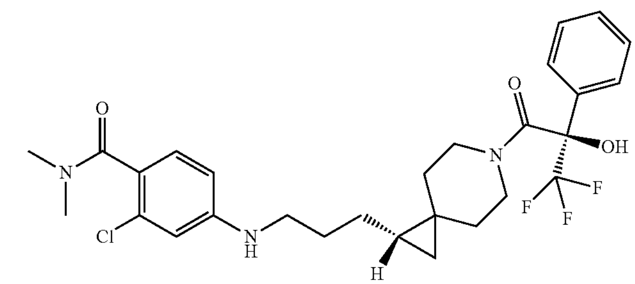 [SMILES: CN(C)C(=O)c1ccc(NCCC[C@H]2CC23CCN(C(=O)[C@](O)(c2ccccc2)C(F)(F)F)CC3)cc1Cl] | 2-chloro-N,N-dimethyl-4-(3-((S or R)-6-((R or S)-3,3,3-trifluoro-2-hydroxy-2-phenylpropanoyl)-6-azaspiro[2.5]octan-1-yl)propylamino)benzamide | 552.2 |
| 6-3 | 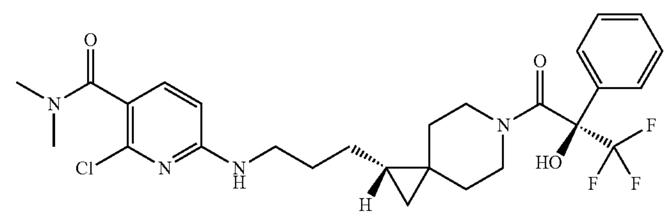 [SMILES: CN(C)C(=O)c1ccc(NCCC[C@H]2CC23CCN(C(=O)[C@](O)(c2ccccc2)C(F)(F)F)CC3)nc1Cl] | 2-chloro-N,N-dimethyl-6-(3-((S or R)-6-((R or S)-3,3,3-trifluoro-2-hydroxy-2-phenylpropanoyl)-6-azaspiro[2.5]octan-1-yl)propylamino)nicotinamide | 553.2 |
| 6-4 | 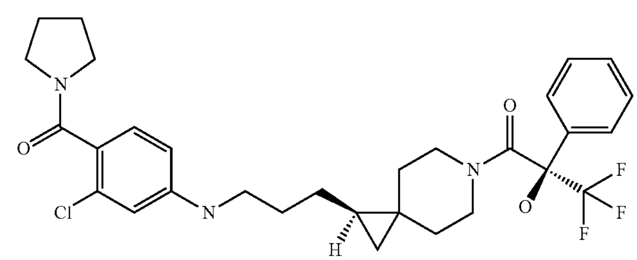 [SMILES: O=C(c1ccc(NCCC[C@@H]2CC23CCN(C(=O)[C@](O)(c2ccccc2)C(F)(F)F)CC3)cc1Cl)N1CCCC1] | (R or S)-1-((R or S)-1-(3-(3-chloro-4-(pyrrolidine-1-carbonyl)phenylamino)propyl)-6-azaspiro[2.5]octan-6-yl)-3,3,3-trifluoro-2-hydroxy-2-phenylpropan-1-one | 578.1 |
| 6-5 | 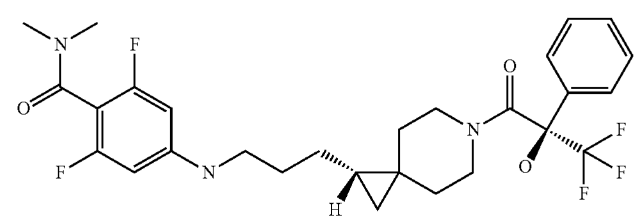 [SMILES: CN(C)C(=O)c1c(F)cc(NCCC[C@H]2CC23CCN(C(=O)[C@](O)(c2ccccc2)C(F)(F)F)CC3)cc1F] | 2,6-difluoro-N,N-dimethyl-4-(3-((S or R)-6-((R or S)-3,3,3-trifluoro-2-hydroxy-2-phenylpropanoyl)-6-azaspiro[2.5]octan-1-yl)propylamino)benzamide | 554.1 |
| 6-6 | 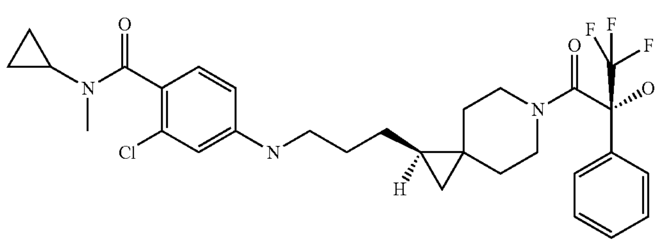 [SMILES: CN(C(=O)c1ccc(NCCC[C@@H]2CC23CCN(C(=O)[C@](O)(c2ccccc2)C(F)(F)F)CC3)cc1Cl)C1CC1] | 2-chloro-N-cyclopropyl-N-methyl-4-(3-((R or S)-6-((R or S)-3,3,3-trifluoro-2-hydroxy-2-phenylpropanoyl)-6-azaspiro[2.5]octan-1-yl)propylamino)benzamide | 578.1 |

| Example | Structure | IUPAC Name | LRMS, found [M + H]+ |
|---|---|---|---|
| 6-7 | 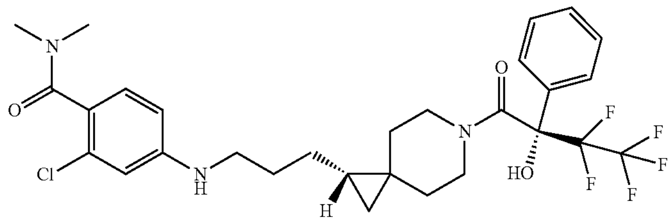 [SMILES: CN(C)C(=O)c1ccc(NCCC[C@H]2CC23CCN(C(=O)[C@@](O)(c2ccccc2)C(F)(F)C(F)(F)F)CC3)cc1Cl] | 2-chloro-N,N-dimethyl-4-(3-((S or R)-6-((S or R)-3,3,4,4,4-pentafluoro-2-hydroxy-2-phenylbutanoyl)-6-azaspiro[2.5]octan-1-yl)propylamino)benzamide | 602.1 |
| 6-8 | 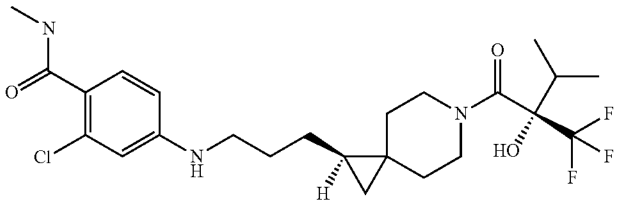 [SMILES: CNC(=O)c1ccc(NCCC[C@@H]2CC23CCN(C(=O)[C@@](O)(C(C)C)C(F)(F)F)CC3)cc1Cl] | 2-chloro-4-(3-((R or S)-6-((S or R)-2-hydroxy-3-methyl-2-(trifluoromethyl)butanoyl)-6-azaspiro[2.5]octan-1-yl)propylamino)-N-methylbenzamide | 504.2 |
| 6-9 | 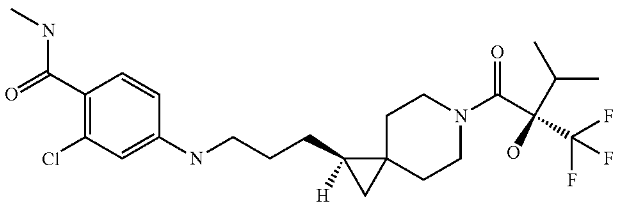 [SMILES: CNC(=O)c1ccc(NCCC[C@@H]2CC23CCN(C(=O)[C@](O)(C(C)C)C(F)(F)F)CC3)cc1Cl] | 2-chloro-4-(3-((R or S)-6-((R or S)-2-hydroxy-3-methyl-2-(trifluoromethyl)butanoyl)-6-azaspiro[2.5]octan-1-yl)propylamino)-N-methylbenzamide | 504.2 |

Example 7-1

2-chloro-N,N-dimethyl-4-(methyl(3-((R or S)-6-((R or S)-3,3,3-trifluoro-2-hydroxy-2-phenylpropanoyl)-6-azaspiro[2.5]octan-1-yl)propyl)amino)benzamide

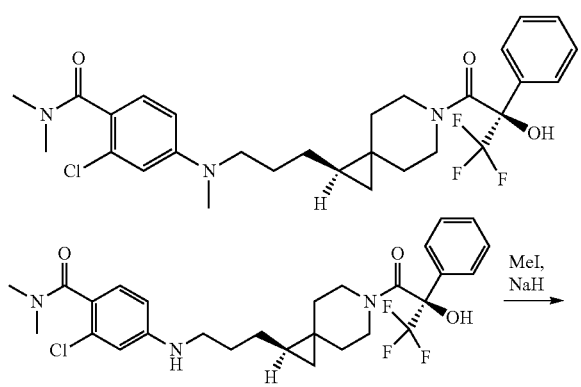

2-chloro-N,N-dimethyl-4-(methyl(3-((R or S)-6-((R or S)-3,3,3-trifluoro-2-hydroxy-2-phenylpropanoyl)-6-azaspiro[2.5]octan-1-yl)propyl)amino)benzamide To a solution of 2-chloro-N,N-dimethyl-4-(3-((R or S)-6-((R or S)-3,3,3-trifluoro-2-hydroxy-2-phenylpropanoyl)-6-azaspiro[2.5]octan-1-yl)propylamino)benzamide (20 mg, 0.036 mmol, 1.0 eq) in anhydrous THF (2 mL) was added NaH (4 mg, 0.1 mmol, 60% in oil) at 0° C. The mixture was stirred at rt for 0.5 h before MeI (5 mg, 0.034 mmol) was injected in. The resulting mixture was stirred at rt overnight, quenched with sat. NH$_4$Cl (1 mL) and extracted with DCM (5 mL×3). The organic phases were combined, washed with brine (1 mL), dried over anhydrous Na$_2$SO$_4$, filtered and concentrated and purified by prep-TLC to afford 2-chloro-N,N-dimethyl-4-(methyl(3-((R or S)-6-((R or S)-3,3,3-trifluoro-2-hydroxy-2-phenylprop azaspiro[2.5]octan-1-yl)propyl)amino)benzamide. LRMS m/z (M+H) 566.2 found, 566.2 required.

Example 8-1

(S or R)-2-chloro-N,N-dimethyl-4-(2-(6-(1-phenylcyclopentanecarbonyl)-6-azaspiro[2.5]octan-1-yl)ethylamino)benzamide

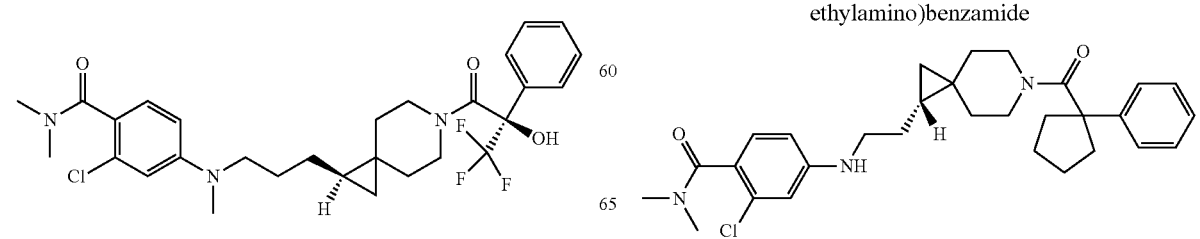

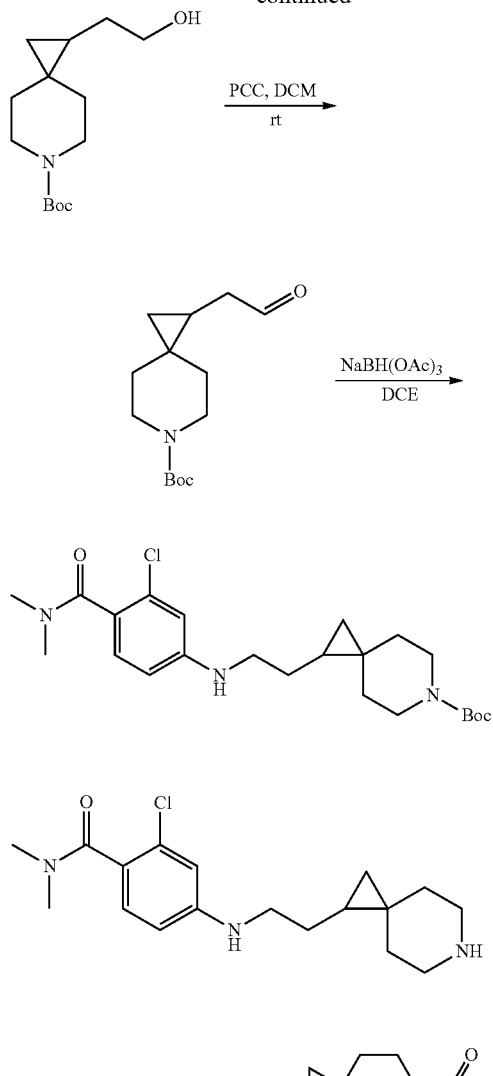

tert-butyl 1-(2-oxoethyl)-6-azaspiro[2.5]octane-6-carboxylate

A mixture of tert-butyl 1-(2-hydroxyethyl)-6-azaspiro[2.5]octane-6-carboxylate (1.5 g, 5.88 mmol) and PCC (3793 mg, 17.64 mmol) in dichloromethane (30 mL) was stirred at rt for 2 h. Then the mixture was diluted with dichloromethane (300 mL), filtered off through a celite pad and the filtrate was concentrated to give crude product which was purified by column chromatography (silica gel: 200-300 mesh, PE/EtOAc=5/1, v/v) to afford tert-butyl 1-(2-oxo-ethyl)-6-azaspiro[2.5]octane-6-carboxylate. LRMS m/z (M-55) 198.1 found, 198.2 required.

tert-butyl 1-(2-(3-chloro-4-(dimethylcarbamoyl)phenylamino)ethyl)-6-azaspiro[2.5]octane-6-carboxylate A solution of tert-butyl 1-(2-oxoethyl)-6-azaspiro[2.5]octane-6-carboxylate (1.2 g, 4.74 mmol), 4-amino-2-chloro-N,N-dimethylbenzamide (1408 mg, 7.11 mmol), NaBH(AcO)₃ (3015 mg, 14.22 mmol) and AcOH (0.5 mL) in DCE (30 mL) was stirred for 2 h at rt under nitrogen atmosphere. The mixture was concentrated, diluted with dichloromethane (500 mL), washed with saturated NaHCO₃ (50 mL*2), brine (50 mL), dried over anhydrous Na₂SO₄, filtered and concentrated to afford crude product tert-butyl 1-(2-(3-chloro-4-(dimethylcarbamoyl)phenylamino)ethyl)-6-azaspiro[2.5]octane-6-carboxylate. LRMS m/z (M-55) 380.2 found, 380.2 required.

4-(2-(6-azaspiro[2.5]octan-1-yl)ethylamino)-2-chloro-N,N-dimethylbenzamide

A solution of tert-butyl 1-(2-(3-chloro-4-(dimethylcarbamoyl)phenylamino)ethyl)-6-azaspiro[2.5]octane-6-carboxylate (1.5 g, 3.45 mmol) and TFA (3 mL) in DCM (15 mL) was stirred for 2 h at rt. The mixture was basified with saturated NaHCO₃ to pH=9.0, extracted with DCM/CH₃OH (10/1, 300 mL*2) and washed with brine (20 mL), and dried over anhydrous Na₂SO₄, filtered and concentrated to afford 4-(2-(6-azaspiro[2.5]octan-1-yl)ethylamino)-2-chloro-N,N-dimethylbenzamide. LRMS m/z (M+H) 336.3 found, 336.2 required.

(S or R)-2-chloro-N,N-dimethyl-4-(2-(6-(1-phenylcyclopentanecarbonyl)-6-azaspiro[2.5]octan-1-yl)ethylamino)benzamide A mixture of 4-(2-(6-azaspiro[2.5]octan-1-yl)ethylamino)-2-chloro-N,N-dimethylbenzamide (30 mg, 0.09 mmol), 1-phenylcyclopentanecarboxylic acid (21 mg, 0.14 mmol), HATU (52 mg, 0.14 mmol) and DIPEA (18 mg, 0.14 mmol) in DMF (1 mL) was stirred overnight at rt. The residue was purified by reverse phase HPLC (mobile phase: methanol/water (10 mM NH₄HCO₃)) to afford racemic product which was resolved by Chiral-HPLC (column: AS-H (250*4.6 mm 5 um); mobile phase: SCF—CO2/EtOH (0.1% DEA)=2.1/0.9; flow: 3 ml/min; temperature: 40.1° C.) to give (R or S)-2-chloro-N,N-dimethyl-4-(2-(6-(1-phenylcyclopentanecarbonyl)-6-azaspiro[2.5]octan-1-yl)ethylamino)benzamide (RT=4.18 min) and (S or R)-2-chloro-N,N-dimethyl-4-(2-(6-(1-phenylcyclopentanecarbonyl)-6-azaspiro[2.5]octan-1-yl)ethylamino)benzamide (RT=4.98 min). LRMS m/z (M+H) 508.1 found, 508.2 required.

Using the same procedure described in example 8-1, but replacing tert-butyl 1-(2-hydroxyethyl)-6-azaspiro[2.5]octane-6-carboxylate with tert-butyl 4-((1R,2S or 1S,2R)-2-(hydroxymethyl)cyclopropyl)piperidine-1-carboxylate or tert-butyl 4-((1S,2S or 1R,2R)-2-(hydroxymethyl)cyclopropyl)piperidine-1-carboxylate in the first step and replacing 1-phenylcyclopentanecarboxylic acid with (R or S)-3,3,3-trifluoro-2-hydroxy-2-phenylpropanoic acid in the last step the compounds in the table below were prepared.

| Example | Structure | IUPAC Name | LRMS, found [M + H]+ |
|---|---|---|---|
| 8-2 | 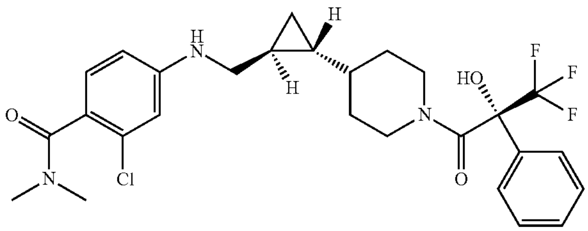 [SMILES: CN(C)C(=O)c1ccc(NC[C@H]2C[C@@H]2C2CCN(C(=O)[C@](O)(c3ccccc3)C(F)(F)F)CC2)cc1Cl] | 2-chloro-N,N-dimethyl-4-(((1S,2R or 1R,2S)-2-(1-((R or S)-3,3,3-trifluoro-2-hydroxy-2-phenylpropanoyl)piperidin-4-yl)cyclopropyl)methylamino)benzamide | 538.2 |
| 8-3 | 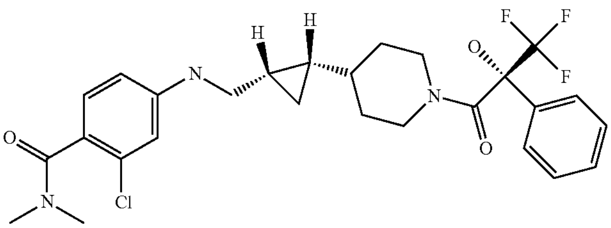 [SMILES: CN(C)C(=O)c1ccc(NC[C@H]2C[C@H]2C2CCN(C(=O)[C@](O)(c3ccccc3)C(F)(F)F)CC2)cc1Cl] | 2-chloro-N,N-dimethyl-4-(((1S,2S or 1R,2R)-2-(1-((R or S)-3,3,3-trifluoro-2-hydroxy-2-phenylpropanoyl)piperidin-4-yl)cyclopropyl)methylamino)benzamide | 538.1 |

Example 9-1

(S or R)-2-chloro-N,N-dimethyl-4-(methyl(2-(6-(2-methyl-2-phenylpropanoyl)-6-azaspiro[2.5]octan-1-yl)ethyl)amino)benzamide

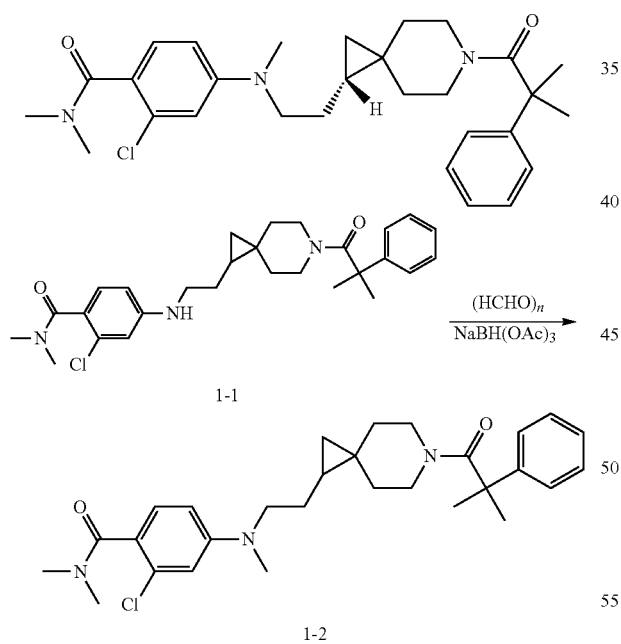

(S or R)-2-chloro-N,N-dimethyl-4-(methyl(2-(6-(2-methyl-2-phenylpropanoyl)-6-azaspiro[2.5]octan-1-yl)ethyl)amino)benzamide To a well stirred solution of 2-chloro-N,N-dimethyl-4-(2-(6-(2-methyl-2-phenylpropanoyl)-6-azaspiro[2.5]octan-1-yl)ethylamino)benzamide (40.0 mg, 0.08 mmol), paraformaldehyde (28.0 mg, 0.87 mmol) in 6 mL of 1,2-DCE was added NaBH(OAc)₃ (68 mg, 0.32 mmol). The mixture was stirred overnight, diluted with DCM (100 ml), washed with water (30 ml×2), brine (30 ml), dried and concentrated to give crude product, which was purified by Prep-TLC (silica gel, PE/EtOAc=1/1) to afford 2-chloro-N,N-dimethyl-4-(methyl(2-(6-(2-methyl-2-phenylpropanoyl)-6-azaspiro[2.5]octan-1-yl)ethyl)amino)benzamide. LRMS m/z (M+H) 495.9 found, 496.3 required. The racemic product (30 mg) was resolved by Chiral HPLC (column: AD-H (250*4.6 mm 5 um); mobile phase: SCF—CO2:MeOH (0.1% DEA)=70:30; flow: 3 ml/min; temperature: 40.1° C.) to afford (R or S)-2-chloro-N,N-dimethyl-4-(methyl(2-(6-(2-methyl-2-phenylpropanoyl)-6-azaspiro[2.5]octan-1-yl)ethyl)amino)benzamide (RT=4.6 min) and (S or R)-2-chloro-N,N-dimethyl-4-(methyl(2-(6-(2-methyl-2-phenylpropanoyl)-6-azaspiro[2.5]octan-1-yl)ethyl)amino)benzamide (RT=7.03 min).

Example 10-1

2-chloro-N,N-dimethyl-4-(3-((R or S)-3,3,3-trifluoro-2-hydroxy-2-(3-methoxyphenyl)propanoyl)-3-azaspiro[5.5]undecan-9-ylamino)benzamide

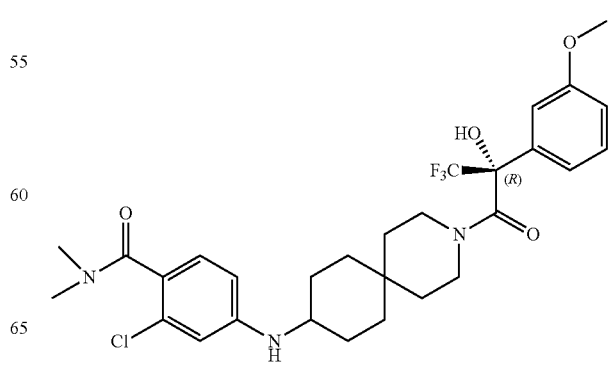

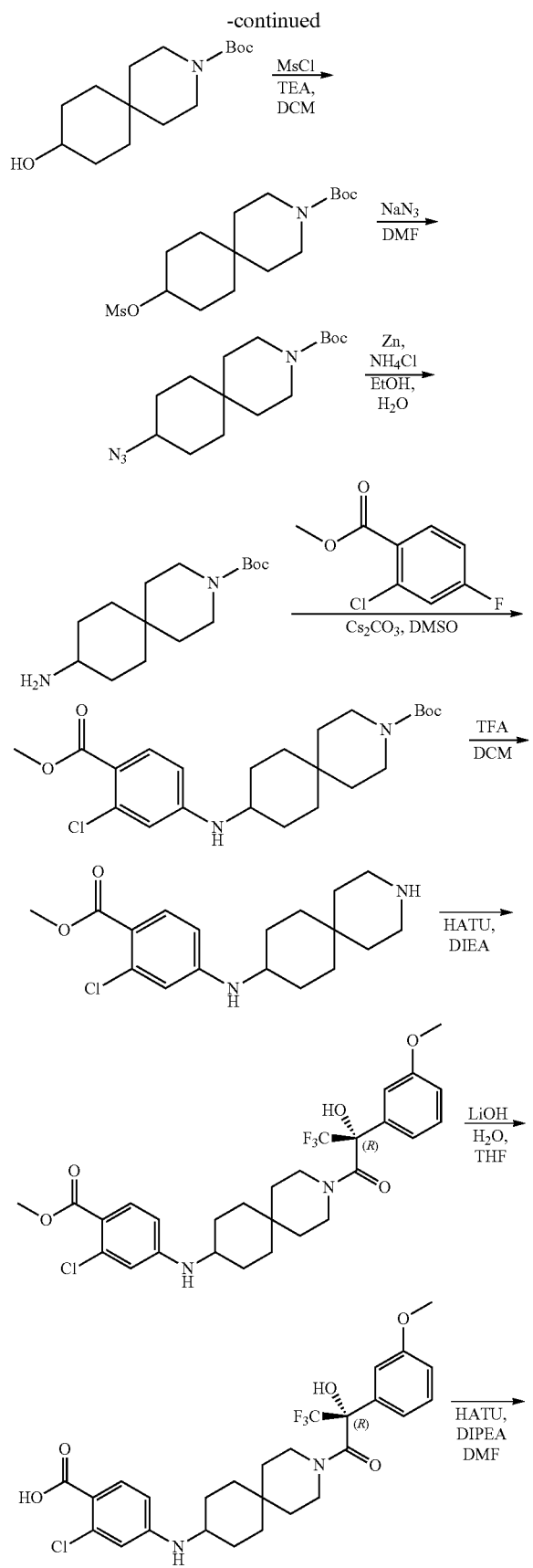

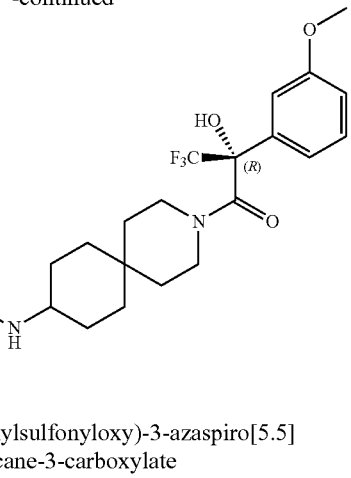

tert-butyl 9-(methylsulfonyloxy)-3-azaspiro[5.5]
undecane-3-carboxylate

To a solution of tert-butyl 9-hydroxy-3-azaspiro[5.5]undecane-3-carboxylate (200 mg, 0.74 mmol, 1.0 eq) and TEA (150 mg, 1.48 mmol, 2.0 eq) in DCM (6 ml) at 0° C. under $N_2$ was added MsCl (102 mg, 0.89 mmol, 1.2 eq). Then the mixture was stirred at room temperature for 1.5 h. LC-MS showed all SM consumed. The reaction was concentrated and 10 ml of sat. $NaHCO_3$ was added. It was extracted with DCM (20 ml×3). The combined organic phase was washed with brine (20 mL), dried ($Na_2SO_4$) and concentrated to give tert-butyl 9-(methylsulfonyloxy)-3-azaspiro[5.5]undecane-3-carboxylate. LRMS m/z (M-55), 292.1 found, 292.18 required.

tert-butyl 9-azido-3-azaspiro[5.5]undecane-3-carboxylate

A mixture of tert-butyl 9-(methylsulfonyloxy)-3-azaspiro[5.5]undecane-3-carboxylate (251 mg, 0.72 mmol, 1.0 eq) and $NaN_3$ (140 mg, 2.16 mmol, 3.0 eq) in DMF (5 mL) was heated to 80° C. overnight. After being cooled to room temperature, the mixture was diluted with EtOAc (50 mL), washed with water (10 mL×2), brine (10 mL), dried ($Na_2SO_4$) and concentrated. The residue was purified by column chromatography (silica gel, PE/EtOAc=5/1 to 1/1) to give tert-butyl 9-azido-3-azaspiro[5.5]undecane-3-carboxylate. LRMS m/z (M-55), 239.1 found, 239.2 required.

tert-butyl 9-amino-3-azaspiro[5.5]undecane-3-carboxylate

A mixture of tert-butyl 9-azido-3-azaspiro[5.5]undecane-3-carboxylate (200 mg, 0.68 mmol, 1.0 eq), Zn (134 mg, 2.04 mmol, 3.0 eq) and $NH_4Cl$ (108 mg, 2.04 mmol, 3.0 eq) in EtOH (15 ml) and water (5 mL) was heated to 70° C. for 3 h. After being cooled to room temperature, the mixture was filtered through a pad of celite and the filtrate was concentrated under reduced pressure to give tert-butyl 9-amino-3-azaspiro[5.5]undecane-3-carboxylate. LRMS m/z (M+H) 269.2 found, 269.2 required.

tert-butyl 9-(3-chloro-4-(methoxycarbonyl)phenylamino)-3-azaspiro[5.5]undecane-3-carboxylate A mixture of tert-butyl 9-amino-3-azaspiro[5.5]undecane-3-carboxylate (52 mg, 0.19 mmol, 1.0 eq), methyl 2-chloro-4-fluorobenzoate (44 mg, 0.23 mmol, 1.2 eq) and $Cs_2CO_3$ (186 mg, 0.57 mmol, 3.0 eq) in DMSO (5 mL) was heated to 120° C. overnight. After being cooled to room temperature, the mixture was diluted with EtOAc (50 mL), washed with water (10 mL×2), brine (10 mL), dried ($Na_2SO_4$) and concentrated. The residue was purified by reverse phase HPLC (mobile phase: MeOH/water (10 mmol $NH_4HCO_3$)) to give tert-butyl 9-(3-chloro-4-(methoxycarbonyl)phenylamino)-3-azaspiro[5.5]undecane-3-carboxylate. LRMS m/z (M+H), 437.1 found, 437.2 required.

methyl 4-(3-azaspiro[5.5]undecan-9-ylamino)-2-chlorobenzoate

To a solution of tert-butyl 9-(3-chloro-4-(methoxycarbonyl)phenylamino)-3-azaspiro[5.5]undecane-3-carboxylate (21 mg, 0.048 mmol, 1.0 eq) in DCM (2 ml) was added TFA (0.5 ml) at 0° C. The mixture was stirred at room temperature for 2 h. LC-MS showed all SM consumed. The reaction was concentrated and 10 ml of sat. $NaHCO_3$ was added. It was extracted with DCM (20 ml×3). The combined organic phase was washed with brine (20 mL), dried ($Na_2SO_4$) and concentrated to give methyl 4-(3-azaspiro[5.5]undecan-9-ylamino)-2-chlorobenzoate. LRMS m/z (M+H), 337.1 found, 337.2 required.

methyl 2-chloro-4-(3-((R or S)-3,3,3-trifluoro-2-hydroxy-2-(3-methoxyphenyl)propanoyl)-3-azaspiro[5.5]undecan-9-ylamino)benzoate A mixture of methyl 4-(3-azaspiro[5.5]undecan-9-ylamino)-2-chlorobenzoate (10 mg, 0.03 mmol, 1.0 eq), HATU (14 mg, 0.035 mmol, 1.2 eq), DIPEA (8 mg, 0.06 mmol, 2 eq) and (R or S)-3,3,3-trifluoro-2-hydroxy-2-(3-methoxyphenyl)propanoic acid (11 mg, 0.045 mmol, 1.5 eq) in DMF (1 ml) was stirred at room temperature. After being stirred for 3 h, the mixture was diluted with EtOAc (40 ml), washed with water (10 ml×3), brine (10 ml) and dried over anhydrous $Na_2SO_4$. The solvent was removed under reduced pressure and the residue was purified by prep-TLC (PE/EtOAc=1/1) to give methyl 2-chloro-4-(3-((R or S)-3,3,3-trifluoro-2-hydroxy-2-(3-methoxyphenyl)propanoyl)-3-azaspiro[5.5]undecan-9-ylamino)benzoate. LRMS m/z (M+H) 569.2, found, 569.2 required.

2-chloro-4-(3-((R or S)-3,3,3-trifluoro-2-hydroxy-2-(3-methoxyphenyl)propanoyl)-3-azaspiro[5.5]undecan-9-ylamino)benzoic Acid A mixture of methyl 2-chloro-4-(3-((R or S)-3,3,3-trifluoro-2-hydroxy-2-(3-methoxyphenyl)propanoyl)-3-azaspiro[5.5]undecan-9-ylamino)benzoate (9 mg, 0.016 mmol, 1.0 eq) and 1M LiOH (2 mL) in THF (2 mL) was stirred at room temperature overnight. Then Conc. HCl was added to adjust pH=3.0. The mixture was extracted with EtOAc (50 mL), washed with water (10 mL×2), brine (10 mL), dried ($Na_2SO_4$) and concentrated to give 2-chloro-4-(3-((R or S)-3,3,3-trifluoro-2-hydroxy-2-(3-methoxyphenyl)propanoyl)-3-azaspiro[5.5]undecan-9-ylamino)benzoic acid. LRMS m/z (M+H), 555.0 found, 555.19 required.

2-chloro-N,N-dimethyl-4-(3-((R or S)-3,3,3-trifluoro-2-hydroxy-2-(3-methoxyphenyl)propanoyl)-3-azaspiro[5.5]undecan-9-ylamino)benzamide A mixture of 2-chloro-4-(3-((R or S)-3,3,3-trifluoro-2-hydroxy-2-(3-methoxyphenyl)propanoyl)-3-azaspiro[5.5]undecan-9-ylamino)benzoic acid (8 mg, 0.014 mmol, 1.0 eq), HATU (8 mg, 0.022 mmol, 1.5 eq), DIPEA (6 mg, 0.042 mmol, 3 eq) and dimethylamine hydrochloride (3 mg, 0.029 mmol, 2 eq) in DMF (1 ml) was stirred at room temperature. After being stirred for 3 h, the mixture was diluted with EtOAc (40 ml), washed with water (10 ml×3), brine (10 ml) and dried over anhydrous $Na_2SO_4$. The solvent was removed under reduced pressure and the residue was purified by prep-TLC (PE/EtOAc=1/1) to give 2-chloro-N,N-dimethyl-4-(3-((R or S)-3,3,3-trifluoro-2-hydroxy-2-(3-methoxyphenyl)propanoyl)-3-azaspiro[5.5]undecan-9-ylamino)benzamide. LRMS m/z (M+H) 582.1, found, 582.2 required.

Example 11-1

2-chloro-N,N-dimethyl-4-((1R,3s)-3-((1-((R or S)-3,3,3-trifluoro-2-hydroxy-2-(3-methoxyphenyl)propanoyl)piperidin-4-yl)methyl)cyclobutylamino)benzamide

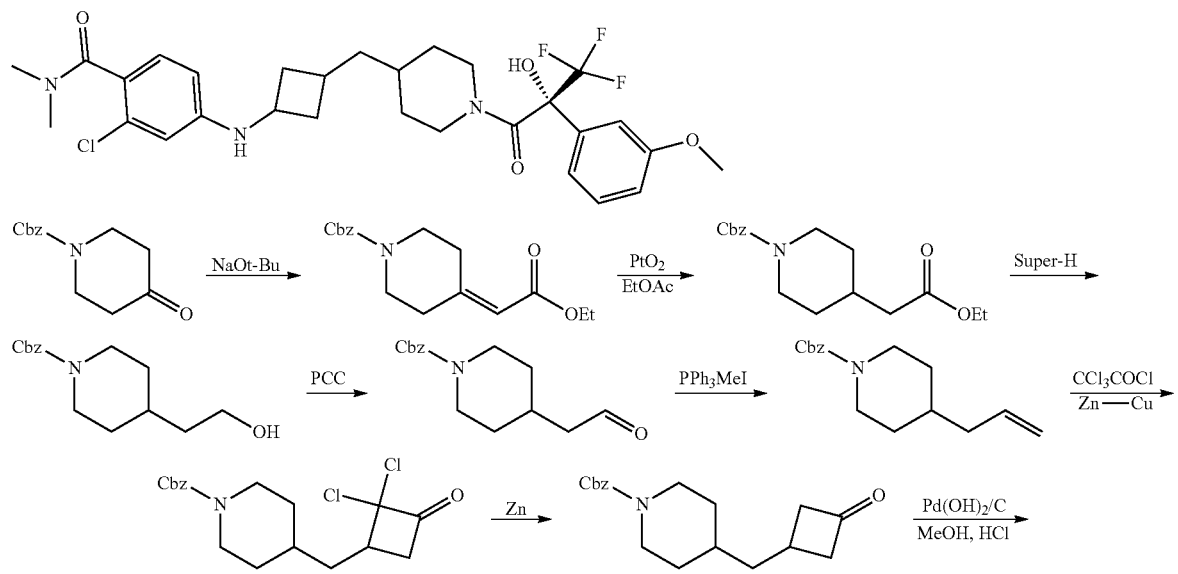

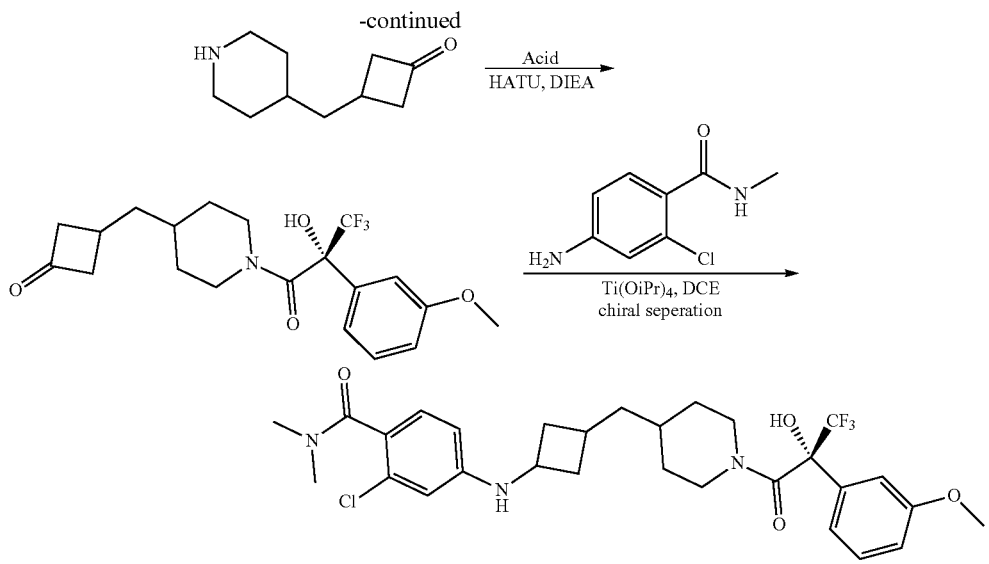

benzyl 4-(2-ethoxy-2-oxoethylidene)piperidine-1-carboxylate

To a solution of ethyl 2-(dimethoxyphosphoryl)acetate (40.4 g, 206 mmol) in THF (200 mL) was added sodium 2-methylpropan-2-olate (24.72 g, 257 mmol) at 0° C. After stirring for 1 h, benzyl 4-oxopiperidine-1-carboxylate (40 g, 171 mmol) was added to the mixture, then the mixture was stirred for 2 h at RT, quenched with aq NH$_4$Cl (50 mL) and extracted with EtOAc (3×200 mL). The organic layers was dried over anhydrous Na$_2$SO$_4$, filtered and concentrated. The crude product was purified by column chromatography (silica gel: 300-400 mesh, PE/EtOAc=10/1) to give the benzyl 4-(2-ethoxy-2-oxoethylidene)piperidine-1-carboxylate. LRMS m/z (M+H) 304.2 found, 304.1 required.

benzyl 4-(2-ethoxy-2-oxoethyl)piperidine-1-carboxylate

A mixture of benzyl 4-(2-ethoxy-2-oxoethylidene)piperidine-1-carboxylate (44 g, 145 mmol) and platinum(IV) oxide (1.647 g) was evacuated and then refill with hydrogen (three times). The mixture was stirred overnight at RT under H$_2$ balloon, then filtered and concentrated to afford benzyl 4-(2-ethoxy-2-oxoethyl)piperidine-1-carboxylate. LRMS m/z (M+H) 306.2 found, 306.1 required.

benzyl 4-(2-hydroxyethyl)piperidine-1-carboxylate

To a solution of benzyl 4-(2-ethoxy-2-oxoethyl)piperidine-1-carboxylate (44 g, 144 mmol) in DCM (50 mL) was added Super-hydride (288 mL, 288 mmol, 1M in THF) at 0° C. The mixture was stirred for 3 h at RT, quenched with aq NH$_4$Cl (200 mL) and extracted with EtOAc (3×200 mL). The organic layers was dried over anhydrous Na$_2$SO$_4$, filtered and concentrated. The crude product was purified by column chromatography (silica gel: 300-400 mesh, PE/EtOAc=1/1) to give the benzyl 4-(2-hydroxyethyl)piperidine-1-carboxylate. LRMS m/z (M+H) 264.2 found, 264.2 required.

benzyl 4-(2-oxoethyl)piperidine-1-carboxylate

A mixture of benzyl 4-(2-hydroxyethyl)piperidine-1-carboxylate (27 g, 103 mmol), PCC (44.2 g, 205 mmol) and silica gel (50 g) in DCM (300 mL) was stirred for 3 h at RT, then filtered. The filtrate was concentrated, dissolved with Et$_2$O (500 mL) and washed with water (3×100 mL), brine (3×50 mL). The organic layer was dried over anhydrous Na$_2$SO$_4$, filtered and concentrated to give benzyl 4-(2-oxoethyl)piperidine-1-carboxylate. LRMS m/z (M+H) 262.2 found, 262.1 required.

benzyl 4-allylpiperidine-1-carboxylate

To a solution of iodo(methyl)triphenylphosphorane (16.24 g, 40.2 mmol) in THF (100 mL) was added potassium 2-methylpropan-2-olate (6.01 g, 53.6 mmol) at 0° C. After stirring for 1 h at 0° C., benzyl 4-(2-oxoethyl)piperidine-1-carboxylate (7 g, 26.8 mmol) was added to the mixture, then the mixture was stirred for 2 h at RT, quenched with aq NH$_4$Cl (50 mL) and extracted with EtOAc (3×200 mL). The organic layer was dried over anhydrous Na$_2$SO$_4$, filtered and concentrated. The crude product was purified by column chromatography (silica gel: 300-400 mesh, PE/EtOAc=40/1) to give benzyl 4-allylpiperidine-1-carboxylate. LRMS m/z (M+H) 260.2 found, 260.2 required.

benzyl 4-((2,2-dichloro-3-oxocyclobutyl)methyl)piperidine-1-carboxylate

A mixture of benzyl 4-allylpiperidine-1-carboxylate (3 g, 11.57 mmol) and zinc-copper couple (7.5 g, 58.2 mmol) in Et$_2$O (100 mL) was added 2,2,2-trichloroacetyl chloride (11 g, 60.5 mmol). The resulting mixture was stirred at RT for 2 h. Then the reaction mixture was poured into saturated NaHCO$_3$ (100 mL) and filtered. The filtrate was extracted with EtOAc (100 mL×3), dried, concentrated to give benzyl 4-((2,2-dichloro-3-oxocyclobutyl)methyl)piperidine-1-carboxylate which was used in the next step directly. LRMS m/z (M+H) 370.2 found, 370.1 required.

benzyl 4-((3-oxocyclobutyl)methyl)piperidine-1-carboxylate

A mixture of benzyl 4-((2,2-dichloro-3-oxocyclobutyl)methyl)piperidine-1-carboxylate (3.8 g, 10.26 mmol) in saturated ammonium chloride in MeOH solution (200 mL)

was added Zn (3.3 g, 51.3 mmol). The mixture was stirred at RT overnight. The reaction mixture was filtered and the filtrate was concentrated and EtOAc (300 mL) was added. Then this mixture was filtered again. This filtrate was evaporated and purified by column chromatography (silica gel: 300-400 mesh, PE/EtOAc=20/1) to give benzyl 4-((3-oxocyclobutyl)methyl)piperidine-1-carboxylate. LRMS m/z (M+H) 302.2 found, 302.2 required.

3-(piperidin-4-ylmethyl)cyclobutanone

A mixture of benzyl 4-((3-oxocyclobutyl)methyl)piperidine-1-carboxylate (1.2 g, 4 mmol), 20% Pd(OH)$_2$/C (120 mg) and conc. HCl (2 drops) in MeOH (10 mL) was degassed and backfilled with H$_2$ (three times). The mixture was stirred at rt under H$_2$ balloon overnight. The catalyst was filtered off and the filtrate was concentrated to afford crude 3-(piperidin-4-ylmethyl)cyclobutanone. LRMS m/z (M+H) 168.0 found, 168.1 required.

(R or S)-3-((1-(3,3,3-trifluoro-2-hydroxy-2-(3-methoxyphenyl)propanoyl)piperidin-4-yl)methyl)cyclobutanone A mixture of crude 3-(piperidin-4-ylmethyl)cyclobutanone (400 mg, 2 mmol), (R or S)-3,3,3-trifluoro-2-hydroxy-2-(3-methoxyphenyl)propanoic acid (500 mg, 2 mmol), HATU (1.14 g, 3 mmol) and DIEA (774 mg, 6 mmol) in THF (20 mL) was stirred at rt overnight. The mixture was concentrated and the residue was purified by reverse phase HPLC (Mobile phase: methanol/water (10 mM NH$_4$HCO$_3$)) to give (R or S)-3-((1-(3,3,3-trifluoro-2-hydroxy-2-(3-methoxyphenyl)propanoyl)piperidin-4-yl)methyl)cyclobutanone. LRMS m/z (M+H) 400.1 found, 400.2 required.

2-chloro-N,N-dimethyl-4-((1R,3s)-3-((1-((R or S)-3,3,3-trifluoro-2-hydroxy-2-(3-methoxyphenyl)propanoyl)piperidin-4-yl)methyl)cyclobutylamino)benzamide A mixture of (R or S)-3-((1-(3,3,3-trifluoro-2-hydroxy-2-(3-methoxyphenyl)propanoyl)piperidin-4-yl)methyl)cyclobutanone (100 mg, 0.25 mmol), 4-amino-2-chloro-N,N-dimethylbenzamide (74 mg, 0.375 mmol) and titanium isopropoxide (142 mg, 0.5 mmol) in DCE (10 mL) was heated to 100° C. for 1 h under CEM Microwave Reactor. After being cooled to rt, NaBH$_4$ (28 mg, 0.75 mmol) was added to the mixture. The resulting mixture was stirred at rt for another 2 h, poured into aq NH$_4$Cl (50 mL) and extracted with EtOAc (50 mL×3). The combined organic layer was washed with brine (20 mL), dried over anhydrous Na$_2$SO$_4$, filtered and concentrated. The residue was purified by reverse phase HPLC (Mobile phase: methanol/water (10 mM NH$_4$HCO$_3$)) to give a mixture of cis/trans isomers. LRMS m/z (M+H) 582.2 found, 582.2 required. The cis/trans mixture was resolved by Chiral-HPLC (column: Regiscell; (250*4.6 mm 5 um); mobile phase: SCF—CO2:MeOH (0.1% DEA)=2.4:0.6; flow: 3.0 mL/min; temperature: 40° C.) to give 2-chloro-N,N-dimethyl-4-((1S,3r)-3-((1-((R or S)-3,3,3-trifluoro-2-hydroxy-2-(3-methoxyphenyl)propanoyl)piperidin-4-yl)methyl)cyclobutylamino)benzamide (RT=5.37 min) and 2-chloro-N,N-dimethyl-4-((1R,3s)-3-((1-((R or S)-3,3,3-trifluoro-2-hydroxy-2-(3-methoxyphe-nyl)propanoyl)piperidin-4-yl)methyl)cyclobutylamino)benzamide (RT=6.06 min).

Example 12-1

2-chloro-N,N-dimethyl-6-(methyl(2-(7-(2-methyl-2-phenylpropanoyl)-7-azaspiro[3.5]nonan-2-yl)ethyl)amino)nicotinamide

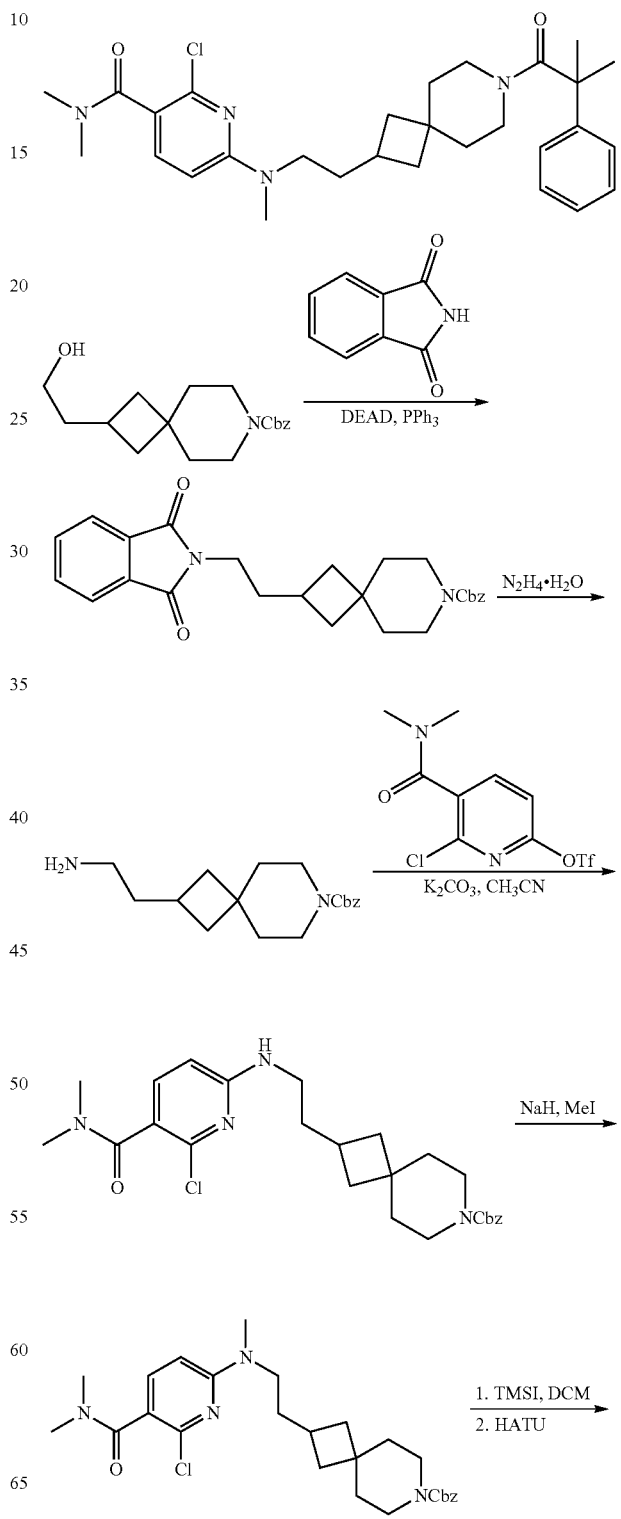

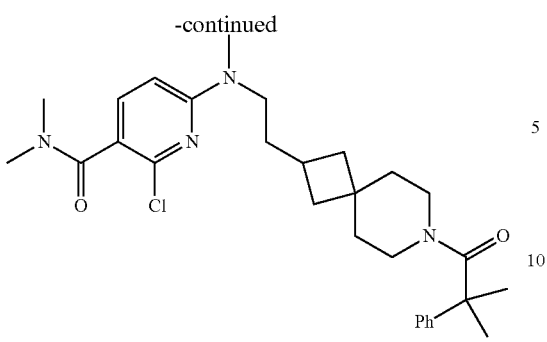

benzyl 2-(2-(1,3-dioxoisoindolin-2-yl)ethyl)-7-azaspiro[3.5]nonane-7-carboxylate To a mixture of benzyl 2-(2-hydroxyethyl)-7-azaspiro[3.5]nonane-7-carboxylate (300 mg, 0.99 mmol), isoindoline-1,3-dione (160 mg, 1.09 mmol) and triphenylphosphine (340 mg, 1.29 mmol) in THF (5 mL) was added diethyl diazene-1,2-dicarboxylate (260 mg, 1.48 mmol). The mixture was stirred at room temperature overnight. The mixture was purified by prep-TLC (PE/EtOAc=1/1) to give benzyl 2-(2-(1,3-dioxoisoindolin-2-yl)ethyl)-7-azaspiro[3.5]nonane-7-carboxylate. LRMS m/z (M+H) 433.2 found, 433.2 required.

benzyl 2-(2-aminoethyl)-7-azaspiro[3.5]nonane-7-carboxylate

To a mixture of benzyl 2-(2-(1,3-dioxoisoindolin-2-yl)ethyl)-7-azaspiro[3.5]nonane-7-carboxylate (390 mg, 0.9 mmol) in methanol (8 mL) was added hydrazine (1 mL, 40% in water). The mixture was stirred at 60° C. for 2 h. Then EtOAc (50 mL) was added and filtered. The filtrate was concentrated to give benzyl 2-(2-aminoethyl)-7-azaspiro[3.5]nonane-7-carboxylate. LRMS m/z (M+H) 303.2 found, 303.2 required.

benzyl 2-(2-(6-chloro-5-(dimethylcarbamoyl)pyridin-2-ylamino)ethyl)-7-azaspiro[3.5]nonane-7-carboxylate A mixture of benzyl 2-(2-aminoethyl)-7-azaspiro[3.5]nonane-7-carboxylate (200 mg, 0.66 mmol), 6-chloro-5-(dimethylcarbamoyl)pyridin-2-yl trifluoromethanesulfonate (330 mg, 0.99 mmol) and potassium carbonate (274 mg, 1.98 mmol) in acetonitrile (5 mL) was stirred at 70° C. overnight. The mixture was purified by prep-TLC (PE/EtOAc, 1:3) to give benzyl 2-(2-(6-chloro-5-(dimethylcarbamoyl)pyridin-2-ylamino)ethyl)-7-azaspiro[3.5]nonane-7-carboxylate. LRMS m/z (M+H) 485.2 found, 485.2 required.

benzyl 2-(2-((6-chloro-5-(dimethylcarbamoyl)pyridin-2-yl)(methyl)amino)ethyl)-7-azaspiro[3.5]nonane-7-carboxylate To a solution of benzyl 2-(2-(6-chloro-5-(dimethylcarbamoyl)pyridin-2-ylamino)ethyl)-7-azaspiro[3.5]nonane-7-carboxylate (110 mg, 0.227 mmol, 1.0 eq) in anhydrous THF (10 mL), NaH (16.4 mg, 0.681 mmol, 3.0 eq, 60% in oil) was added in at 0° C. The mixture was stirred at rt for 0.5 h before MeI (48 mg, 0.34 mmol, 1.5 eq) was injected in. The resulting mixture was stirred at rt overnight, quenched with sat. NH$_4$Cl (4.0 mL) and extracted with DCM (15 mL×5). The organic phases were combined, washed with brine (20 mL), dried over anhydrous Na$_2$SO$_4$, filtered and concentrated in vacuo to afford benzyl 2-(2-((6-chloro-5-(dimethylcarbamoyl)pyridin-2-yl)(methyl)amino)ethyl)-7-azaspiro[3.5]nonane-7-carboxylate. LRMS m/z (M+H) 499.2 found, 499.2 required.

2-chloro-N,N-dimethyl-6-(methyl(2-(7-(2-methyl-2-phenylpropanoyl)-7-azaspiro[3.5]nonan-2-yl)ethyl)amino)nicotinamide To a solution of benzyl 2-(2-((6-chloro-5-(dimethylcarbamoyl)pyridin-2-yl)(methyl)amino)ethyl)-7-azaspiro[3.5]nonane-7-carboxylate (35 mg, 0.07 mmol) in DCM (1 mL) at 0° C. was added iodotrimethylsilane (29 mg, 0.14 mmol). The mixture was stirred at 0° C. for 20 min. The reaction was quenched with methanol (0.1 mL) and purified by prep-TLC (DCM/methanol=4:1) to give 6-((2-(7-azaspiro[3.5]nonan-2-yl)ethyl)(methyl)amino)-2-chloro-N,N-dimethylnicotinamide (25 mg). Then a mixture of 6-((2-(7-azaspiro[3.5]nonan-2-yl)ethyl)(methyl)amino)-2-chloro-N,N-dimethylnicotinamide (25 mg, 0.07 mmol), HATU (46 mg, 0.12 mmol), 2-methyl-2-phenylpropanoic acid (18 mg, 0.11 mmol) and triethylamine (22 mg, 0.21 mmol) in THF (2 mL) was stirred at room temperature overnight. The mixture was purified by prep-HPLC (mobile phase: acetonitrile/water (10 mM NH$_4$HCO$_3$)) to give 2-chloro-N,N-dimethyl-6-(methyl(2-(7-(2-methyl-2-phenylpropanoyl)-7-azaspiro[3.5]nonan-2-yl)ethyl)amino)nicotinamide. LRMS m/z (M+H) 511.2 found, 511.3 required.

Example 13-1

2-chloro-N,N-dimethyl-4-(2-(7-((R or S)-3,3,3-trifluoro-2-hydroxy-2-phenylpropanoyl)-7-azaspiro[3.5]nonan-2-yl)ethylamino)benzamide

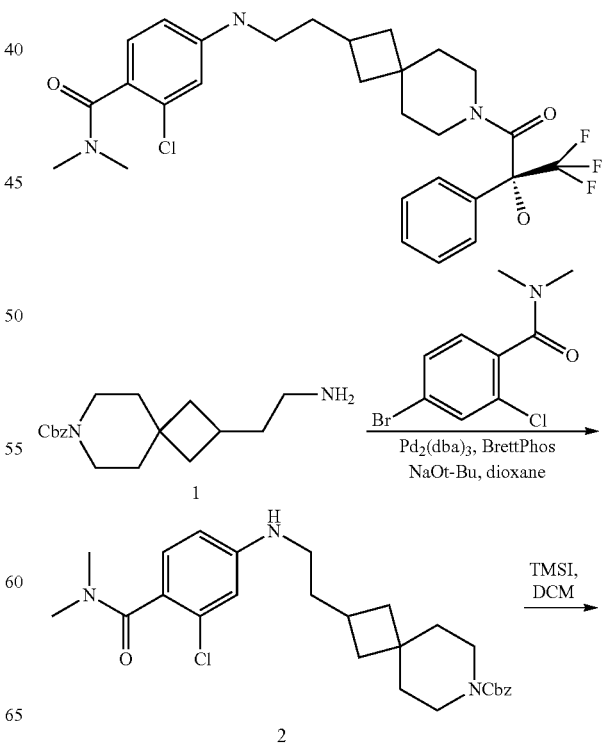

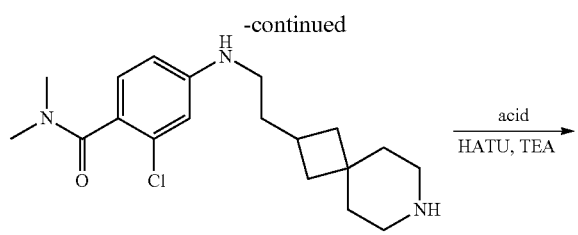

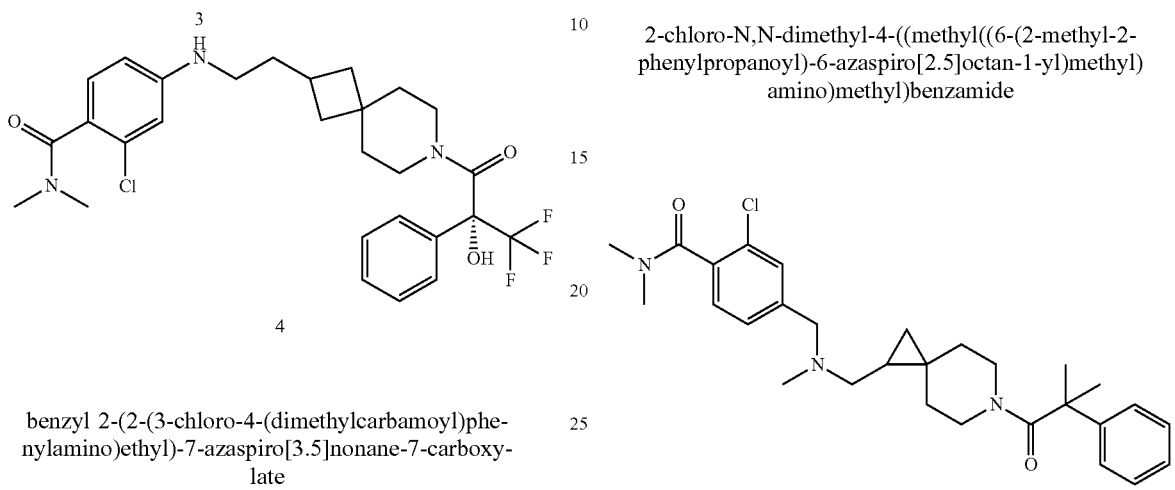

benzyl 2-(2-(3-chloro-4-(dimethylcarbamoyl)phenylamino)ethyl)-7-azaspiro[3.5]nonane-7-carboxylate A mixture of 4-bromo-2-chloro-N,N-dimethylbenzamide (260 mg, 1 mmol, 1.0 eq), benzyl 2-(2-aminoethyl)-7-azaspiro[3.5]nonane-7-carboxylate ((302 mg, 1 mmol, 1.0 eq), t-BuONa (265 mg, 3 mmol, 3 eq), BrettPhos (215 mg, 0.4 mmol, 0.4 eq) and $Pd_2(dba)_3$ (180 mg, 0.2 mmol, 0.2 eq) in 1,4-dioxane (15 ml) was stirred at 100° C. for 3 h under $N_2$. After cooling to room temperature, the reaction was monitored by LC-MS. The mixture was concentrated and the residue was diluted with EtOAc (80 mL) and washed with water (20 mL×3), brine (10 mL), dried ($Na_2SO_4$) and concentrated. The residue was purified by column chromatography (silica gel, PE:EtOAc=5:1-3:1) to give a benzyl 2-(2-(3-chloro-4-(dimethylcarbamoyl)phenylamino)ethyl)-7-azaspiro[3.5]nonane-7-carboxylate. LRMS m/z (M+H) 484.2 found, 484.2 required.

4-(2-(7-azaspiro[3.5]nonan-2-yl)ethylamino)-2-chloro-N,N-dimethylbenzamide

To a solution of benzyl 2-(2-(3-chloro-4-(dimethylcarbamoyl)phenylamino)ethyl)-7-azaspiro[3.5]nonane-7-carboxylate (35 mg, 0.072 mmol) in DCM (1 mL) at 0° C. was added iodotrimethylsilane (29 mg, 0.14 mmol). The mixture was stirred at 0° C. for 20 min. The reaction was quenched with methanol (0.1 mL) and purified by prep-TLC (DCM/methanol=8/1) to give 4-(2-(7-azaspiro[3.5]nonan-2-yl)ethylamino)-2-chloro-N,N-dimethylbenzamide. LRMS m/z (M+H) 350.1 found, 350.2 required.

2-chloro-N,N-dimethyl-4-(2-(7-((R or S)-3,3,3-trifluoro-2-hydroxy-2-phenylpropanoyl)-7-azaspiro[3.5]nonan-2-yl)ethylamino)benzamide A mixture of 4-(2-(7-azaspiro[3.5]nonan-2-yl)ethylamino)-2-chloro-N,N-dimethylbenzamide (21 mg, 0.06 mmol), HATU (46 mg, 0.12 mmol), (R or S)-3,3,3-trifluoro-2-hydroxy-2-phenylpropanoic acid (26 mg, 0.12 mmol) and triethylamine (22 mg, 0.21 mmol) in THF (2 mL) was stirred at room temperature overnight. The mixture was purified by reverse phase HPLC (mobile phase: acetonitrile/water (10 mM $NH_4HCO_3$)) to give 2-chloro-N,N-dimethyl-4-(2-(7-((R or S)-3,3,3-trifluoro-2-hydroxy-2-phenylpropanoyl)-7-azaspiro[3.5]nonan-2-yl)ethylamino)benzamide. LRMS m/z (M+H) 552.1 found, 552.2 required.

Example 14-1

2-chloro-N,N-dimethyl-4-((methyl((6-(2-methyl-2-phenylpropanoyl)-6-azaspiro[2.5]octan-1-yl)methyl)amino)methyl)benzamide

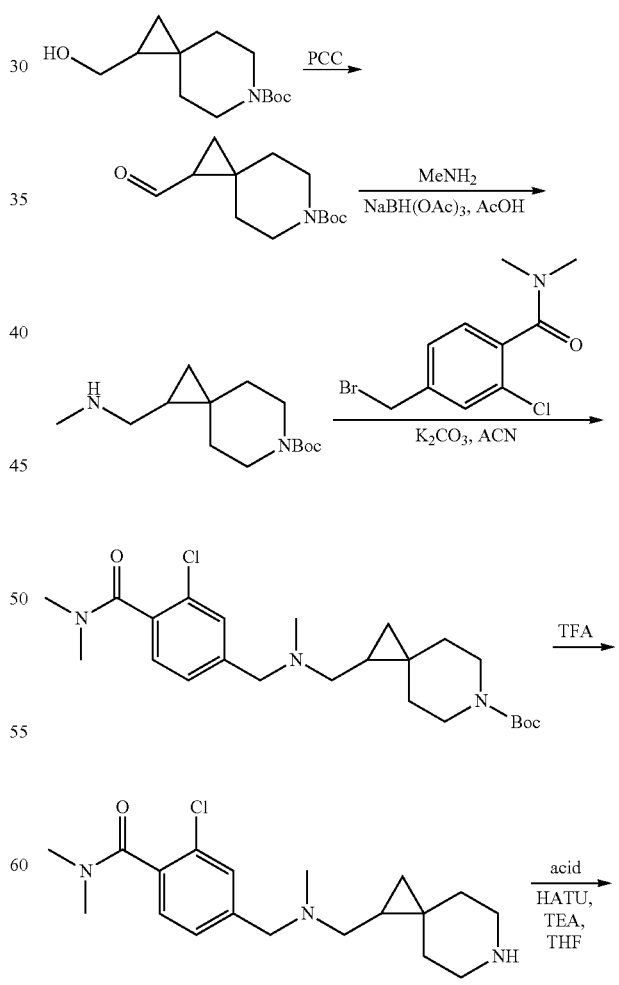

-continued

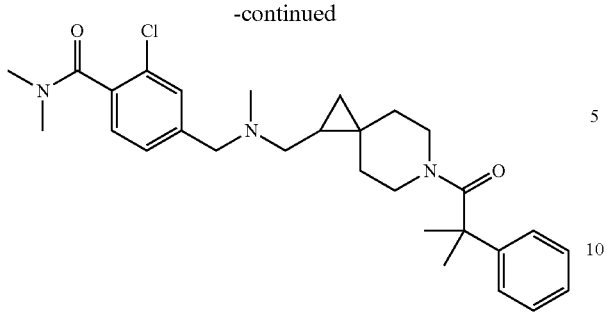

tert-butyl 1-formyl-6-azaspiro[2.5]octane-6-carboxylate

A mixture of tert-butyl 1-(hydroxymethyl)-6-azaspiro[2.5]octane-6-carboxylate (120 mg, 0.5 mmol) and PCC (161 mg, 0.75 mmol) in DCM (10 mL) was stirred at rt overnight. The mixture was diluted with ether (50 mL), filtered and the filtrate was washed with water (10 mL*3). The organic phase was dried and concentrated. The crude was purified by chromatography (silica gel: 300-400 mesh, PE/EtOAc=10/1) to give tert-butyl 1-formyl-6-azaspiro[2.5]octane-6-carboxylate. LRMS m/z (M+H) 240.1 found, 240.2 required.

tert-butyl 1-((methylamino)methyl)-6-azaspiro[2.5]octane-6-carboxylate

A mixture of tert-butyl 1-formyl-6-azaspiro[2.5]octane-6-carboxylate (20 mg, 0.083 mmol) and MeNH$_2$ (0.08 ml, 0.16 mmol, 2M in THF) in DCM (2 mL) was stirred at rt for 1 h. NaBH(OAc)$_3$ and AcOH (0.1 mL) was added to the mixture. The resulting mixture was refluxed for 1 h. After cooling to rt, the reaction was quenched with water (5 mL) and extracted with DCM (5 mL*3). The combined organic phases were washed with brine (5 mL), dried over anhydrous Na$_2$SO$_4$, filtered and concentrated to give tert-butyl 1-((methylamino)methyl)-6-azaspiro[2.5]octane-6-carboxylate which was used in next step without purification. LRMS m/z (M+H) 255.1 found, 255.2 required.

tert-butyl 1-(((3-chloro-4-(dimethylcarbamoyl)benzyl)(methyl)amino)methyl)-6-azaspiro[2.5]octane-6-carboxylate A mixture of tert-butyl 1-((methylamino)methyl)-6-azaspiro[2.5]octane-6-carboxylate (15 mg, 0.06 mmol), 4-(bromomethyl)-2-chloro-N,N-dimethylbenzamide (18 mg, 0.065 mmol) and TEA (18 mg, 0.18 mmol) in THF (2 mL) was stirred at room temperature overnight. The reaction was quenched with water (5 mL) and extracted with EtOAc (5 mL*3). The combined organic phases were washed with brine (5 mL), dried over anhydrous Na$_2$SO$_4$, filtered and concentrated to give tert-butyl 1-(((3-chloro-4-(dimethylcarbamoyl)benzyl)(methyl)amino)methyl)-6-azaspiro[2.5]octane-6-carboxylate which was used in next step without purification. LRMS m/z (M+H) 450.0 found, 450.2 required.

4-(((6-azaspiro[2.5]octan-1-ylmethyl)(methyl)amino)methyl)-2-chloro-N,N-dimethylbenzamide A mixture of tert-butyl 1-(((3-chloro-4-(dimethylcarbamoyl)benzyl)(methyl)amino)methyl)-6-azaspiro[2.5]octane-6-carboxylate (10 mg, 0.02 mmol) and 4M HCl/dioxane (2 mL) was stirred at rt for 6 h. The mixture was concentrated to afford 4-(((6-azaspiro[2.5]octan-1-ylmethyl)(methyl)amino)methyl)-2-chloro-N,N-dimethylbenzamide. LRMS m/z (M+H) 350.1 found, 350.2 required.

2-chloro-N,N-dimethyl-4-((methyl((6-(2-methyl-2-phenylpropanoyl)-6-azaspiro[2.5]octan-1-yl)methyl)amino)methyl)benzamide A mixture of 4-(((6-azaspiro[2.5]octan-1-ylmethyl)(methyl)amino)methyl)-2-chloro-N,N-dimethylbenzamide (6 mg, 0.017 mmol), 2-methyl-2-phenylpropanoic acid (3 mg, 0.018 mmol), HATU (13 mg, 0.034 mmol) and TEA (5 mg, 0.05 mmol) in THF (2 mL) was stirred at RT overnight. The mixture was directly purified by reverse phase HPLC (mobile phase: methanol/water (10 mM NH$_4$HCO$_3$)) to afford 2-chloro-N,N-dimethyl-4-((methyl((6-(2-methyl-2-phenylpropanoyl)-6-azaspiro[2.5]octan-1-yl)methyl)amino)methyl)benzamide. LRMS m/z (M+H) 496.2 found, 496.3 required.

Example 15-1

(R or S)-2-chloro-N,N-dimethyl-4-(3-(1-(3,3,3-trifluoro-2-hydroxy-2-phenylpropanoyl)piperidin-4-yl)propyl)benzamide

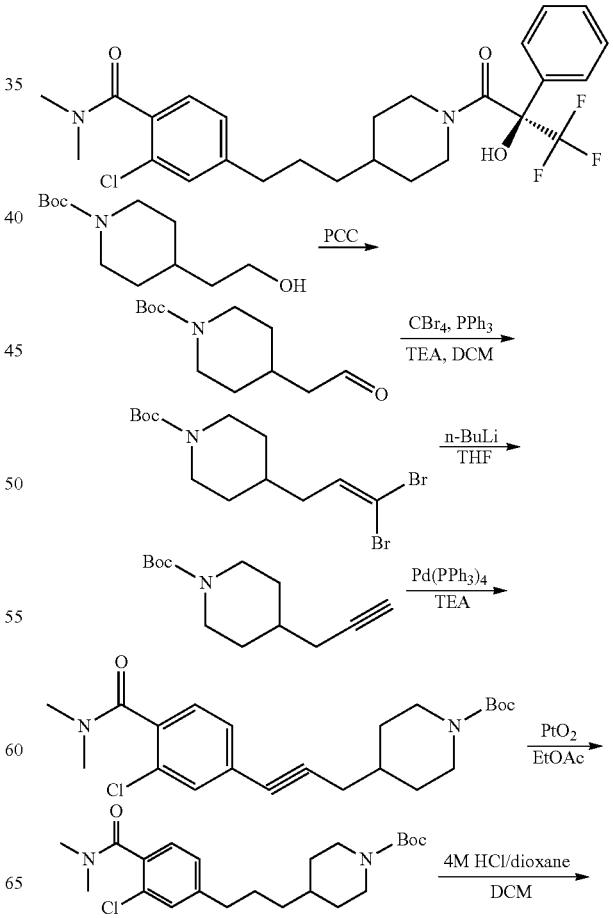

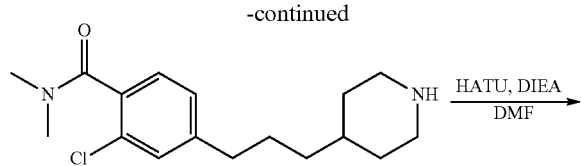

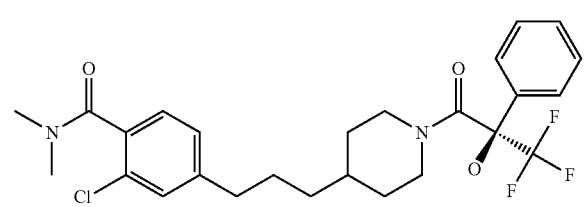

tert-butyl 4-(2-oxoethyl)piperidine-1-carboxylate

A mixture of tert-butyl 4-(2-hydroxyethyl)piperidine-1-carboxylate (1 g, 4.37 mmol) and PCC (1.88 g, 8.74 mmol) in DCM (20 mL) was stirred for 3 h at RT. Then the mixture was diluted with Et$_2$O (50 mL) and filtered. The filtrate was washed with water (3×20 mL) and brine (2×10 mL). The organic layers were dried over anhydrous Na$_2$SO$_4$, concentrated and the residue was purified by column chromatography (silica gel: 300-400 mesh, PE/EtOAc=5/1) to afford tert-butyl 4-(2-oxoethyl)piperidine-1-carboxylate. LRMS m/z (M-55) 172.2 found, 172.2 required.

tert-butyl 4-(3,3-dibromoallyl)piperidine-1-carboxylate

To a solution of CBr$_4$ (2 g, 6 mmol) in DCM (10 mL) at 0° C. was added PPh$_3$ (3.14 g, 12 mmol) in DCM (10 mL). After stirring for 30 min at 0° C., tert-butyl 4-(2-oxoethyl)piperidine-1-carboxylate (700 mg, 3 mmol) and TEA (2 mL) were added. The resulting mixture was stirred for 2 h at RT, then concentrated and the residue was purified by column chromatography (silica gel: 300-400 mesh, PE/EtOAc=20/1) to afford tert-butyl 4-(3,3-dibromoallyl)piperidine-1-carboxylate. LRMS m/z (M+H) 384.1 found, 384.0 required.

tert-butyl 4-(prop-2-ynyl)piperidine-1-carboxylate

To a solution of tert-butyl 4-(3,3-dibromoallyl)piperidine-1-carboxylate (600 mg, 1.56 mmol) in THF (10 mL) at −78° C. was added n-BuLi (1.6 mL, 4 mmol, 2.5 M in hexane). The mixture was stirred for 2 h at −78° C. warmed slowly to 25° C., then quenched with aq NH$_4$Cl (2 mL) and extracted with EtOAc (3×10 mL). The organic layer was dried over anhydrous Na$_2$SO$_4$, concentrated and the residue was purified by column chromatography (silica gel: 300-400 mesh, PE/EtOAc=10/1) to afford tert-butyl 4-(prop-2-ynyl)piperidine-1-carboxylate. LRMS m/z (M-55) 168.2 found, 168.2 required.

tert-butyl 4-(3-(3-chloro-4-(dimethylcarbamoyl)phenyl)prop-2-ynyl)piperidine-1-carboxylate A mixture of tert-butyl 4-(prop-2-ynyl)piperidine-1-carboxylate (300 mg, 1.34 mmol), 4-bromo-2-chloro-N,N-dimethylbenzamide (365 mg, 1.4 mmol), Pd(PPh$_3$)$_4$ (232 mg, 0.2 mmol) and CuI (38 mg, 0.2 mmol) in TEA (10 mL) was stirred for 1 h at 80° C. Then the mixture was filtered, and the filtrate was concentrated and the residue was purified by column chromatography (silica gel: 300-400 mesh, PE/EtOAc=8/1) to afford tert-butyl 4-(3-(3-chloro-4-(dimethylcarbamoyl)phenyl)prop-2-ynyl)piperidine-1-carboxylate. LRMS m/z (M-55) 349.1 found, 349.1 required.

tert-butyl 4-(3-(3-chloro-4-(dimethylcarbamoyl)phenyl)propyl)piperidine-1-carboxylate A mixture of tert-butyl 4-(3-(3-chloro-4-(dimethylcarbamoyl)phenyl)prop-2-ynyl)piperidine-1-carboxylate (360 mg, 0.9 mmol) and PtO$_2$ (36 mg) in EtOAc (5 mL) was evacuated and then refilled with hydrogen balloon. The mixture was stirred overnight at RT under H$_2$ balloon, then filtered and the filtrate was concentrated to afford tert-butyl 4-(3-(3-chloro-4-(dimethylcarbamoyl)phenyl)propyl)piperidine-1-carboxylate. LRMS m/z (M-55) 353.1 found, 353.1 required.

2-chloro-N,N-dimethyl-4-(3-(piperidin-4-yl)propyl)benzamide

A mixture of tert-butyl 4-(3-(3-chloro-4-(dimethylcarbamoyl)phenyl)propyl)piperidine-1-carboxylate (360 mg, 0.88 mmol) and HCl (2.2 mL, 8.8 mmol, 4M in dioxane) in DCM (2 mL) was stirred for 1 h at RT. Then the mixture was concentrated to give 2-chloro-N,N-dimethyl-4-(3-(piperidin-4-yl)propyl)benzamide. LRMS m/z (M+H) 309.1 found, 309.1 required.

(R or S)-2-chloro-N,N-dimethyl-4-(3-(1-(3,3,3-trifluoro-2-hydroxy-2-phenylpropanoyl)piperidin-4-yl)propyl)benzamide A mixture of 2-chloro-N,N-dimethyl-4-(3-(piperidin-4-yl)propyl)benzamide (30 mg, 0.1 mmol), (R or S)-3,3,3-trifluoro-2-hydroxy-2-phenylpropanoic acid (27 mg, 0.12 mmol), HATU (57 mg, 0.15 mmol) and DIEA (39 mg, 0.3 mmol) in DMF (1 mL) was stirred at RT overnight. The mixture was directly purified by reverse phase HPLC (mobile phase: methanol/water (10 mM NH$_4$HCO$_3$)) to afford (R or S)-2-chloro-N,N-dimethyl-4-(3-(1-(3,3,3-trifluoro-2-hydroxy-2-phenylpropanoyl)piperidin-4-yl)propyl)benzamide. LRMS m/z (M+H) 511.2 found, 511.2 required.

Using the same procedure described in example 15-1, but replacing tert-butyl 4-(2-oxoethyl)piperidine-1-carboxylate with tert-butyl 4-(3-hydroxypropyl)piperidine-1-carboxylate in the first step and replacing (R or S)-3,3,3-trifluoro-2-hydroxy-2-phenylpropanoic acid with the appropriate acid in the last step, or replacing tert-butyl 4-(2-oxoethyl)piperidine-1-carboxylate with tert-butyl 4-(4-hydroxybutyl)piperidine-1-carboxylate, 4-bromo-2-chloro-N,N-dimethylbenzamide with 4-bromo-2-chloro-N-methylbenzamide in the fourth step and replacing (R or S)-3,3,3-trifluoro-2-hydroxy-2-phenylpropanoic acid with the appropriate acid in the last step, the compounds in the following table were prepared.

| Example | Structure | IUPAC Name | LRMS, found [M + H] |
|---|---|---|---|
| 15-2 | 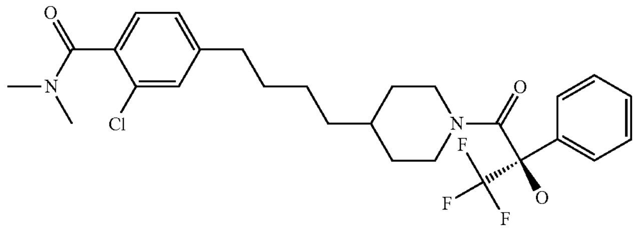 [SMILES: CN(C)C(=O)c1ccc(CCCCC2CCN(C(=O)[C@](O)(c3ccccc3)C(F)(F)F)CC2)cc1Cl] | (R or S)-2-chloro-N,N-dimethyl-4-(4-(1-(3,3,3-trifluoro-2-hydroxy-2-phenylpropanoyl)piperidin-4-yl)butyl)benzamide | 525.1 |
| 15-3 | 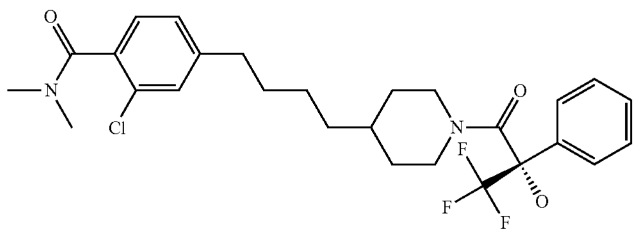 [SMILES: CN(C)C(=O)c1ccc(CCCCC2CCN(C(=O)[C@@](O)(c3ccccc3)C(F)(F)F)CC2)cc1Cl] | (S or R)-2-chloro-N,N-dimethyl-4-(4-(1-(3,3,3-trifluoro-2-hydroxy-2-phenylpropanoyl)piperidin-4-yl)butyl)benzamide | 525.1 |
| 15-4 | 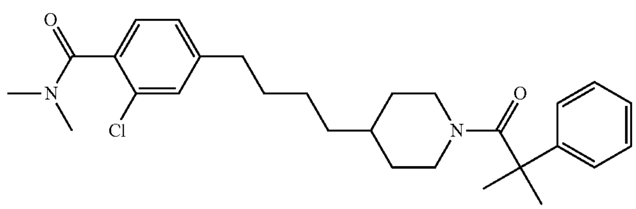 [SMILES: CN(C)C(=O)c1ccc(CCCCC2CCN(C(=O)C(C)(C)c3ccccc3)CC2)cc1Cl] | 2-chloro-N,N-dimethyl-4-(4-(1-(2-methyl-2-phenylpropanoyl)piperidin-4-yl)butyl)benzamide | 469.2 |
| 15-5 | 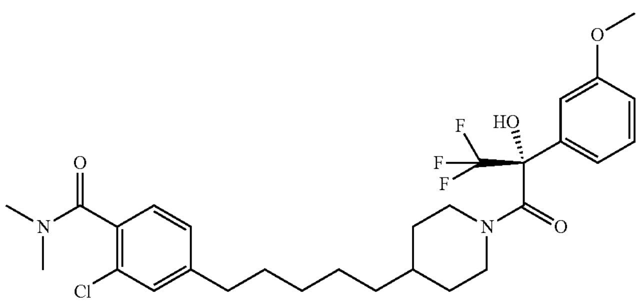 | (R or S)-2-chloro-N,N-dimethyl-4-(5-(1-(3,3,3-trifluoro-2-hydroxy-2-(3-methoxyphenyl)propanoyl)piperidin-4-yl)pentyl)benzamide | 569.1 |
| 15-6 | 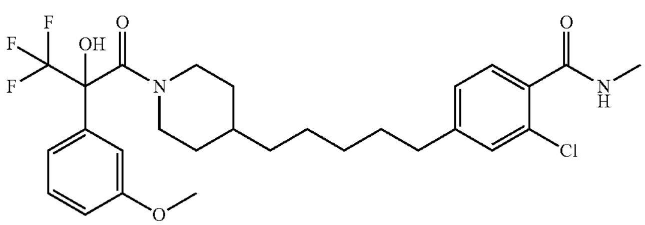 [SMILES: CNC(=O)c1ccc(CCCCCC2CCN(C(=O)C(O)(c3cccc(OC)c3)C(F)(F)F)CC2)cc1Cl] | (R or S)-2-chloro-N-methyl-4-(5-(1-(3,3,3-trifluoro-2-hydroxy-2-(3-methoxyphenyl)propanoyl)piperidin-4-yl)pentyl)benzamide | 555.1 |
| 15-7 | 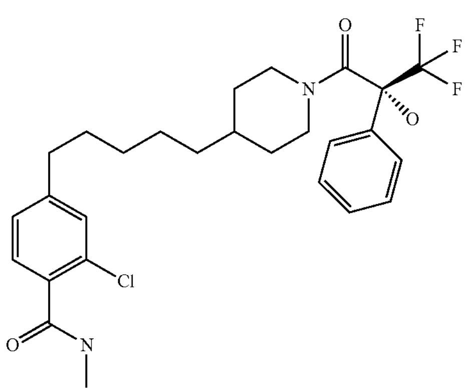 [SMILES: CNC(=O)c1ccc(CCCCCC2CCN(C(=O)[C@](O)(c3ccccc3)C(F)(F)F)CC2)cc1Cl] | (R or S)-2-chloro-N-methyl-4-(5-(1-(3,3,3-trifluoro-2-hydroxy-2-phenylpropanoyl)piperidin-4-yl)pentyl)benzamide | 525.1 |

| Example | Structure | IUPAC Name | LRMS, found [M + H] |
|---------|-----------|------------|---------------------|
| 15-8 | 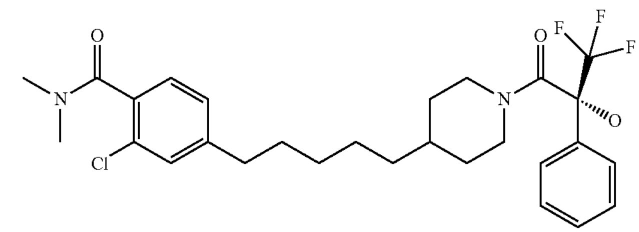 [SMILES: CN(C)C(=O)c1ccc(CCCCCC2CCN(C(=O)[C@](O)(c3ccccc3)C(F)(F)F)CC2)cc1Cl] | (R or S)-2-chloro-N,N-dimethyl-4-(5-(1-(3,3,3-trifluoro-2-hydroxy-2-phenylpropanoyl)piperidin-4-yl)pentyl)benzamide | 539.1 |
| 15-9 | 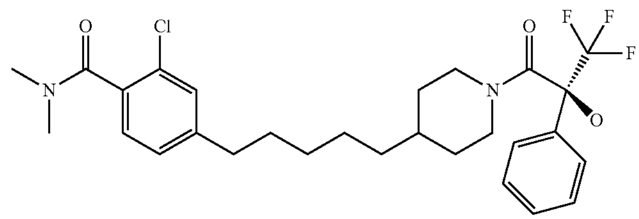 [SMILES: CN(C)C(=O)c1ccc(CCCCCC2CCN(C(=O)[C@@](O)(c3ccccc3)C(F)(F)F)CC2)cc1Cl] | (S or R)-2-chloro-N,N-dimethyl-4-(5-(1-(3,3,3-trifluoro-2-hydroxy-2-phenylpropanoyl)piperidin-4-yl)pentyl)benzamide | 539.1 |
Example 16-1
2-chloro-N,N-dimethyl-4-(3-(7-((R or S)-3,3,3-trifluoro-2-hydroxy-2-(3-methoxyphenyl)propanoyl)-7-azaspiro 13.51 nonan-2-yl)propyl)benzamide
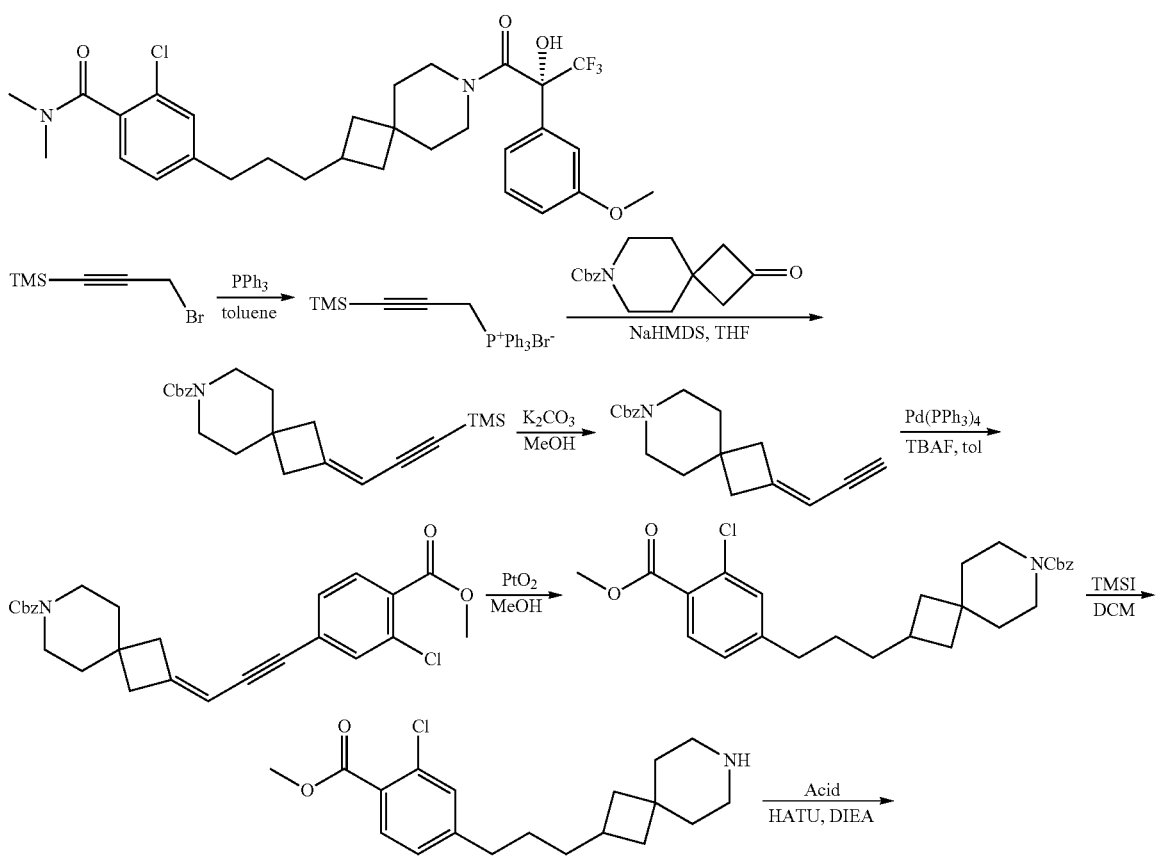

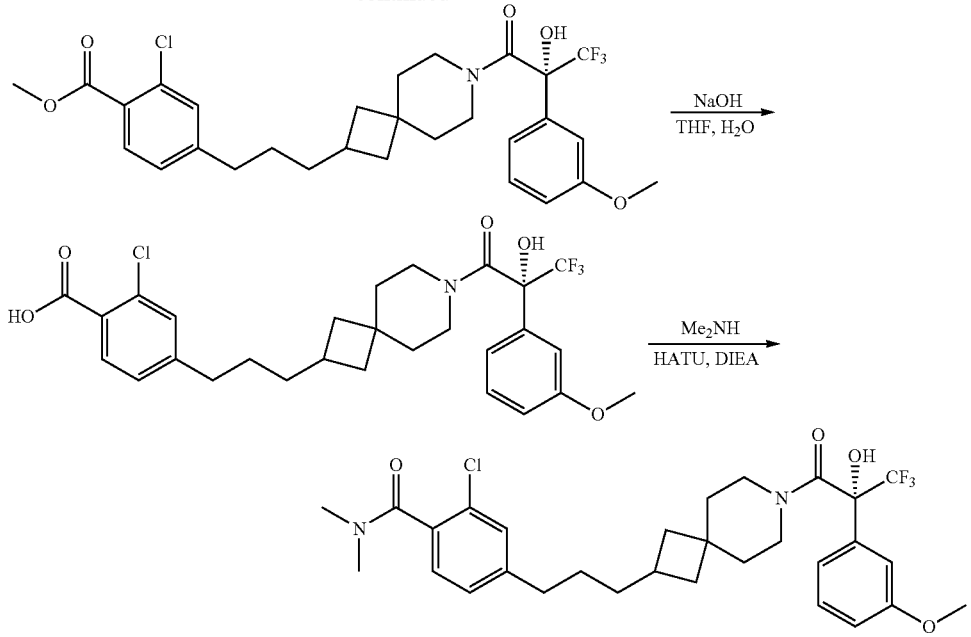

Triphenyl(3-(trimethylsilyl)prop-2-ynyl)phosphonium bromide

A mixture of (3-bromoprop-1-ynyl)trimethylsilane (5.3 g, 27.7 mmol) and triphenylphosphine (7.5 g, 28.6 mmol) in toluene (100 mL) was stirred at room temperature for 6 h. The mixture was filtered and the solid was washed with EtOAc (30 mL*3) to give triphenyl(3-(trimethylsilyl)prop-2-ynyl)phosphonium bromide. LRMS m/z (M-Br) 373.1 found, 373.2 required.

benzyl 2-(3-(trimethylsilyl)prop-2-ynylidene)-7-azaspiro[3.5]nonane-7-carboxylate To a solution of triphenyl(3-(trimethylsilyl)prop-2-ynyl)phosphonium bromide (1.8 g, 3.66 mmol) in THF (20 mL) at −78° C. was added NaHMDS (4.7 mL, 4.7 mmol, 1.0 M in THF). After being stirred at −78° C. for 2 h, a solution of benzyl 2-oxo-7-azaspiro[3.5]nonane-7-carboxylate (0.91 g, 3.33 mmol) in THF (5 mL) was added. The resulting mixture was stirred at room temperature overnight, quenched with sat. ammonium chloride (30 mL), extracted with EtOAc (30 mL*2), dried, concentrated and the residue was purified on silica gel (PE/EtOAc, 50:1 to 20:1) to give the benzyl 2-(3-(trimethylsilyl)prop-2-ynylidene)-7-azaspiro[3.5]nonane-7-carboxylate. LRMS m/z (M+H) 368.1 found, 368.2 required.

benzyl 2-(prop-2-ynylidene)-7-azaspiro[3.5]nonane-7-carboxylate

To a solution of benzyl 2-(3-(trimethylsilyl)prop-2-ynylidene)-7-azaspiro[3.5]nonane-7-carboxylate (940 mg, 2.6 mmol) in methanol (15 mL) was added potassium carbonate (1.1 g, 7.7 mmol). The mixture was stirred at room temperature for 2 h. The mixture was filtered and the filtrate was concentrated. The residue was dissolved in water (20 mL) and extracted with EtOAc (30 mL). The organic phase was dried and concentrated to give benzyl 2-(prop-2-ynylidene)-7-azaspiro[3.5]nonane-7-carboxylate. LRMS m/z (M+H) 296.1 found, 296.1 required.

benzyl 2-(3-(3-chloro-4-(methoxycarbonyl)phenyl)prop-2-ynylidene)-7-azaspiro[3.5]nonane-7-carboxylate To a mixture of benzyl 2-(prop-2-ynylidene)-7-azaspiro[3.5]nonane-7-carboxylate (700 mg, 2.37 mmol), methyl 4-bromo-2-chlorobenzoate (890 mg, 3.55 mmol) and tetrabutylammonium fluoride (1.86 g, 7.11 mmol) in toluene (20 mL) was added Pd(PPh$_3$)$_4$ (275 mg, 0.24 mmol). The mixture was stirred under N$_2$ at 85° C. for 2.5 h. Then water (40 mL) was added. The mixture was extracted with EtOAc (30 mL*2), dried, concentrated and purified on silica gel (PE/EtOAc, 50:1 to 20:1) to give benzyl 2-(3-(3-chloro-4-(methoxycarbonyl)phenyl)prop-2-ynylidene)-7-azaspiro[3.5]nonane-7-carboxylate. LRMS m/z (M+H) 464.1 found, 464.2 required.

benzyl 2-(3-(3-chloro-4-(methoxycarbonyl)phenyl)propyl)-7-azaspiro[3.5]nonane-7-carboxylate To a solution of benzyl 2-(3-(3-chloro-4-(methoxycarbonyl)phenyl)prop-2-ynylidene)-7-azaspiro[3.5]nonane-7-carboxylate (800 mg, 1.7 mmol) in methanol (15 mL) was added PtO$_2$ (100 mg). The mixture was stirred under H$_2$ balloon at room temperature for 40 min. was and then filtered. The filtrate was concentrated to give benzyl 2-(3-(3-chloro-4-(methoxycarbonyl)phenyl)propyl)-7-azaspiro[3.5]nonane-7-carboxylate. LRMS m/(M+H) 470.1 found, 470.2 required.

methyl 4-(3-(7-azaspiro[3.5]nonan-2-yl)propyl)-2-chlorobenzoate

To a solution of benzyl 2-(3-(3-chloro-4-(methoxycarbonyl)phenyl)propyl)-7-azaspiro[3.5]nonane-7-carboxylate (80 mg, 0.18 mmol) in DCM (1.5 mL) at 0° C. was added iodotrimethylsilane (72 mg, 0.36 mmol). The mixture was stirred at 0° C. for 1 h. The reaction was quenched with methanol (0.1 mL) and purified by prep-TLC (DCM/methanol=8:1) to give methyl 4-(3-(7-azaspiro[3.5]nonan-2-yl)propyl)-2-chlorobenzoate. LRMS m/z (M+H) 336.1 found, 336.2 required.

methyl 2-chloro-4-(3-(7-((R or S)-3,3,3-trifluoro-2-hydroxy-2-(3-methoxyphenyl)propanoyl)-7-azaspiro[3.5]nonan-2-yl)propyl)benzoate A mixture of methyl 4-(3-(7-azaspiro[3.5]nonan-2-yl)propyl)-2-chlorobenzoate (60 mg, 0.18 mmol), (R or S)-3,3,3-trifluoro-2-hydroxy-2-(3-methoxyphenyl)propanoic acid (54 mg, 0.21 mmol), HATU (102 mg, 0.27 mmol) and triethylamine (55 mg, 0.54 mmol) in THF (2 mL) was stirred at room temperature overnight. The mixture was purified by prep-TLC (PE/EtOAc, 2:1) to give methyl 2-chloro-4-(3-(7-((R or S)-3,3,3-trifluoro-2-hydroxy-2-(3-methoxyphenyl)propanoyl)-7-azaspiro[3.5]nonan-2-yl)propyl)benzoate. LRMS m/z (M+H) 568.1 found, 568.2 required.

2-chloro-4-(3-(7-((R or S)-3,3,3-trifluoro-2-hydroxy-2-(3-methoxyphenyl)propanoyl)-7-azaspiro[3.5]nonan-2-yl)propyl)benzoic acid To a solution of methyl 2-chloro-4-(3-(7-((R or S)-3,3,3-trifluoro-2-hydroxy-2-(3-methoxyphenyl)propanoyl)-7-azaspiro[3.5]nonan-2-yl)propyl)benzoate (65 mg, 0.11 mmol) in THF/H$_2$O (1 mL/0.5 mL) was added sodium hydroxide (20 mg, 0.46 mmol). The mixture was stirred at room temperature overnight. The reaction was diluted with water (5 mL) and acidified with 1.0 N hydrochloric acid to pH=~2. The mixture was extracted with EtOAc (5 mL*2), dried and concentrated to give 2-chloro-4-(3-(7-((R or S)-3,3,3-trifluoro-2-hydroxy-2-(3-methoxyphenyl)propanoyl)-7-azaspiro[3.5]nonan-2-yl)propyl)benzoic acid. LRMS m/z (M+H) 554.2 found, 554.2 required.

2-chloro-N,N-dimethyl-4-(3-(7-((R or S)-3,3,3-trifluoro-2-hydroxy-2-(3-methoxyphenyl)propanoyl)-7-azaspiro[3.5]nonan-2-yl)propyl)benzamide A mixture of 2-chloro-4-(3-(7-((R or S)-3,3,3-trifluoro-2-hydroxy-2-(3-methoxyphenyl)propanoyl)-7-azaspiro[3.5]nonan-2-yl)propyl)benzoic acid (28 mg, 0.05 mmol), (R or S)-3,3,3-trifluoro-2-hydroxy-2-(3-methoxyphenyl)propanoic acid (13 mg, 0.05 mmol), dimethylamine hydrochloride (8 mg, 0.10 mmol), HATU (25 mg, 0.07 mmol) and triethylamine (16 mg, 0.15 mmol) in THF (1 mL) was stirred at room temperature overnight. The mixture was filtered and purified by prep-HPLC (mobile phase: CH$_3$CN/water (10 mM NH$_4$HCO$_3$)) to give 2-chloro-N,N-dimethyl-4-(3-(7-((R or S)-3,3,3-trifluoro-2-hydroxy-2-(3-methoxyphenyl)propanoyl)-7-azaspiro[3.5]nonan-2-yl)propyl)benzamide. LRMS m/z (M+H) 581.2 found, 581.2 required.

Using the same procedure described in example 16-1, but replacing (R or S)-3,3,3-trifluoro-2-hydroxy-2-(3-methoxyphenyl)propanoic acid with the appropriate acid, the compounds in the following table were prepared.

| Example | Structure | IUPAC Name | LRMS, found [M + H]+ |
|---|---|---|---|
| 16-2 | 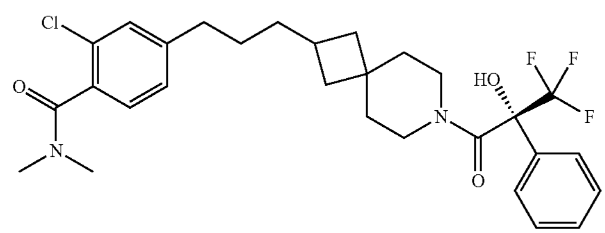 [SMILES: CN(C)C(=O)c1ccc(CCCC2CC3(CCN(C(=O)[C@](O)(c4ccccc4)C(F)(F)F)CC3)C2)cc1Cl] | 2-chloro-N,N-dimethyl-4-(3-(7-((R or S)-3,3,3-trifluoro-2-hydroxy-2-phenylpropanoyl)-7-azaspiro[3.5]nonan-2-yl)propyl)benzamide | 551.1 |
| 16-3 | 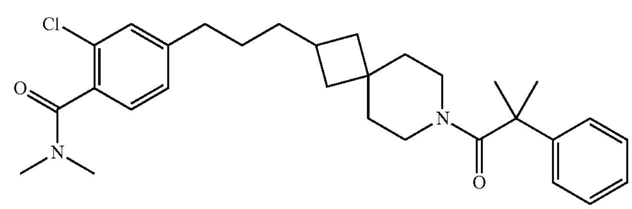 [SMILES: CN(C)C(=O)c1ccc(CCCC2CC3(CCN(C(=O)C(C)(C)c4ccccc4)CC3)C2)cc1Cl] | 2-chloro-N,N-dimethyl-4-(3-(7-(2-methyl-2-phenylpropanoyl)-7-azaspiro[3.5]nonan-2-yl)propyl)benzamide | 495.2 |
| 16-4 | 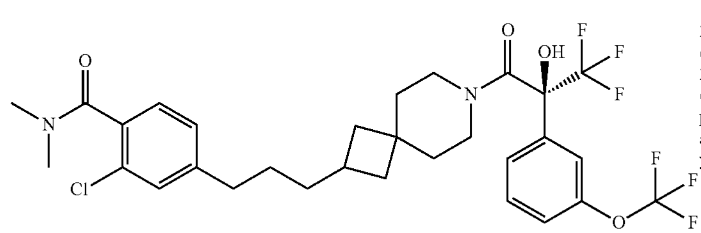 [SMILES: CN(C)C(=O)c1ccc(CCCC2CC3(CCN(C(=O)[C@@](O)(c4cccc(OC(F)(F)F)c4)C(F)(F)F)CC3)C2)cc1Cl] | 2-chloro-N,N-dimethyl-4-(3-(7-((S or R)-3,3,3-trifluoro-2-hydroxy-2-(3-(trifluoromethoxy)phenyl)propanoyl)-7-azaspiro[3.5]nonan-2-yl)propyl)benzamide | 635.2 |

Example 17-1

2-chloro-N,N-dimethyl-4-(3-((R or S)-6-((R or S)-3,3,3-trifluoro-2-hydroxy-2-(3-methoxyphenyl)propanoyl)-6-azaspiro[2.5]octan-1-yl)propyl)benzamide

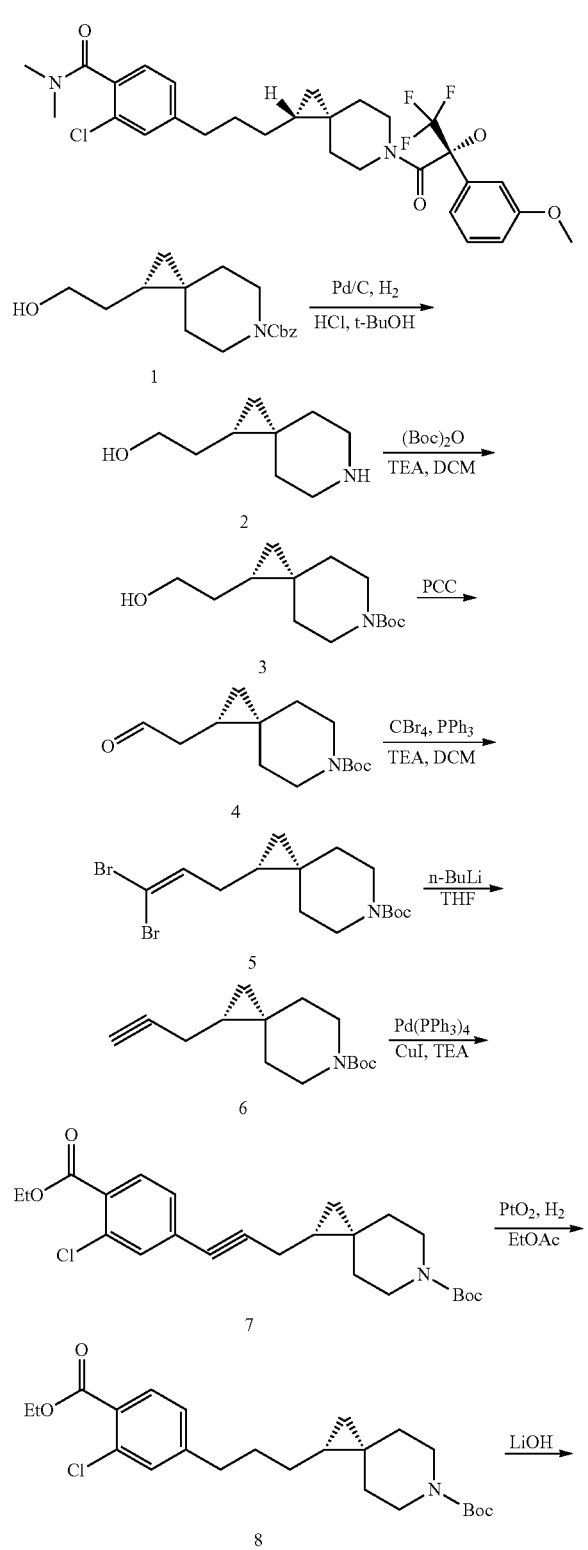

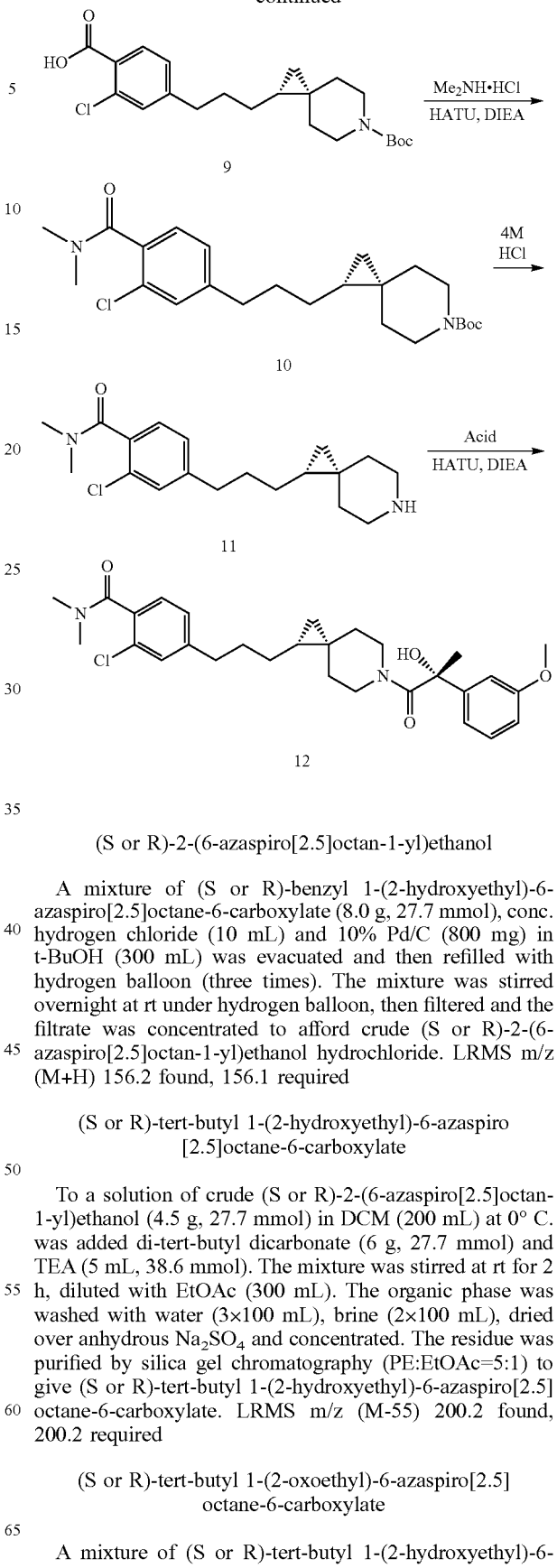

(S or R)-2-(6-azaspiro[2.5]octan-1-yl)ethanol

A mixture of (S or R)-benzyl 1-(2-hydroxyethyl)-6-azaspiro[2.5]octane-6-carboxylate (8.0 g, 27.7 mmol), conc. hydrogen chloride (10 mL) and 10% Pd/C (800 mg) in t-BuOH (300 mL) was evacuated and then refilled with hydrogen balloon (three times). The mixture was stirred overnight at rt under hydrogen balloon, then filtered and the filtrate was concentrated to afford crude (S or R)-2-(6-azaspiro[2.5]octan-1-yl)ethanol hydrochloride. LRMS m/z (M+H) 156.2 found, 156.1 required

(S or R)-tert-butyl 1-(2-hydroxyethyl)-6-azaspiro[2.5]octane-6-carboxylate

To a solution of crude (S or R)-2-(6-azaspiro[2.5]octan-1-yl)ethanol (4.5 g, 27.7 mmol) in DCM (200 mL) at 0° C. was added di-tert-butyl dicarbonate (6 g, 27.7 mmol) and TEA (5 mL, 38.6 mmol). The mixture was stirred at rt for 2 h, diluted with EtOAc (300 mL). The organic phase was washed with water (3×100 mL), brine (2×100 mL), dried over anhydrous $Na_2SO_4$ and concentrated. The residue was purified by silica gel chromatography (PE:EtOAc=5:1) to give (S or R)-tert-butyl 1-(2-hydroxyethyl)-6-azaspiro[2.5]octane-6-carboxylate. LRMS m/z (M-55) 200.2 found, 200.2 required

(S or R)-tert-butyl 1-(2-oxoethyl)-6-azaspiro[2.5]octane-6-carboxylate

A mixture of (S or R)-tert-butyl 1-(2-hydroxyethyl)-6-azaspiro[2.5]octane-6-carboxylate (6.5 g, 25.5 mmol) and PCC (6.86 g, 31.86 mmol) in DCM (50 mL) was stirred for 3 h at rt. Then the mixture was diluted with $Et_2O$ (200 mL) and filtered. The filtrate was washed with water (3×50 mL) and brine (2×50 mL). The organic layer was dried over anhydrous $Na_2SO_4$ and concentrated. The residue was purified by column chromatography (silica gel: 300-400 mesh, PE/EtOAc=5/1) to afford (S or R)-tert-butyl 1-(2-oxoethyl)-6-azaspiro[2.5]octane-6-carboxylate. LRMS m/z (M-55) 198.2 found, 198.2 required.

(R or S)-tert-butyl 1-(3,3-dibromoallyl)-6-azaspiro[2.5]octane-6-carboxylate To a solution of $CBr_4$ (13.6 g, 41.1 mmol) in DCM (50 mL) at 0° C. was added $PPh_3$ (21.54 g, 82.2 mmol) in DCM (50 mL). After stirring for 30 min at 0° C., (S or R)-tert-butyl 1-(2-oxoethyl)-6-azaspiro[2.5]octane-6-carboxylate (5.2 g, 20.55 mmol) and TEA (15 mL) was added to the reaction mixture, the mixture was stirred for 2 h at rt. Then the mixture was concentrated, and the residue was purified by column chromatography (silica gel: 300-400 mesh, PE/EtOAc=20/1) to afford (R or S)-tert-butyl 1-(3,3-dibromoallyl)-6-azaspiro[2.5]octane-6-carboxylate. LRMS m/z (M+H) 408.1 found, 408.0 required.

(S or R)-tert-butyl 1-(prop-2-ynyl)-6-azaspiro[2.5]octane-6-carboxylate

To a solution of (R or S)-tert-butyl 1-(3,3-dibromoallyl)-6-azaspiro[2.5]octane-6-carboxylate (5.8 g, 14.2 mmol) in THF (50 mL) at −78° C. was added n-BuLi (14 mL, 35 mmol, 2.5M in hexane). The mixture was stirred for 2 h at −78° C.−25° C., then quenched with aq $NH_4Cl$ (20 mL) and extracted with EtOAc (3×100 mL). The organic layer was dried over anhydrous $Na_2SO_4$ and concentrated. The residue was purified by column chromatography (silica gel: 300-400 mesh, PE/EtOAc=30/1) to afford (S or R)-tert-butyl 1-(prop-2-ynyl)-6-azaspiro[2.5]octane-6-carboxylate. LRMS m/z (M-55) 194.2 found, 194.2 required.

(S or R)-tert-butyl 1-(3-(3-chloro-4-(ethoxycarbonyl)phenyl)prop-2-ynyl)-6-azaspiro[2.5]octane-6-carboxylate A mixture of (S or R)-tert-butyl 1-(prop-2-ynyl)-6-azaspiro[2.5]octane-6-carboxylate (300 mg, 1.2 mmol), ethyl 4-bromo-2-chlorobenzoate (348 mg, 1.32 mmol), tetrakis(triphenylphosphine)palladium (208 mg, 0.18 mmol) and CuI (35 mg, 0.18 mmol) in TEA (15 mL) was stirred for 1 h at 80° C. Then the mixture was filtered, concentrated and the residue was purified by column chromatography (silica gel: 300-400 mesh, PE/EtOAc=10/1) to afford (S or R)-tert-butyl 1-(3-(3-chloro-4-(ethoxycarbonyl)phenyl)prop-2-ynyl)-6-azaspiro[2.5]octane-6-carboxylate. LRMS m/z (M-55) 376.2 found, 376.2 required.

(R or S)-tert-butyl 1-(3-(3-chloro-4-(ethoxycarbonyl)phenyl)propyl)-6-azaspiro[2.5]octane-6-carboxylate A mixture of (S or R)-tert-butyl 1-(3-(3-chloro-4-(ethoxycarbonyl)phenyl)prop-2-ynyl)-6-azaspiro[2.5]octane-6-carboxylate (400 mg, 0.93 mmol) and $PtO_2$ (40 mg) in EtOAc (5 mL) was evacuated and then refilled with hydrogen. The mixture was stirred overnight at RT under hydrogen balloon, then filtered and concentrated to afford (R or S)-tert-butyl 1-(3-(3-chloro-4-(ethoxycarbonyl)phenyl)propyl)-6-azaspiro[2.5]octane-6-carboxylate. LRMS m/z (M+Na) 458.2 found, 458.2 required.

(R or S)-4-(3-(6-(tert-butoxycarbonyl)-6-azaspiro[2.5]octan-1-yl)propyl)-2-chlorobenzoic acid A mixture of (R or S)-tert-butyl 1-(3-(3-chloro-4-(ethoxycarbonyl)phenyl)propyl)-6-azaspiro[2.5]octane-6-carboxylate (400 mg, 0.92 mmol) and LiOH (220 mg, 9.3 mmol) in MeOH (3 mL) and water (1 mL) was stirred overnight at RT. Then the mixture was acidified with 20% HCl to pH=5 and extracted with EtOAc (3×10 mL). The combined organic layers were dried over anhydrous $Na_2SO_4$ and concentrated under reduced pressure to give (R or S)-4-(3-(6-(tert-butoxycarbonyl)-6-azaspiro[2.5]octan-1-yl)propyl)-2-chlorobenzoic acid. LRMS m/z (M-55) 352.2 found, 352.2 required.

(R or S)-tert-butyl 1-(3-(3-chloro-4-(dimethylcarbamoyl)phenyl)propyl)-6-azaspiro[2.5]octane-6-carboxylate A mixture of (R or S)-4-(3-(6-(tert-butoxycarbonyl)-6-azaspiro[2.5]octan-1-yl)propyl)-2-chlorobenzoic acid (100 mg, 0.24 mmol), dimethylamine hydrochloride (58 mg, 0.71 mmol), HATU (106 mg, 0.28 mmol) and DIEA (93 mg, 0.72 mmol) in DMF (2 mL) was stirred at RT overnight. The mixture was directly purified by reverse phase HPLC (mobile phase: methanol/water (10 mM $NH_4HCO_3$)) to afford (R or S)-tert-butyl 1-(3-(3-chloro-4-(dimethylcarbamoyl)phenyl)propyl)-6-azaspiro[2.5]octane-6-carboxylate. LRMS m/z (M-99) 335.2 found, 335.2 required.

(R or S)-4-(3-(6-azaspiro[2.5]octan-1-yl)propyl)-2-chloro-N,N-dimethylbenzamide A mixture of (R or S)-tert-butyl 1-(3-(3-chloro-4-(dimethylcarbamoyl)phenyl)propyl)-6-azaspiro[2.5]octane-6-carboxylate (70 mg, 0.16 mmol) and HCl (0.5 mL, 2 mmol, 4M in Dioxane) in DCM (1 mL) was stirred for 2 h at rt. Then the mixture was concentrated to give (R or S)-4-(3-(6-azaspiro[2.5]octan-1-yl)propyl)-2-chloro-N,N-dimethylbenzamide. LRMS m/z (M+H) 335.2 found, 335.2 required.

2-chloro-N,N-dimethyl-4-(3-((R or S)-6-((R or S)-3,3,3-trifluoro-2-hydroxy-2-(3-methoxyphenyl)propanoyl)-6-azaspiro[2.5]octan-1-yl)propyl)benzamide A mixture of (R or S)-4-(3-(6-azaspiro[2.5]octan-1-yl)propyl)-2-chloro-N,N-dimethylbenzamide (20 mg, 0.06 mmol), (R or S)-3,3,3-trifluoro-2-hydroxy-2-(3-methoxyphenyl)propanoic acid (18 mg, 0.072 mmol), HATU (32 mg, 0.084 mmol) and DIEA (24 mg, 0.186 mmol) in DMF (1 mL) was stirred at rt overnight. The mixture was directly purified by reverse phase HPLC (mobile phase: methanol/water (10 mM $NH_4HCO_3$)) to afford 2-chloro-N,N-dimethyl-4-(3-((R or S)-6-((R or S)-3,3,3-trifluoro-2-hydroxy-2-(3-methoxyphenyl)propanoyl)-6-azaspiro[2.5]octan-1-yl)propyl)benzamide. LRMS m/z (M+H) 567.2 found, 567.2 required.

Using the procedure described in Example 17-1, but replacing (S or R)-benzyl 1-(2-hydroxyethyl)-6-azaspiro[2.5]octane-6-carboxylate with (R or S)-benzyl 1-(2-hydroxyethyl)-6-azaspiro[2.5]octane-6-carboxylate at the first step, replacing dimethylamine with cyclopropylamine in the ninth step, and replacing (R or S)-3,3,3-trifluoro-2-hydroxy-2-(3-methoxyphenyl)propanoic acid with the appropriate acid, the compounds in the following table were prepared.

| Example | Structure | IUPAC Name | LRMS, found [M + H]+ |
|---|---|---|---|
| 17-2 | 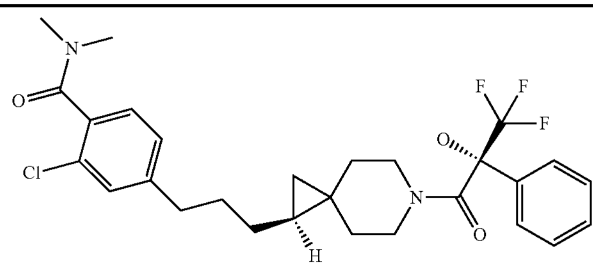 | 2-chloro-N,N-dimethyl-4-(3-((S or R)-6-((R or S)-3,3,3-trifluoro-2-hydroxy-2-phenylpropanoyl)-6-azaspiro[2.5]octan-1-yl)propyl)benzamide | 537.2 |
| 17-3 | 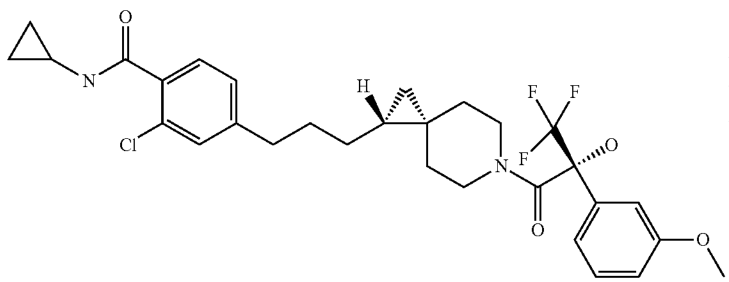 | 2-chloro-N-cyclopropyl-4-(3-((R or S)-6-((R or S)-3,3,3-trifluoro-2-hydroxy-2-(3-methoxyphenyl)propanoyl)-6-azaspiro[2.5]octan-1-yl)propyl)benzamide | 579.2 |

Example 18-1

2-chloro-N,N-dimethyl-4-((3-((R or S)-3,3,3-trifluoro-2-hydroxy-2-(3-methoxyphenyl)propanoyl)-3-azaspiro[5.5]undecan-9-yl)methyl)benzamide

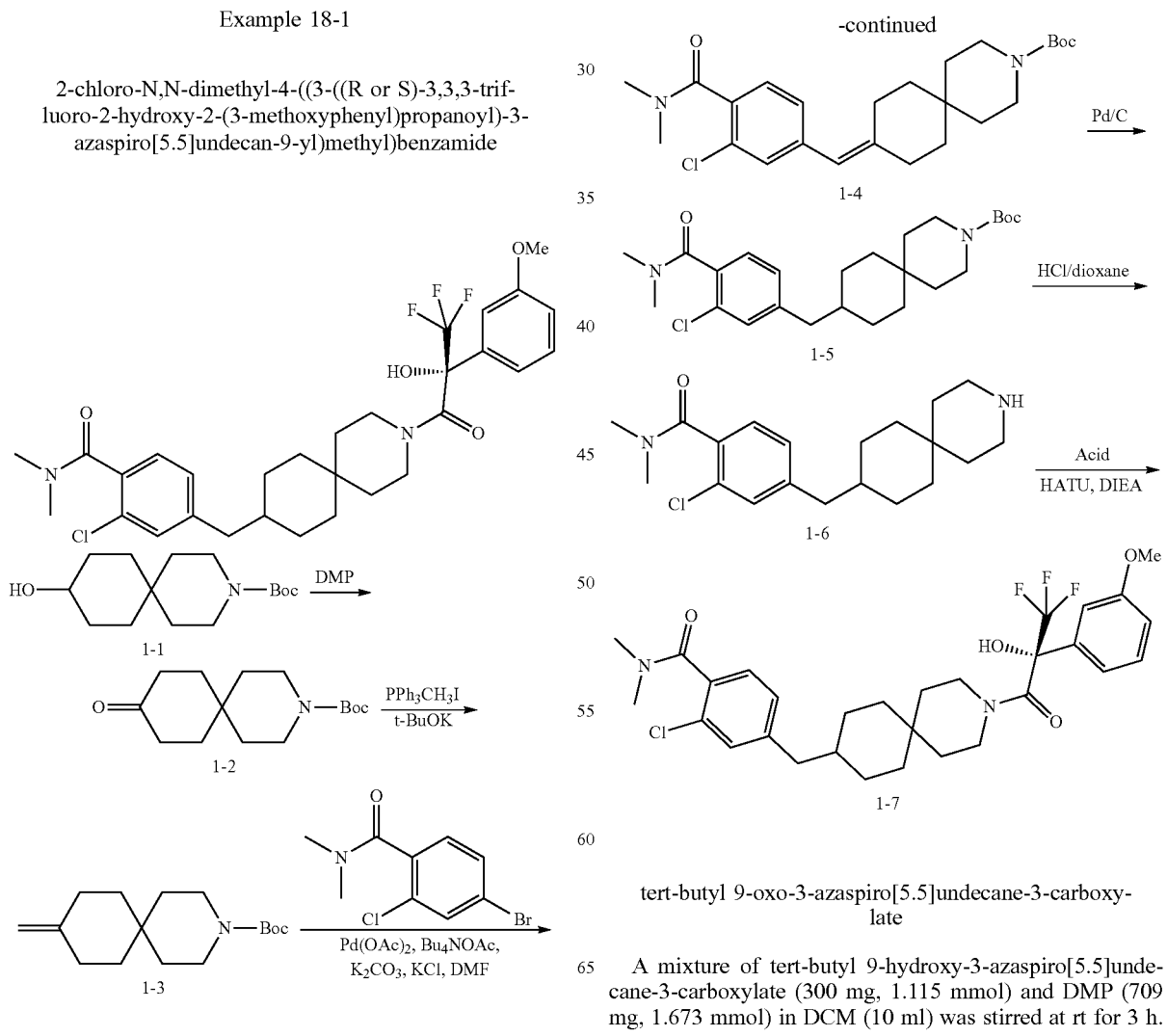

tert-butyl 9-oxo-3-azaspiro[5.5]undecane-3-carboxylate

A mixture of tert-butyl 9-hydroxy-3-azaspiro[5.5]undecane-3-carboxylate (300 mg, 1.115 mmol) and DMP (709 mg, 1.673 mmol) in DCM (10 ml) was stirred at rt for 3 h.

Then the reaction mixture was diluted with DCM (200 ml), washed with sat. NaHCO₃ (40 ml×2), brine (40 ml×1), dried and concentrated to give crude product. The crude product was purified by column chromatography (silica gel: 200-300 mesh, PE/EtOAc=10/1) to get tert-butyl 9-oxo-3-azaspiro[5.5]undecane-3-carboxylate. LRMS m/z (M+Na) 290.0 found, 290.2 required.

tert-butyl 9-methylene-3-azaspiro[5.5]undecane-3-carboxylate

A mixture of (Ph)₃PCH₃I (726 mg, 1.798 mmol) and t-BuOK (269 mg, 2.396 mmol) in THF (10 ml) was stirred at rt under N₂ atmosphere for 1 h. tert-butyl 9-oxo-3-azaspiro[5.5]undecane-3-carboxylate (160 mg, 0.599 mmol) was added to the mixture. The resulting mixture was stirred at rt for 1 h, quenched with saturated ammonium chloride solution (20 mL), extracted with ethyl acetate (100 mL×3). The combined organic layers was washed with brine (20 mL), dried over anhydrous Na₂SO₄ and concentrated to give crude product, which was purified by column chromatography (silica gel: 200-300 mesh, PE/EtOAc=10/1) to give tert-butyl 9-methylene-3-azaspiro[5.5]undecane-3-carboxylate. LRMS m/z (M-55) 210.2 found, 210.2 required.

tert-butyl 9-(3-chloro-4-(dimethylcarbamoyl)benzylidene)-3-azaspiro[5.5]undecane-3-carboxylate A mixture of tert-butyl 9-methylene-3-azaspiro[5.5]undecane-3-carboxylate (60 mg, 0.226 mmol), 4-bromo-2-chloro-N,N-dimethylbenzamide (71 mg, 0.271 mmol), Pd(AcO)₂ (20 mg, 0.09 mmol), Bu₄NOAc (109 mg, 0.452 mmol), K₂CO₃ (63 mg, 0.452 mmol) and KCl (17 mg, 0.226 mmol) in DMF (2 ml) was stirred at 100° C. under N₂ atmosphere overnight. The mixture was diluted with DCM (200 ml), washed with waster (30 ml×2), brine (30 ml×1), dried and concentrated to give crude product which was purified by column chromatography (silica gel: 200-300 mesh, PE/EtOAc=3/1) to give tert-butyl 9-(3-chloro-4-(dimethylcarbamoyl)benzylidene)-3-azaspiro[5.5]undecane-3-carboxylate. LRMS m/z (M+Na) 469.0 found, 469.2 required.

tert-butyl 9-(3-chloro-4-(dimethylcarbamoyl)benzyl)-3-azaspiro[5.5]undecane-3-carboxylate A mixture of tert-butyl 9-(3-chloro-4-(dimethylcarbamoyl)benzylidene)-3-azaspiro[5.5]undecane-3-carboxylate (77 mg, 0.173 mmol) and 10% Pd/C (23 mg) in EtOAc (10 ml) was stirred at rt under H₂ atmosphere overnight. Then the mixture was filtered and the filtrate was concentrated to give tert-butyl 9-(3-chloro-4-(dimethylcarbamoyl)benzyl)-3-azaspiro[5.5]undecane-3-carboxylate. LRMS m/z (M+Na) 471.0 found, 471.2 required.

4-(3-azaspiro[5.5]undecan-9-ylmethyl)-2-chloro-N,N-dimethylbenzamide

A mixture of tert-butyl 9-(3-chloro-4-(dimethylcarbamoyl)benzyl)-3-azaspiro[5.5]undecane-3-carboxylate (63 mg, 0.14 mmol) and HCl/dioxane (0.4 ml, 1.4 mmol, 4 M) in DCM (2 ml) was stirred at rt for 2 h. The solvent was removed under reduced pressure and the residue was basified to pH=7-8 with sat. NaHCO₃. The mixture was extracted with DCM (50 ml×3), washed with brine (30 ml), dried over anhydrous Na₂SO₄, filtered and concentrated to give 4-(3-azaspiro[5.5]undecan-9-ylmethyl)-2-chloro-N,N-dimethylbenzamide. LRMS m/z (M+H) 349.1 found, 349.2 required.

2-chloro-N,N-dimethyl-4-((3-((R or S)-3,3,3-trifluoro-2-hydroxy-2-(3-methoxyphenyl)propanoyl)-3-azaspiro[5.5]undecan-9-yl)methyl)benzamide To a solution of (R or S)-3,3,3-trifluoro-2-hydroxy-2-(3-methoxyphenyl)propanoic acid (20 mg, 0.08 mmol) in DMF (0.3 ml) was added a solution of HATU (30 mg, 0.079 mmol) in DMF (0.3 ml) at room temperature, followed by addition of 4-(3-azaspiro[5.5]undecan-9-ylmethyl)-2-chloro-N,N-dimethylbenzamide (23 mg, 0.066 mmol) and DIPEA (17 mg, 0.132 mmol) in DMF (0.4 ml) at room temperature. The resulting mixture was stirred overnight. The mixture was directly purified by reverse phase HPLC (mobile phase: methanol/water (10 mM NH₄HCO₃)) to afford 2-chloro-N,N-dimethyl-4-((3-((R or S)-3,3,3-trifluoro-2-hydroxy-2-(3-methoxyphenyl)propanoyl)-3-azaspiro[5.5]undecan-9-yl)methyl)benzamide. LRMS m/z (M+H) 581.0 found, 581.2 required.

Example 19-1

2-chloro-N,N-dimethyl-4-(3-((R or S)-3,3,3-trifluoro-2-hydroxy-2-(3-methoxyphenyl)propanoyl)-3-azaspiro[5.5]undecan-9-ylthio)benzamide

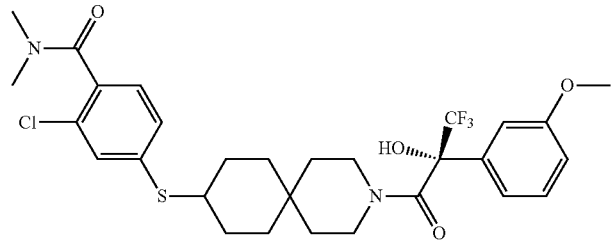

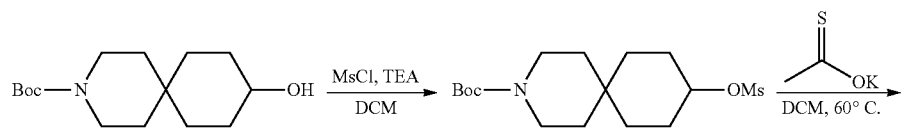

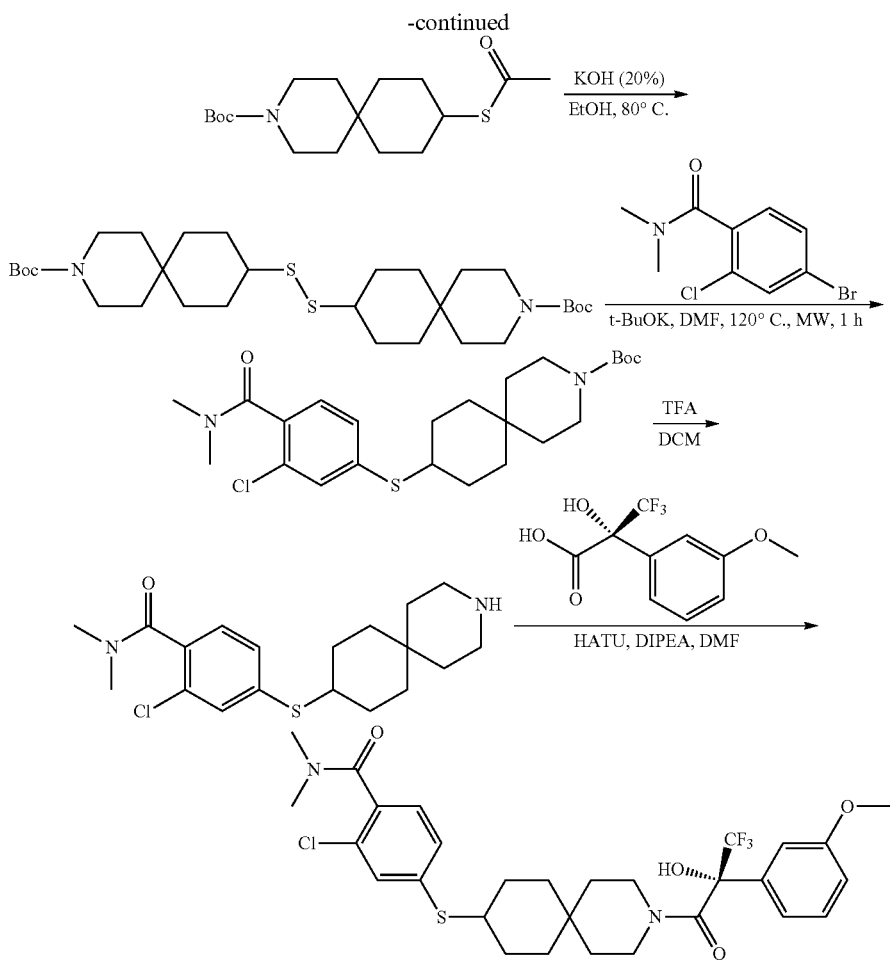

tert-butyl 9-(methylsulfonyloxy)-3-azaspiro[5.5]undecane-3-carboxylate

A solution of tert-butyl 9-hydroxy-3-azaspiro[5.5]undecane-3-carboxylate (200 mg, 0.74 mmol), MsCl (128 mg, 1.17 mmol) and TEA (226 mg, 2.23 mmol) in DCM (3 mL) was stirred overnight at rt. The mixture was diluted with EtOAc (400 mL) and washed with saturated NaHCO$_3$ (10 mL*3) and brine (10 mL). The organic layer was dried over anhydrous Na$_2$SO$_4$, filtered and concentrated to afford tert-butyl 9-(methylsulfonyloxy)-3-azaspiro[5.5]undecane-3-carboxylate. LRMS m/z (M-55) 292.0 found, 292.2 required.

tert-butyl 9-(acetylthio)-3-azaspiro[5.5]undecane-3-carboxylate

A solution of tert-butyl 9-(methylsulfonyloxy)-3-azaspiro[5.5]undecane-3-carboxylate (216 mg, 0.62 mmol), potassium ethanethioate (107 mg, 0.94 mmol) in DMF (3 ml) was stirred for 4 h at 60° C. under nitrogen atmosphere. The mixture was diluted with EtOAc (300 mL) and washed with water (10 mL*2) and brine (10 mL). The organic layer was dried over anhydrous Na$_2$SO$_4$, filtered and concentrated. The crude product was purified by column chromatography (silica gel: 200-300 mesh, PE/EtOAc=20/1) to afford tert-butyl 9-(acetylthio)-3-azaspiro[5.5]undecane-3-carboxylate. LRMS m/z (M-55) 272.1 found, 272.2 required.

tert-butyl 9-mercapto-3-azaspiro[5.5]undecane-3-carboxylate dimer

A solution of tert-butyl 9-(acetylthio)-3-azaspiro[5.5]undecane-3-carboxyl (90 mg, 0.28 mmol), KOH (2 mL, 20% in H$_2$O) in EtOH (2 mL) was stirred overnight at rt. The saturated NH$_4$Cl (10 mL) was added. The mixture was dissolved with DCM (200 mL) and washed with brine (10 mL). The organic layer was dried over anhydrous Na$_2$SO$_4$, filtered and concentrated. The residue was purified by reverse phase HPLC (mobile phase: methanol/water (10 mM NH$_4$HCO$_3$)) to afford tert-butyl 9-mercapto-3-azaspiro[5.5]undecane-3-carboxylate dimer. LRMS m/z (M+Na) 591.2 found, 591.3 required.

tert-butyl 9-(3-chloro-4-(dimethylcarbamoyl)phenylthio)-3-azaspiro[5.5]undecane-3-carboxylate A mixture of tert-butyl 9-mercapto-3-azaspiro[5.5]undecane-3-carboxylate dimer (25 mg, 0.04 mmol), 4-bromo-2-chloro-N,N-dimethylbenzamide (23 mg, 0.09 mmol) and t-BuOK (15 mg, 0.13 mmol) in DMF (1 ml) was heated to 120° C. for 2 h under microwave. The mixture was cooled and the solvent was evaporated under reduced pressure. Water (2 mL) was added. The mixture was diluted with EtOAc (150 mL), washed with brine (15 mL), dried over anhydrous Na$_2$SO$_4$, filtered and concentrated. The residue was purified by reverse phase HPLC (mobile phase: methanol/water (10 mM NH$_4$HCO$_3$)), to afford tert-butyl 9-(3-chloro-4-(dimethylcarbamoyl)phenylthio)-3-azaspiro[5.5]undecane-3-carboxylate. LRMS m/z (M+Na) 489.0 found, 489.2 required.

4-(3-azaspiro[5.5]undecan-9-ylthio)-2-chloro-N,N-dimethylbenzamide

A solution of tert-butyl 9-(3-chloro-4-(dimethylcarbamoyl)phenylthio)-3-azaspiro[5.5]undecane-3-carboxylate (7 mg, 0.02 mmol) and TFA (0.4 mL) in DCM (1 mL) was stirred for 2 h at rt. The mixture was concentrated to afford 4-(3-azaspiro[5.5]undecan-9-ylthio)-2-chloro-N,N-dimethylbenzamide. LRMS m/z (M+H) 367.1 found, 367.2 required.

2-chloro-N,N-dimethyl-4-(3-((R or S)-3,3,3-trifluoro-2-hydroxy-2-(3-methoxyphenyl)propanoyl)-3-azaspiro[5.5]undecan-9-ylthio)benzamide A solution of 4-(3-azaspiro[5.5]undecan-9-ylthio)-2-chloro-N,N-dimethylbenzamide (5 mg, 0.02 mmol), (R or S)-3,3,3-trifluoro-2-hydroxy-2-(3-methoxyphenyl)propanoic acid (6 mg, 0.02 mmol), HATU (8 mg, 0.02 mmol) and DIPEA (9 mg, 0.07 mmol) in DMF (1 mL) was stirred overnight at rt. The mixture was directly purified by reverse phase HPLC (mobile phase: methanol/water (10 mM $NH_4HCO_3$)) to afford 2-chloro-N,N-dimethyl-4-(3-((R or S)-3,3,3-trifluoro-2-hydroxy-2-(3-methoxyphenyl)propanoyl)-3-azaspiro[5.5]undecan-9-ylthio)benzamide. LRMS m/z (M+H) 599.0 found, 599.2 required.

Using the same procedure described in Example 19-1, but replacing (R or S)-3,3,3-trifluoro-2-hydroxy-2-(3-methoxyphenyl)propanoic acid with the appropriate acid, the compounds in the following table were prepared.

| Example | Structure | IUPAC Name | LRMS, found [M + H]+ |
|---|---|---|---|
| 19-2 | 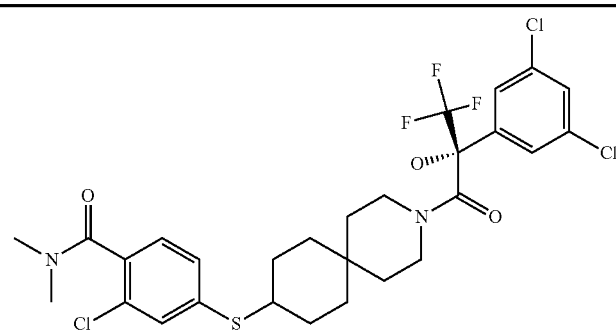 | 2-chloro-4-(3-((R or S)-2-(3,5-dichlorophenyl)-3,3,3-trifluoro-2-hydroxypropanoyl)-3-azaspiro[5.5]undecan-9-ylthio)-N,N-dimethylbenzamide | 637.0 |
| 19-3 | 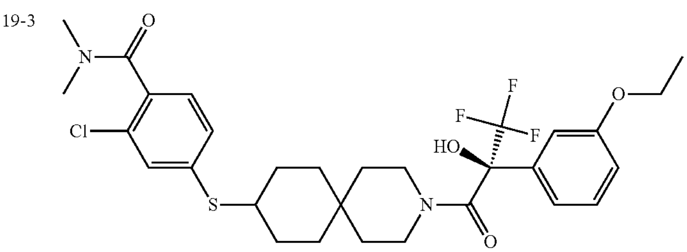 | 2-chloro-4-(3-((S or R)-2-(3-ethoxyphenyl)-3,3,3-trifluoro-2-hydroxypropanoyl)-3-azaspiro[5.5]undecan-9-ylthio)-N,N-dimethylbenzamide | 613.3 |

Example 20-1

2-chloro-4-(3-((R or S)-2-(3,5-dichlorophenyl)-3,3,3-trifluoro-2-hydroxypropanoyl)-3-azaspiro[5.5]undecan-9-ylsulfinyl)-N,N-dimethylbenzamide

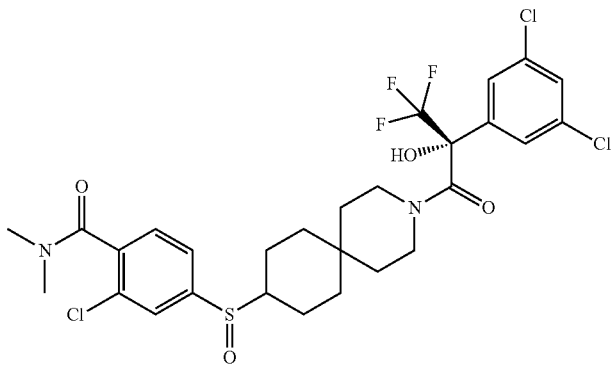 [SMILES: CN(C)C(=O)c1ccc(S(=O)C2CCC3(CC2)CCN(C(=O)[C@](O)(c2cc(Cl)cc(Cl)c2)C(F)(F)F)CC3)cc1Cl]

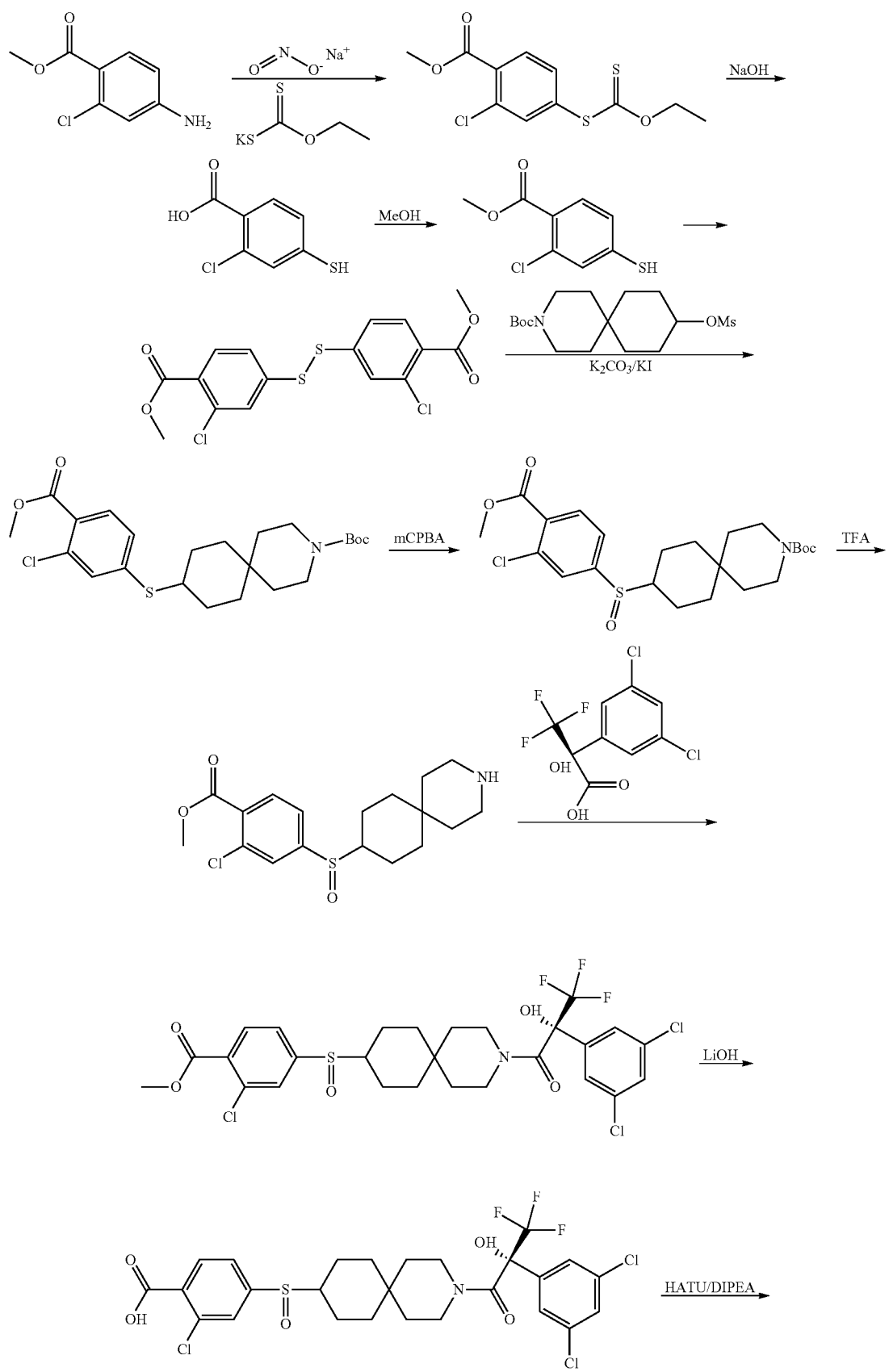

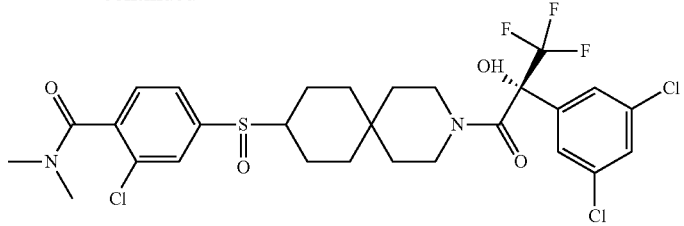

Methyl 2-chloro-4-(ethoxycarbonothioylthio)benzoate

To a suspension of methyl 4-amino-2-chlorobenzoate (1 g, 5.39 mmol) in H₂O/MeOH (2 ml/2 ml) was added conc. HCl (2 ml, 23 mmol, 4.0 eq) at 0° C., then a solution of NaNO₂ (480 mg, 6.96 mmol, 1.29 eq) in H₂O (2 ml) was added dropwise into the solution above at 0° C. over 30 min. The reaction mixture was stirred for 1 h. The resulting solution was added dropwise into a solution of potassium O-ethyl carbonodithioate (1.73 g, 10.76 mmol, 1.83 eq) in H₂O (2 ml) at 50-60° C. After being stirred for several hours, the mixture was cooled to room temperature, extracted with EA (200 ml×2), washed with brine (20 ml), dried over anhydrous Na₂SO₄ and concentrated. The residue was purified by column chromatography (silica gel, 200-300 mesh) to afford methyl 2-chloro-4-(ethoxycarbonothioylthio)benzoate. LRMS m/z (M+H) 291.0 found, 291.0 required.

2-chloro-4-mercaptobenzoic acid

To a solution of methyl 2-chloro-4-(ethoxycarbonothioylthio)benzoate (580 mg, 2.0 mmol, 1.0 eq) in EtOH (10.0 ml) was added a solution of NaOH (260 mg, 6.5 mmol, 3.25 eq) in H₂O (5.0 ml). The reaction was heated to 65° C. for 5 h. The solvent was removed under reduced pressure and the residue was acidified to pH=2-3 with conc. HCl at 0° C. and filtered. The precipitate was washed with H₂O and dried in vacuo to give 2-chloro-4-mercaptobenzoic acid. LRMS m/z (M+H) 189.0 found, 189.0 required.

dimethyl 4,4'-disulfanediylbis(2-chlorobenzoate)

To a solution of 2-chloro-4-mercaptobenzoic acid (180 mg, 0.954 mmol) in MeOH (20 ml) was added H₂SO₄ (0.25 ml, 4.69 mmol) at room temperature. The reaction was heated to 65° C. for 2 h under N₂ atmosphere and then cooled to room temperature. The solvent was removed under reduced pressure to give a residue which was basified to pH=8 with sat.NaHCO₃ at 0° C. Then the mixture was extracted with EA (100 mL×3). The combined organic fractions were washed with brine (20 mL), dried over anhydrous Na₂SO₄, filtered and concentrated to give methyl 2-chloro-4-mercaptobenzoate. LRMS m/z (M+H) 202.7 found, 203.0 required. The corresponding dimer was formed after storage.

tert-butyl 9-(3-chloro-4-(methoxycarbonyl)phenylthio)-3-azaspiro[5.5]undecane-3-carboxylate A mixture of dimethyl 4,4'-disulfanediylbis(2-chlorobenzoate) dimer (112 mg, 0.278 mmol), tert-butyl 9-((methylsulfonyl)oxy)-3-azaspiro[5.5]undecane-3-carboxylate (218 mg, 0.627 mmol), potassium carbonate (58 mg, 0.420 mmol) and potassium iodide (46.1 mg, 0.278 mmol) in DMF (3 ml) was heated to 70° C. After being stirred for two days, the mixture was cooled, diluted with ethyl acetate (200 mL), washed with water (5×8 ml), brine (20 mL), dried over anhydrous Na₂SO₄ and filtered. The organic layer was concentrated and the residue was purified by prep-TLC (eluting with EA/PE=5/1) to give tert-butyl 9-((3-chloro-4-(methoxycarbonyl)phenyl)thio)-3-azaspiro[5.5]undecane-3-carboxylate. LRMS m/z (M+Na) 476.1 found, 476.2 required.

tert-butyl 9-(3-chloro-4-(methoxycarbonyl)phenylsulfinyl)-3-azaspiro[5.5]undecane-3-carboxylate To a solution of tert-butyl 9-((3-chloro-4-(methoxycarbonyl)phenyl)thio)-3-azaspiro[5.5]undecane-3-carboxylate (24 mg, 0.053 mmol) in DCM (3 ml) was added m-CPBA (9.12 mg, 0.053 mmol) at 0° C. After being stirred for several hours, the mixture was diluted with dichloromethane (150 mL), washed with aqueous sodium hydrogen carbonate (10 mL), brine (20 ml), dried over anhydrous Na₂SO₄ and filtered. The organic layer was concentrated and the residue was purified by prep-TLC (silica gel, eluting with PE:EA=5:1) to give tert-butyl 9-((3-chloro-4-(methoxycarbonyl)phenyl)sulfinyl)-3-azaspiro[5.5]undecane-3-carboxylate. LRMS m/z (M-55) 414.1 found, 414.2 required.

Methyl 4-(3-azaspiro[5.5]undecan-9-ylsulfinyl)-2-chlorobenzoate

To a solution of tert-butyl 9-((3-chloro-4-(methoxycarbonyl)phenyl)sulfinyl)-3-azaspiro[5.5]undecane-3-carboxylate (23 mg, 0.049 mmol) in DCM (8 ml) was added TFA (0.8 ml, 10.38 mmol) at 0° C. After being stirred for 2 h, the mixture was diluted with dichloromethane (150 mL), washed with aqueous sodium hydrogen carbonate (10 mL), dried over anhydrous Na₂SO₄ and filtered. The organic layer was concentrated to give methyl 4-(3-azaspiro[5.5]undecan-9-ylsulfinyl)-2-chlorobenzoate. LRMS m/z (M+H) 369.8 found, 370.1 required.

Methyl 2-chloro-4-(3-((R or S)-2-(3,5-dichlorophenyl)-3,3,3-trifluoro-2-hydroxypropanoyl)-3-azaspiro[5.5]undecan-9-ylsulfinyl)benzoate To a solution of (R or S)-2-(3,5-dichlorophenyl)-3,3,3-trifluoro-2-hydroxypropanoic acid (28 mg, 0.097 mmol) and HATU (37 mg, 0.097 mmol) in 0.5 ml of DMF was added a solution of methyl 4-(3-azaspiro[5.5]undecan-9-ylsulfinyl)-2-chlorobenzoate (18 mg, 0.049 mmol) and DIPEA (0.018 ml, 0.101 mmol) in 0.5 ml of DMF at 0° C. After being stirred overnight, the mixture was diluted with ethyl acetate (200 mL), washed with water (8×5 mL), dried over anhydrous Na₂SO₄ and filtered. The organic layer was concentrated and the residue was purified by prep-TLC (PE:EA=5:1) to give methyl 2-chloro-4-((3-((R or S)-2-(3, 5-dichlorophenyl)-3,3,3-trifluoro-2-hydroxypropanoyl)-3-azaspiro[5.5]undecan-9-yl)sulfinyl)benzoate. LRMS m/z (M+H) 639.8 found, 640.1 required.

2-chloro-4-(3-((R or S)-2-(3,5-dichlorophenyl)-3,3,3-trifluoro-2-hydroxypropanoyl)-3-azaspiro[5.5]undecan-9-ylsulfinyl)benzoic acid To a solution of methyl 2-chloro-4-((3-((R or S)-2-(3,5-dichlorophenyl)-3,3,3-trifluoro-2-hydroxypropanoyl)-3-azaspiro[5.5]undecan-9-yl)sulfinyl)benzoate (23 mg, 0.036 mmol) in THF (5 ml) was added 1M lithium hydroxide (6 ml, 6.00 mmol) at room temperature. The reaction was heated to 50° C. for several hours. The mixture was cooled and the solvent was removed under reduced pressure. The residue was acidified with hydrochloric acid (2M) to pH=2-3, extracted with ethyl acetate (3×20 mL). The combined organic fractions were washed with brine (10 mL), dried over anhydrous $Na_2SO_4$, filtered and concentrated to give sulfinyl)benzoic acid (16 mg, 0.026 mmol) in 0.5 ml of DMF was added a solution of DIPEA (7 mg, 0.054 mmol) in 0.5 ml of DMF and dimethylamine hydrochloride (20 mg, 0.26 mmol) at 0° C. The reaction was stirred overnight. The mixture was diluted with ethyl acetate (100 mL), washed with water (6×8 mL), dried over anhydrous $Na_2SO_4$, filtered and concentrated. The residue was purified by prep-TLC (eluting with EA) to give 2-chloro-4-((3-((R or S)-2-(3,5-dichlorophenyl)-3,3,3-trifluoro-2-hydroxypropanoyl)-3-azaspiro[5.5]undecan-9-yl)sulfinyl)-N,N-dimethylbenzamide. LRMS m/z (M+H) 652.8 found, 653.1 required.

Example 21-1

2-chloro-4-(3-((R or S)-2-(3,5-dichlorophenyl)-3,3,3-trifluoro-2-hydroxypropanoyl)-3-azaspiro[5.5]undecan-9-ylsulfonyl)-N,N-dimethylbenzamide

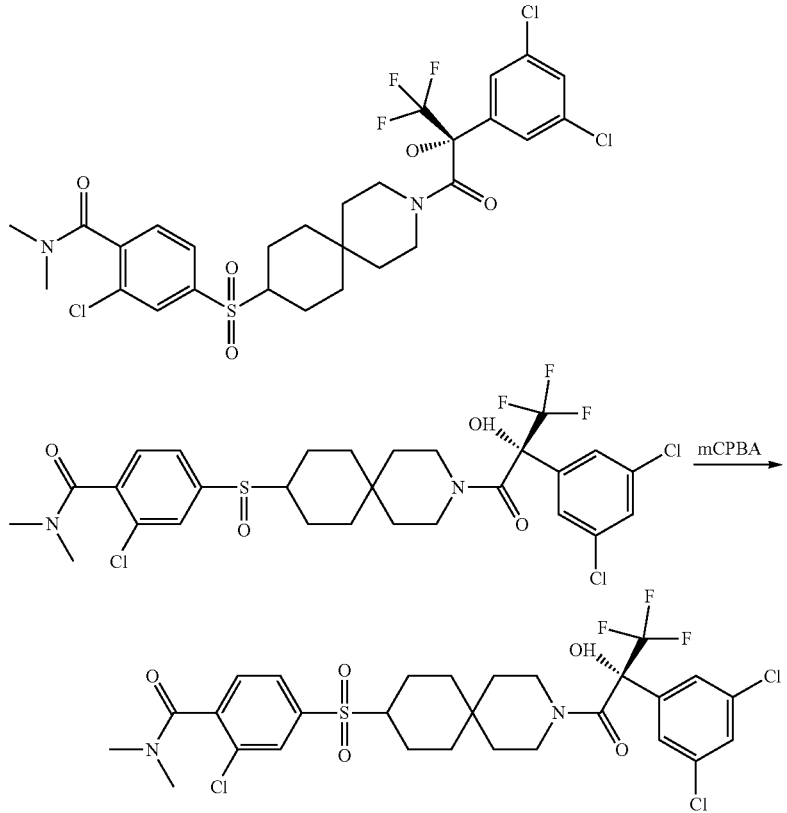

2-chloro-4-((3-((R or S)-2-(3,5-dichlorophenyl)-3,3,3-trifluoro-2-hydroxypropanoyl)-3-azaspiro[5.5]undecan-9-yl)sulfinyl)benzoic acid. LRMS m/z (M+H) 626.0 found, 626.0 required.

2-chloro-4-(3-((R or S)-2-(3,5-dichlorophenyl)-3,3,3-trifluoro-2-hydroxypropanoyl)-3-azaspiro[5.5]undecan-9-ylsulfinyl)-N,N-dimethylbenzamide To a solution of HATU (19 mg, 0.050 mmol) and 2-chloro-4-((3-((R or S)-2-(3,5-dichlorophenyl)-3,3,3-trifluoro-2-hydroxypropanoyl)-3-azaspiro[5.5]undecan-9-yl)

2-chloro-4-(3-((R or S)-2-(3,5-dichlorophenyl)-3,3,3-trifluoro-2-hydroxypropanoyl)-3-azaspiro[5.5]undecan-9-ylsulfonyl)-N,N-dimethylbenzamide To a solution of 2-chloro-4-((3-((R or S)-2-(3,5-dichlorophenyl)-3,3,3-trifluoro-2-hydroxypropanoyl)-3-azaspiro[5.5]undecan-9-yl)sulfinyl)-N,N-dimethylbenzamide (6 mg, 9.17 μmol) in DCM (2 ml) was added m-CPBA (1.6 mg, 9.17 μmol) at 0° C. The reaction was stirred overnight, and quenched with aqueous sodium hydrogen carbonate (10 mL), extracted with ethyl acetate (3×30 mL). The combined organic fractions were washed with brine (10 mL), dried over anhydrous Na₂SO₄, filtered and concentrated. The residue was purified by prep-TLC (PE/EA=2/1) to give (R or S)-2-chloro-4-((3-(2-(3,5-dichlorophenyl)-3,3,3-trifluoro-2-hydroxypropanoyl)-3-azaspiro[5.5]undecan-9-yl)sulfonyl)-N,N-dimethylbenzamide. LRMS m/z (M+H) 668.8 found, 669.0 required.

Example 22-1

2-chloro-N,N-dimethyl-4-(4-(1-(2-methyl-2-phenyl-propanoyl)piperidin-4-yl)butylsulfonyl)benzamide

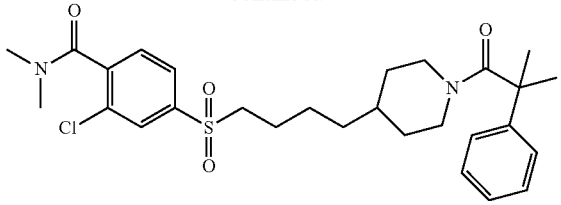

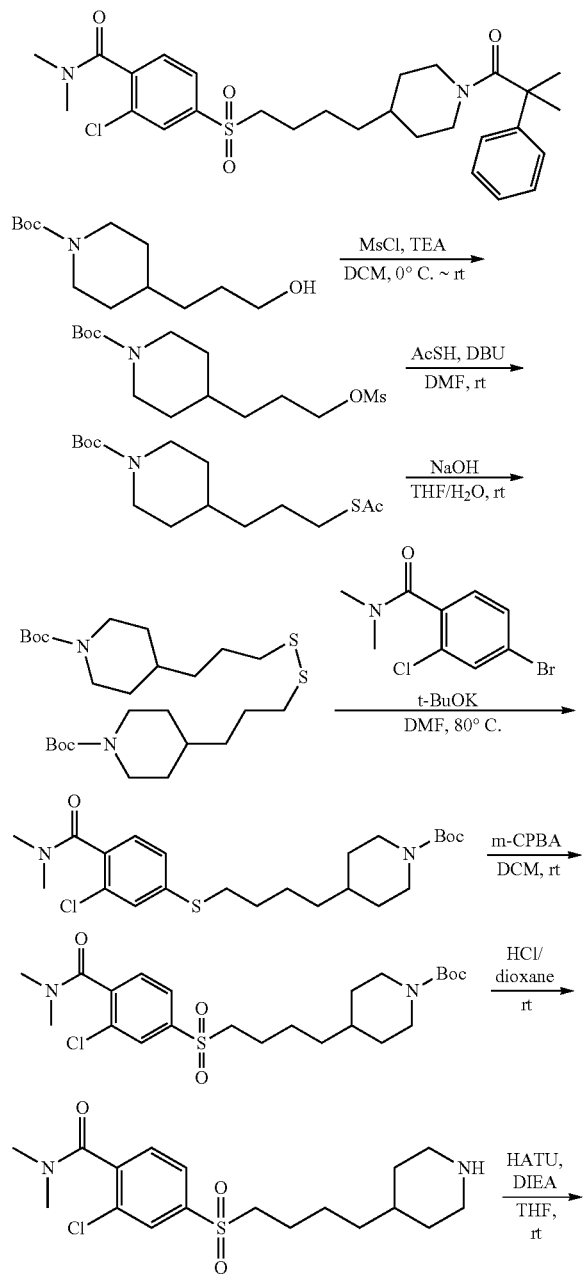

tert-butyl 4-(3-(methylsulfonyloxy)propyl)piperidine-1-carboxylate

To a solution of tert-butyl 4-(3-hydroxypropyl)piperidine-1-carboxylate (500 mg, 2.06 mmol) in DCM (10 mL) was added TEA (416 mg, 4.12 mmol) and MsCl (282 mg, 2.47 mmol) at 0° C. The mixture was stirred at 0° C. to rt for 6 h. Then the mixture was directly purified by column chromatography (silica gel: 300-400 mesh, PE/EtOAc=8/1) to afford tert-butyl 4-(3-(methylsulfonyloxy)propyl)piperidine-1-carboxylate. LRMS m/z (M+H) 322.1 found, 322.2 required.

tert-butyl 4-(3-(acetylthio)propyl)piperidine-1-carboxylate

To a solution of tert-butyl 4-(3-(methylsulfonyloxy)propyl)piperidine-1-carboxylate (630 mg, 1.96 mmol) in DMF (6 mL) was added AcSH (298 mg, 3.92 mmol) and DBU (447 mg, 2.94 mmol). The mixture was stirred at rt overnight. Then the mixture was concentrated and the residue was directly purified by reverse phase HPLC (mobile phase: methanol/water (10 mM NH₄HCO₃) to afford tert-butyl 4-(3-(acetylthio)propyl)piperidine-1-carboxylate. LRMS m/z (M+H) 302.2 found, 302.2 required.

tert-butyl 4,4'-(3,3'-disulfanediylbis(propane-3,1-diyl))dipiperidine-1-carboxylate To a solution of tert-butyl 4-(3-(acetylthio)propyl)piperidine-1-carboxylate (420 mg, 1.40 mmol) in THF (4 mL) and water (4 ml) was added NaOH (112 mg, 2.80 mmol). The mixture was stirred at rt overnight. Then the mixture was concentrated and the residue was directly purified by reverse phase HPLC (mobile phase: methanol/water (10 mM NH₄HCO₃) to afford tert-butyl 4,4'-(3,3'-disulfanediylbis(propane-3,1-diyl))dipiperidine-1-carboxylate. LRMS m/z (M+H) 517.2 found, 517.3 required.

tert-butyl 4-(4-(3-chloro-4-(dimethylcarbamoyl)phenylthio)butyl)piperidine-1-carboxylate To a solution of tert-butyl 4,4'-(3,3'-disulfanediylbis(propane-3,1-diyl))dipiperidine-1-carboxylate (350 mg, 0.68 mmol) in DMF (5 mL) was added 4-bromo-2-chloro-N,N-dimethylbenzamide (267 mg, 1.02 mmol) and t-BuOK (114 mg, 1.02 mmol). The mixture was heated to 80° C. overnight. Then the mixture was filtered and the filtrate was directly purified by reverse phase HPLC (mobile phase: methanol/water (10 mM NH₄HCO₃) to afford tert-butyl 4-(4-(3-chloro-4-(dimethylcarbamoyl)phenylthio)butyl)piperidine-1-carboxylate. LRMS m/z (M+H) 455.2 found, 455.2 required.

tert-butyl 4-(4-(3-chloro-4-(dimethylcarbamoyl)phenylsulfonyl)butyl)piperidine-1-carboxylate To a solution of tert-butyl 4-(4-(3-chloro-4-(dimethylcarbamoyl)phenylthio)butyl)piperidine-1-carboxylate (260 mg, 0.57 mmol) in DCM (4 mL) was added m-CPBA (196 mg, 1.14 mmol) at 0° C. The mixture was stirred at 0° C. to rt for 2 h. Then the mixture was filtered and the filtrate was concentrated. The residue was directly purified by reverse phase HPLC (mobile phase: methanol/water (10 mM $NH_4HCO_3$) to afford tert-butyl 4-(4-(3-chloro-4-(dimethyl-carbamoyl)phenylsulfonyl)butyl)piperidine-1-carboxylate. LRMS m/z (M+H) 487.2 found, 487.2 required.

2-chloro-N,N-dimethyl-4-(4-(piperidin-4-yl)bu-tylsulfonyl)benzamide

To a solution of tert-butyl 4-(4-(3-chloro-4-(dimethylcar-bamoyl)phenylsulfonyl)butyl)piperidine-1-carboxylate (110 mg, 0.23 mmol) in THF (1 mL) was added HCl/1,4-dioxane (4 mL, 16 mmol, 4M). The mixture was stirred at rt for 2 h and concentrated in vacuo to afford the crude product 2-chloro-N,N-dimethyl-4-(4-(piperidin-4-yl)butylsulfonyl) benzamide. LRMS m/z (M+H) 387.1 found, 387.1 required.

2-chloro-N,N-dimethyl-4-(4-(1-(2-methyl-2-phenyl-propanoyl)piperidin-4-yl)butylsulfonyl)benzamide To a solution of 2-chloro-N,N-dimethyl-4-(4-(piperidin-4-yl)butylsulfonyl)benzamide (30 mg, 0.078 mmol) in THF (1 mL) was added 2-methyl-2-phenylpropanoic acid (20 mg, 0.12 mmol), DIEA (30 mg, 0.23 mmol) and HATU (46 mg, 0.12 mmol). The mixture was stirred at rt overnight. Then the mixture was directly purified by reverse phase HPLC (mobile phase: methanol/water (10 mM $NH_4HCO_3$) to afford 2-chloro-N,N-dimethyl-4-(4-(1-(2-methyl-2-phenyl-propanoyl)piperidin-4-yl)butylsulfonyl)benzamide. LRMS m/z (M+H) 533.1 found, 533.2 required.

Example 23-1

2-chloro-N,N-dimethyl-4-(((1R,2R or 1S,2S)-2-(1-((R or S)-3,3,3-trifluoro-2-hydroxy-2-(3-methoxy-phenyl)propanoyl)piperidin-4-yl)cyclopropyl)meth-ylthio)benzamide

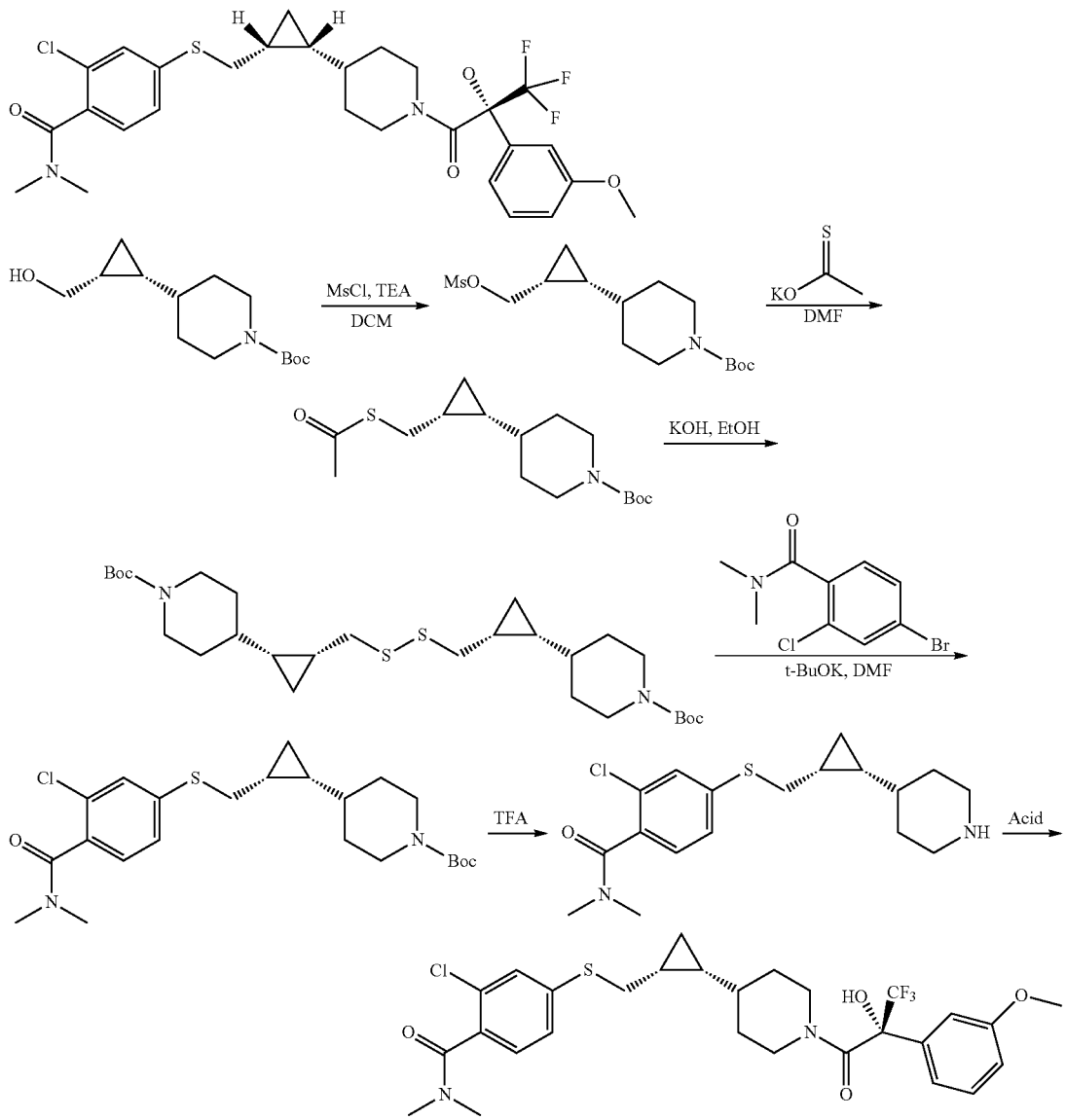

tert-butyl 4-((1R,2R or 1S,2S)-2-((methylsulfonyloxy)methyl)cyclopropyl)piperidine-1-carboxylate To a solution of tert-butyl 4-((1R,2R or 1S,2S)-2-(hydroxymethyl)cyclopropyl)piperidine-1-carboxylate (500 mg, 1.96 mmol) in DCM (5 mL) was added methanesulfonyl chloride (336 mg, 2.93 mmol) and TEA (600 mg, 5.94 mmol). The reaction mixture was stirred overnight at RT, quenched with water (5 mL) and extracted with EtOAc (3×10 mL). The organic layer was dried over anhydrous $Na_2SO_4$ and concentrated to give tert-butyl 4-((1R,2R or 1S,2S)-2-((methylsulfonyloxy)methyl)cyclopropyl)piperidine-1-carboxylate. LRMS m/z (M-55) 278.1 found, 278.2 required.

tert-butyl 4-((1R,2R or 1S,2S)-2-(acetylthiomethyl)cyclopropyl)piperidine-1-carboxylate A mixture of tert-butyl 4-((1R,2R or 1S,2S)-2-((methylsulfonyloxy)methyl)cyclopropyl)piperidine-1-carboxylate (600 mg, 1.8 mmol) and potassium ethanethioate (308 mmol, 2.7 mmol) in DMF (5 mL) was stirred for 2 h at 60° C. After being cooled to rt, EtOAc (20 mL) was added. The organic layer was washed with water (3×5 mL), drived over anhydrous $Na_2SO_4$ and concentrated to give tert-butyl 4-((1R,2R or 1S,2S)-2-(acetylthiomethyl)cyclopropyl)piperidine-1-carboxylate. LRMS m/z (M-99) 214.3 found, 214.2 required.

tert-butyl 4,4'-(1R,1'R,2R,2'R)-2,2'-disulfanediylbis(methylene)bis(cyclopropane-2,1-diyl)dipiperidine-1-carboxylate A mixture of tert-butyl 4-((1R,2R or 1S,2S)-2-(acetylthiomethyl)cyclopropyl)piperidine-1-carboxylate (400 mg, 1.28 mmol) and 20% potassium hydroxide (5 mL) in EtOH (5 mL) was stirred overnight at 80° C. Then the mixture was concentrated and purified by reverse phase HPLC (mobile phase: methanol/water (10 mM $NH_4HCO_3$)) to afford tert-butyl 4,4'-(1R,1'R,2R,2'R)-2,2'-disulfanediylbis(methylene)bis(cyclopropane-2,1-diyl)dipiperidine-1-carboxylate. LRMS m/z (M+23) 563.3 found, 563.3 required.

tert-butyl 4-((1R,2R or 1S,2S)-2-((3-chloro-4-(dimethylcarbamoyl)phenylthio)methyl)cyclopropyl)piperidine-1-carboxylate A mixture of tert-butyl 4,4'-(1R,1'R,2R,2'R)-2,2'-disulfanediylbis(methylene)bis(cyclopropane-2,1-diyl)dipiperidine-1-carboxylate (80 mg, 0.15 mmol) and 4-bromo-2-chloro-N,N-dimethylbenzamide (42 mg, 0.16 mmol) and potassium tert-butylate (150 mg, 0.45 mmol) in DMF (2 mL) was stirred for 1 h at 120° C. under microwave irradiation. Then the mixture was directly purified by reverse phase HPLC (mobile phase: methanol/water (10 mM $NH_4HCO_3$)) to afford tert-butyl 4-((1R,2R or 1S,2S)-2-((3-chloro-4-(dimethylcarbamoyl)phenylthio)methyl)cyclopropyl)piperidine-1-carboxylate. LRMS m/z (M+23) 475.2 found, 475.2 required.

2-chloro-N,N-dimethyl-4-(((1R,2R or 1S,2S)-2-(piperidin-4-yl)cyclopropyl)methylthio)benzamide A mixture of tert-butyl 4-((1R,2R or 1S,2S)-2-((3-chloro-4-(dimethylcarbamoyl)phenylthio)methyl)cyclopropyl)piperidine-1-carboxylate (100 mg, 0.22 mmol) and TFA (1 mL) in DCM (1 mL) was stirred for 2 h at RT. Then the mixture was concentrated to give 2-chloro-N,N-dimethyl-4-(((1R,2R or 1S,2S)-2-(piperidin-4-yl)cyclopropyl)methylthio)benzamide. LRMS m/z (M+H) 353.2 found, 353.1 required.

2-chloro-N,N-dimethyl-4-(((1R,2R or 1S,2S)-2-(1-((R or S)-3,3,3-trifluoro-2-hydroxy-2-(3-methoxyphenyl)propanoyl)piperidin-4-yl)cyclopropyl)methylthio)benzamide A mixture of 2-chloro-N,N-dimethyl-4-(((1R,2R or 1S,2S)-2-(piperidin-4-yl)cyclopropyl)methylthio)benzamide (30 mg, 0.09 mmol), (R or S)-3,3,3-trifluoro-2-hydroxy-2-(3-methoxyphenyl)propanoic acid (26 mg, 0.10 mmol), HATU (42 mg, 0.11 mmol) and DIEA (39 mg, 0.3 mmol) in DMF (1 mL) was stirred at RT overnight. The mixture was directly purified by reverse phase HPLC (mobile phase: methanol/water (10 mM $NH_4HCO_3$)) to afford 2-chloro-N,N-dimethyl-4-(((1R,2R or 1S,2S)-2-(1-((R or S)-3,3,3-trifluoro-2-hydroxy-2-(3-methoxyphenyl)propanoyl)piperidin-4-yl)cyclopropyl)methylthio)benzamide. LRMS m/z (M+H) 585.2 found, 585.2 required.

Biological Assays

Potency (Inflection Point, IP) and efficacy (Emax) are evaluated via compound-induced co-activator recruitment to glutathione-S-transferase (GST) tagged LXRbeta and LXRalpha LBD (ligand binding domain) proteins in relation to reference dual agonist compound T0901317 (N-(2,2,2-Trifluoroethyl)-N-[4-[2,2,2-trifluoro-1-hydroxy-1-(trifluoromethyl)ethyl]phenyl]benzenesulfonamide) using the LanthaScreen™ TR-FRET Liver X Receptor Coactivator Assays according to manufacturer's instructions (Invitrogen catalog number pv4658.pps and pv4655). While running the LanthaScreen™ TR-FRET Liver X Receptor Coactivator Assay, LXR alpha-LBD or LXR beta-LBD was added to ligand test compounds followed by addition of a mixture of a fluorescein-labelled coactivator peptide and terbium-conjugated anti-GST antibody. After an incubation period at room temperature, TR-FRET (time-resolved fluorescence resonance energy transfer) was measured using a filter-based instrument capable of TR-FRET, e.g. PerkinElmer Envision. When the terbium label on the anti-GST antibody was excited at 340 nm, energy was transferred to the fluorescein label on the coactivator peptide and detected as emission at 520 nm, providing an indication of ligand binding that enables ligand-dependent recruitment of coactivator peptide, and the ratio of 520 nm:495 nm is calculated and is used to determine the ligands potencies and efficacies from appropriate dose response curves of the compound. IP and % Emax values for each of the example compounds of the invention were measured in accordance with the above and are provided in the Table below.

| Example | LXR beta IP (nM) | LXR beta actiivty at max dose (%) | LXR alpha IP (nM) | LXR alpha actiivty at max dose (%) |
| --- | --- | --- | --- | --- |
| 1-1 | 8 | 68 | 577 | 17 |
| 1-2 | 15 | 59 | 266 | 43 |
| 1-3 | 9 | 75 | 481 | 38 |
| 1-4 | 183 | 42 | No IP | 2 |
| 1-5 | 8 | 72 | 239 | 32 |
| 1-6 | 102 | 63 | 3298 | 16 |
| 1-7 | 14 | 56 | 3160 | 19 |
| 1-8 | 4 | 52 | No IP | 12 |
| 1-9 | 17 | 62 | No IP | 13 |
| 1-10 | 14 | 68 | 2090 | 19 |
| 1-11 | 3 | 29 | No IP | 0 |
| 1-12 | 27 | 82 | 855 | 46 |

-continued

| Example | LXR beta IP (nM) | LXR beta actiivty at max dose (%) | LXR alpha IP (nM) | LXR alpha actiivty at max dose (%) |
|---|---|---|---|---|
| 1-13 | 104 | 21 | No IP | 12 |
| 1-14 | 106 | 41 | 1974 | 14 |
| 1-15 | 3 | 72 | 147 | 43 |
| 2-1 | 29 | 52 | 1247 | 25 |
| 3-1 | 47 | 109 | 1152 | 16 |
| 4-1 | 13 | 71 | 734 | 22 |
| 4-2 | 7 | 84 | 382 | 37 |
| 4-3 | 15 | 79 | 653 | 35 |
| 4-4 | 325 | 59 | No IP | 7 |
| 4-5 | 3769 | 17 | No IP | 0 |
| 5-1 | 5 | 41 | 220 | 56 |
| 6-1 | 15 | 30 | 828 | 21 |
| 6-2 | 8 | 56 | 472 | 11 |
| 6-3 | 14 | 49 | 1404 | 24 |
| 6-4 | 34 | 18 | No IP | 6 |
| 6-5 | 49 | 24 | 2145 | 19 |
| 6-6 | 49 | 43 | No IP | 0 |
| 6-7 | 68 | 91 | No IP | 9 |
| 6-8 | 9 | 91 | 829 | 65 |
| 6-9 | 21 | 60 | 869 | 64 |
| 7-1 | 59 | 103 | 683 | 28 |
| 8-1 | 7 | 21 | No IP | 0 |
| 8-2 | 14 | 75 | 516 | 34 |
| 8-3 | 4 | 50 | 421 | 35 |
| 9-1 | 29 | 80 | 797 | 22 |
| 10-1 | 73 | 54 | No IP | 12 |
| 11-1 | 8 | 85 | No IP | 12 |
| 12-1 | 430 | 34 | No IP | 5 |
| 13-1 | 6 | 57 | 321 | 39 |
| 14-1 | 1263 | 99 | 15490 | 33 |
| 15-1 | 46 | 41 | 1309 | 19 |
| 15-2 | 28 | 95 | 623 | 20 |
| 15-3 | 31 | 116 | 846 | 36 |
| 15-4 | 32 | 103 | 463 | 39 |
| 15-5 | 16 | 75 | 516 | 22 |
| 15-6 | 6 | 96 | 381 | 27 |
| 15-7 | 6 | 93 | 327 | 40 |
| 15-8 | 9 | 79 | 236 | 29 |
| 15-9 | 240 | 84 | No IP | 4 |
| 16-1 | 132 | 100 | 1542 | 19 |
| 16-2 | 59 | 113 | 772 | 29 |
| 16-3 | 56 | 108 | 423 | 50 |
| 16-4 | 58 | 96 | No IP | 8 |
| 17-1 | 12 | 51 | No IP | 0 |
| 17-2 | 25 | 128 | 395 | 35 |
| 17-3 | 19 | 43 | No IP | 8 |
| 18-1 | 72 | 65 | 739 | 21 |
| 19-1 | 58 | 101 | 1057 | 23 |
| 19-2 | 38 | 74 | No IP | 8 |
| 19-3 | 136 | 95 | No IP | 0 |
| 20-1 | 938 | 50 | No IP | 0 |
| 21-1 | 1456 | 50 | No IP | 0 |
| 22-1 | 1985 | 57 | No IP | 2 |
| 23-1 | 27 | 118 | 946 | 24 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

We claim:

1. A compound having the structural Formula (I):

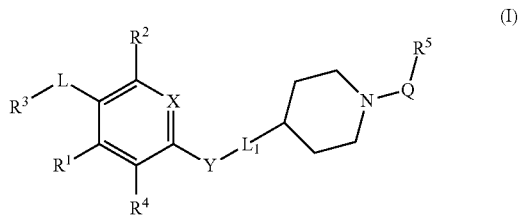

or a pharmaceutically acceptable salt thereof, wherein:

X is selected from CH and N;

Y is selected from NH, N(CH$_3$), S, S(O), S(O)$_2$ and CH$_2$;

R$^1$ is selected from H, methyl, and halogen;

R$^2$ is selected from H, halogen, cyano, cyclopropyl, —CH$_3$, and —OCH$_3$;

R$^4$ is selected from H, halogen, and methyl;

-L- is selected from —C(O)— and —S(O)$_2$—;

R$^3$ is —N(R$^{N1}$)(R$^{N2}$), wherein:

R$^{N1}$ is selected from H and —(C$_1$-C$_6$)alkyl; and

R$^{N2}$ is selected from H, —(C$_1$-C$_6$)alkyl, cyclopropyl, —O—(C$_1$-C$_6$)alkyl, —OH, halogen, —CN, and —(C$_1$-C$_6$)alkyl which is substituted with 1 or 2 groups independently selected from:

—OH, halogen, —CN, optionally substituted phenyl, (wherein said optional substitutents on said phenyl are 1 to 3 groups independently selected from OH, CN, —(C$_1$-C$_4$)alkyl, and —(C$_1$-C$_4$)alkoxyl), optionally substituted heteroaryl, (wherein said optional substituents on said heteroaryl are 1 to 3 groups independently selected from —(C$_1$-C$_6$)alkyl, —(C$_1$-C$_4$)alkoxyl, and cyclopropyl), optionally substituted cyclopropyl (wherein said optional substituents on said cyclopropyl are 1 to 3 groups independently selected from —(C$_1$-C$_6$)alkyl), and optionally substituted heterocycloalkyl (wherein said optional substitutents on said heterocycloalkyl are 1 to 3 groups independently selected from halogen, —OH, oxo, CN, and —(C$_1$-C$_6$)alkyl), or, alternatively, R$^{N1}$ and R$^{N2}$ are taken together with the nitrogen atom to which they are shown attached to form a 4-, 5-, or 6-membered fully saturated heterocyclic ring comprising (including the nitrogen atom) 1, 2, or 3 ring heteroatoms selected from N, N-oxide, O, S, and S-oxide, wherein said heterocyclic ring is unsubstituted or substituted with 1, 2, or 3 substituents independently selected from halogen, —OH, oxo, CN, —(C$_1$-C$_6$)alkyl, amino-substituted —(C$_1$-C$_6$)alkyl (wherein said amino is 1, 2, or 3 groups independently selected from —NH$_2$, —N(C$_1$-C$_4$alkyl)$_2$, —NH(C$_1$-C$_4$alkyl)), —O—(C$_1$-C$_6$)alkyl, —(C$_1$-C$_6$)alkyl-OH, —(C$_1$-C$_6$)haloalkyl, —C(O)O—(C$_1$-C$_6$)alkyl, cyclopropyl, spirocyclopropyl, —CH$_2$—NHC(O)O—(C$_1$-C$_6$)alkyl, —CH$_2$—N(CH$_3$)C(O)O—(C$_1$-C$_6$)alkyl, phenyl, benzyl, —NHC(O)-phenyl, heteroaryl, (C$_1$-C$_4$)alkylheteroaryl, and heterocycloalkyl;

-L₁- is a divalent moiety selected from:

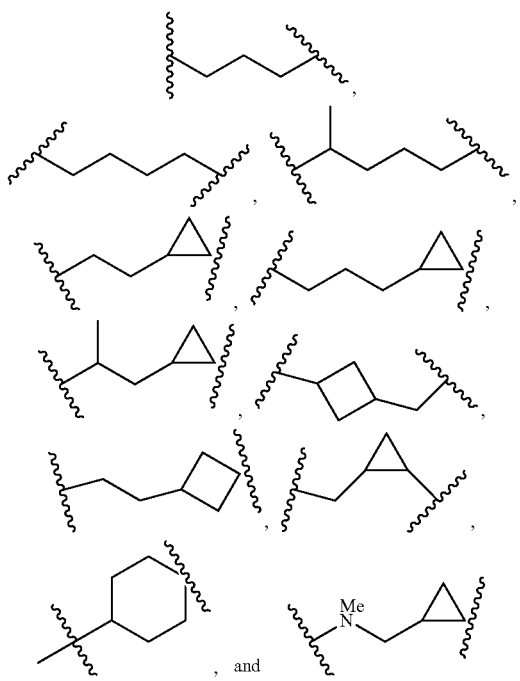

Q is a bond or a divalent moiety selected from —C(O)—, and —S(O)₂—, and—

R⁵ is —C(R⁵ᴬ)(R⁵ᴮ)(R⁵ᶜ), wherein:
each of R⁵ᴬ, R⁵ᴮ and R⁵ᶜ is independently selected from: H, halogen, OH, NH₂, NHCH₃, —(C₁-C₆)alkyl, —(C₁-C₆)haloalkyl, —(C₁-C₆)alkenyl, —(C₁-C₆)alkynyl, —(C₃-C₆)cycloalkyl, —(C₃-C₆)cycloalkyl substituted with —(C₁-C₆)alkyl, —(C₁-C₆)alkenyl, —(C₁-C₆)alkynyl, phenyl, and phenyl substituted with from 1 to 3 groups independently selected from halogen, OH, —NH₂, —(C₁-C₆)alkyl, —O—(C₁-C₆)alkyl, cyclopropyl, —O—(C₁-C₆)haloalkyl, —O-cyclopropyl, and —C(O)O—(C₁-C₆)alkyl,
or R⁵ is

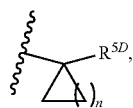

wherein n is an integer from 1 to 4;
wherein R⁵ᴰ is selected from H, —(C₁-C₆)alkyl, —(C₁-C₆)haloalkyl, phenyl, and phenyl substituted with from 1 to 3 groups independently selected from OH, halogen, —(C₁-C₆)alkyl, and —O—(C₁-C₆)alkyl,
or R⁵ is selected from phenyl and benzyl, wherein:
said phenyl and said benzyl are unsubstituted or substituted with 1, 2, or 3 groups independently selected from halogen, CN, —(C₁-C₆)alkyl, and —(C₁-C₆)haloalkyl.

2. The compound of claim 1, or a pharmaceutically acceptable salt thereof, wherein X is CH.

3. The compound of claim 1, or a pharmaceutically acceptable salt thereof, wherein X is N.

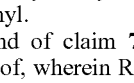

4. The compound of claim 1, or a pharmaceutically acceptable salt thereof, wherein R³ is —N(Rᴺ¹)(Rᴺ²), wherein:
Rᴺ¹ is selected from H, methyl, and ethyl; and
Rᴺ² is H, methyl, ethyl, —O-methyl, —O-ethyl, OH, fluoro, chloro, —CN, substituted methyl, or substituted ethyl, wherein each said substituent is 1 or 2 groups independently selected from:
OH, fluoro, chloro, —CN,
optionally substituted phenyl, (wherein said optional substitutents on said phenyl are 1 to 3 groups independently selected from OH, CN, methyl, ethyl, —O-methyl, and —O-ethyl),
optionally substituted heteroaryl, (wherein said optional substituents on said heteroaryl are 1 to 3 groups independently selected from methyl, ethyl, —O-methyl, —O-ethyl, and cyclopropyl),
optionally substituted cyclopropyl (wherein said optional substituents on said cyclopropyl are 1 to 3 groups independently selected from methyl and ethyl),
optionally substituted heterocycloalkyl (wherein said optional substituents on said heterocycloalkyl are 1 to 3 groups independently selected from halogen, —OH, oxo, CN, methyl, and ethyl, —O-methyl, —O— ethyl, —OH, F, Cl, and —CN).

5. The compound of claim 4, or a pharmaceutically acceptable salt thereof, wherein R¹ is selected from H, methyl, F, and Cl.

6. The compound of claim 5, or a pharmaceutically acceptable salt thereof, wherein R² is selected from H, Cl, cyano, cyclopropyl, —CH₃, and —OCH₃.

7. The compound of claim 6, or a pharmaceutically acceptable salt thereof, wherein R⁴ is selected from H, —CH₃, and chloro.

8. The compound of claim 7, or a pharmaceutically acceptable salt thereof, wherein R⁵ is-C(R⁵ᴬ)(R⁵ᴮ)(R⁵ᶜ),
wherein each of R⁵ᴬ, R⁵ᴮ and R⁵ᶜ is independently selected from H, F, Cl, OH, NH₂, NHCH₃, —(C₁-C₆)alkyl, —(C₁-C₆)haloalkyl, —(C₁-C₆)alkenyl, —(C₁-C₆)alkynyl, —(C₃-C₆)cycloalkyl, —(C₃-C₆)cycloalkyl substituted with —(C₁-C₆)alkyl, —(C₁-C₆)alkenyl, —(C₁-C₆)alkynyl, phenyl, phenyl substituted with from 1 to 3 groups independently selected from F, Cl, —(C₁-C₆)alkyl, —O—(C₁-C₆)alkyl, and —C(O)O—(C₁-C₆)alkyl.

9. The compound of claim 7 wherein R⁵ is wherein n is an integer from 1 to 4; and R⁵ᴰ is selected from H, —(C₁-C₆)alkyl, —(C₁-C₆)haloalkyl, phenyl, and phenyl substituted with from 1 to 3 groups independently selected from OH, F, Cl, methyl, ethyl, n-propyl, i-propyl, —O-methyl, and —O-ethyl.

10. The compound of claim 7, or a pharmaceutically acceptable salt thereof, wherein R⁵ is selected from phenyl and benzyl, wherein said phenyl and said benzyl are unsubstituted or substituted with 1, 2, or 3 groups independently selected from halogen, CN, —(C₁-C₆)alkyl, and —(C₁-C₆)haloalkyl.

11. The compound of claim 1, or a pharmaceutically acceptable salt thereof, said compound selected from:

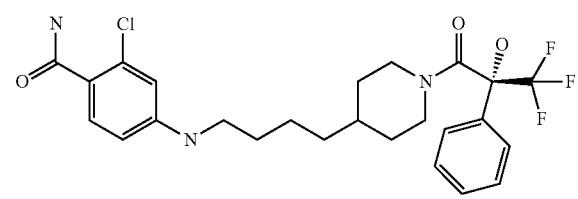
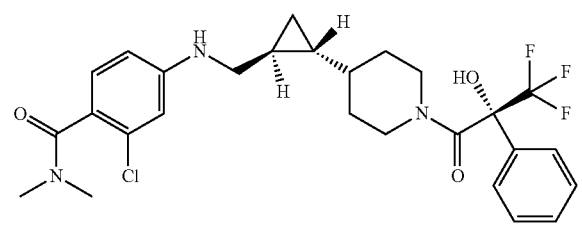
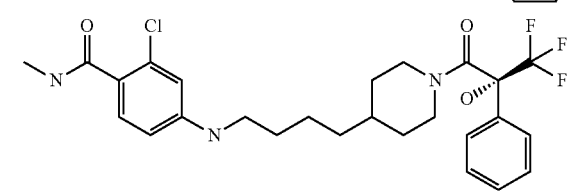
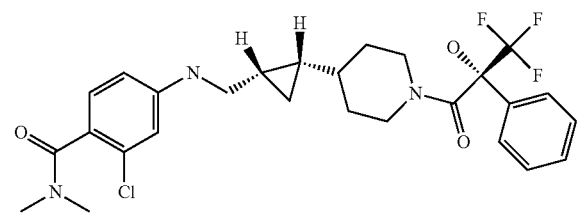
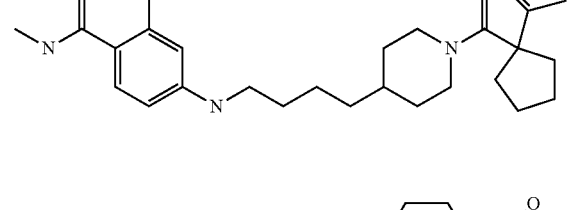
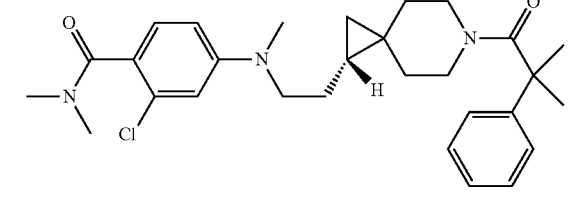
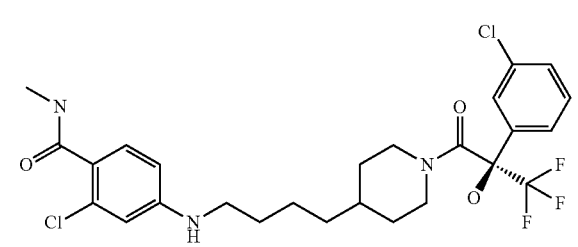
-continued
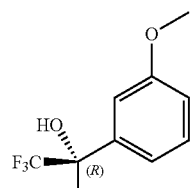
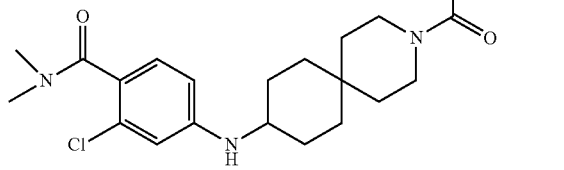
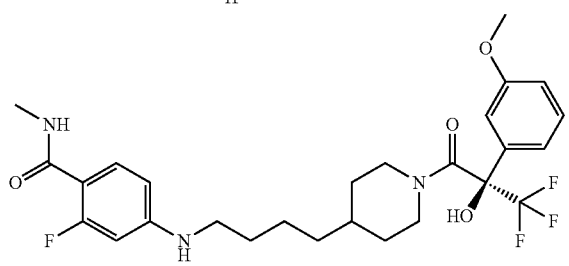
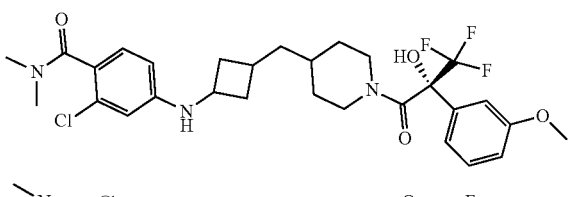
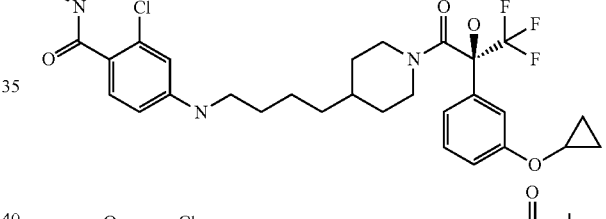
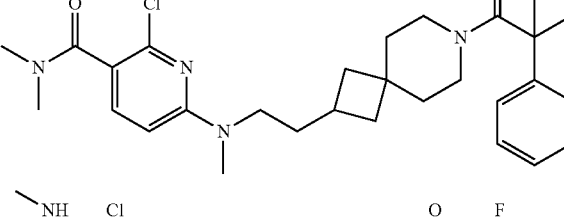
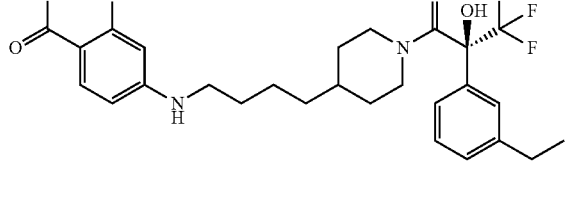
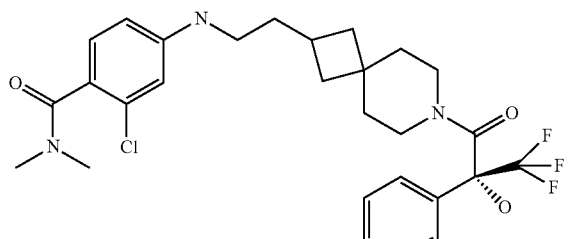

117
-continued
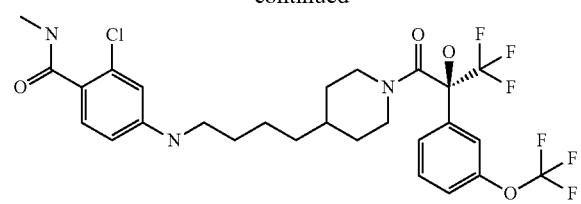
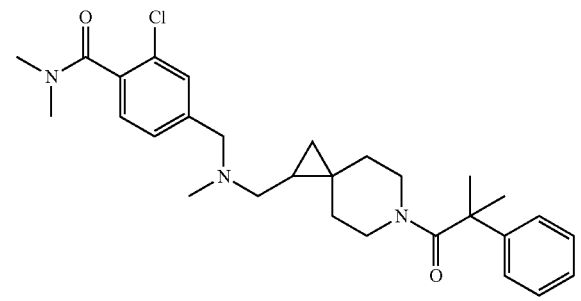
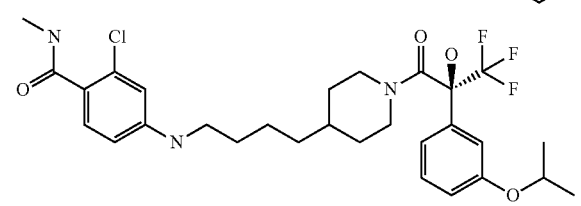
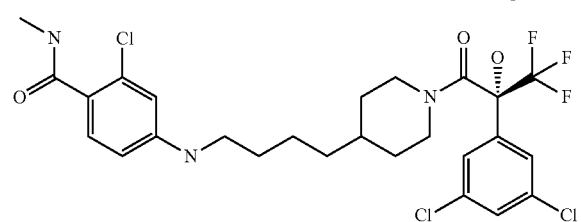
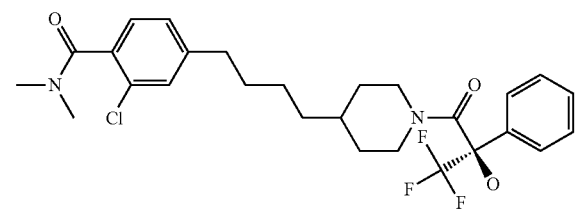
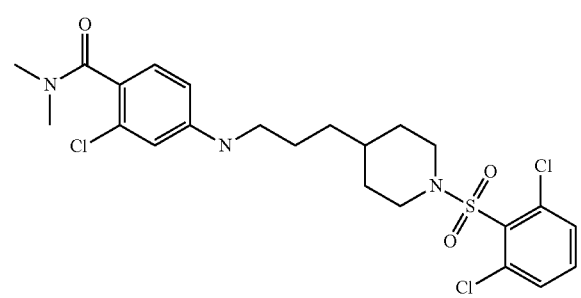
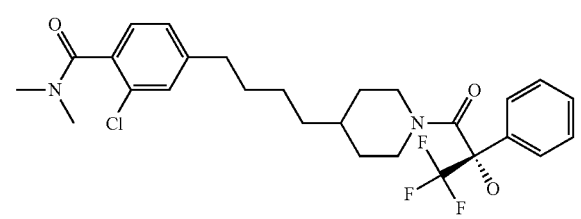
118
-continued
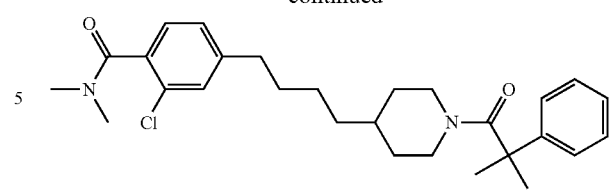
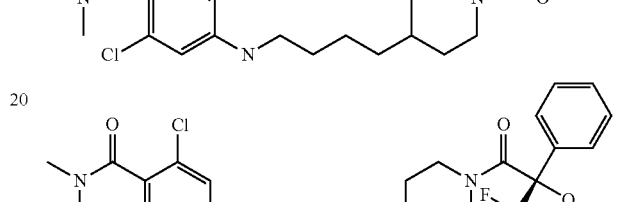
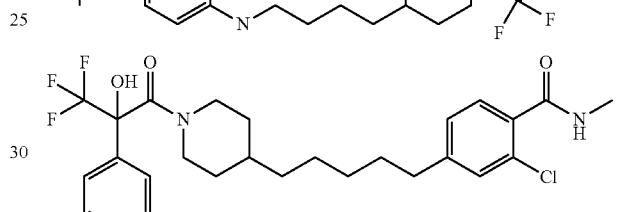
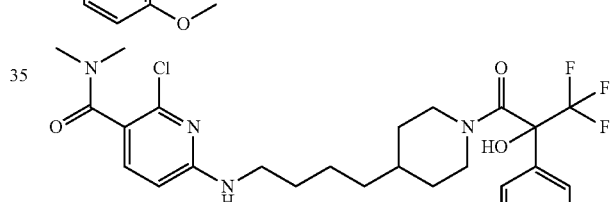
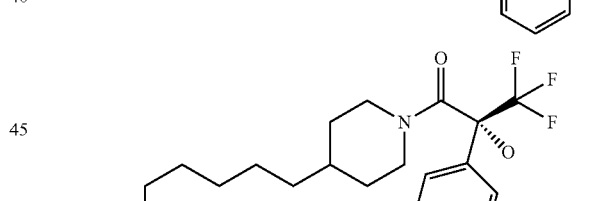
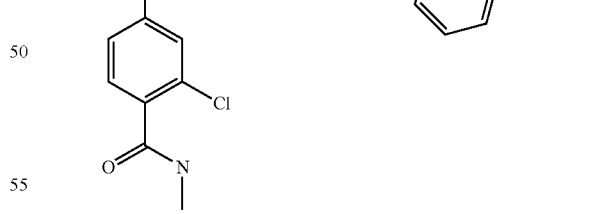
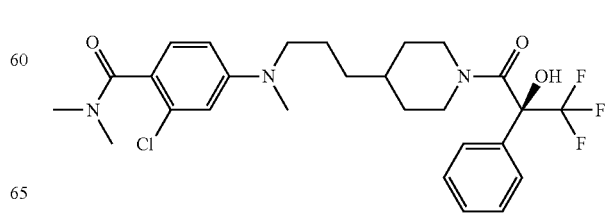

119
-continued
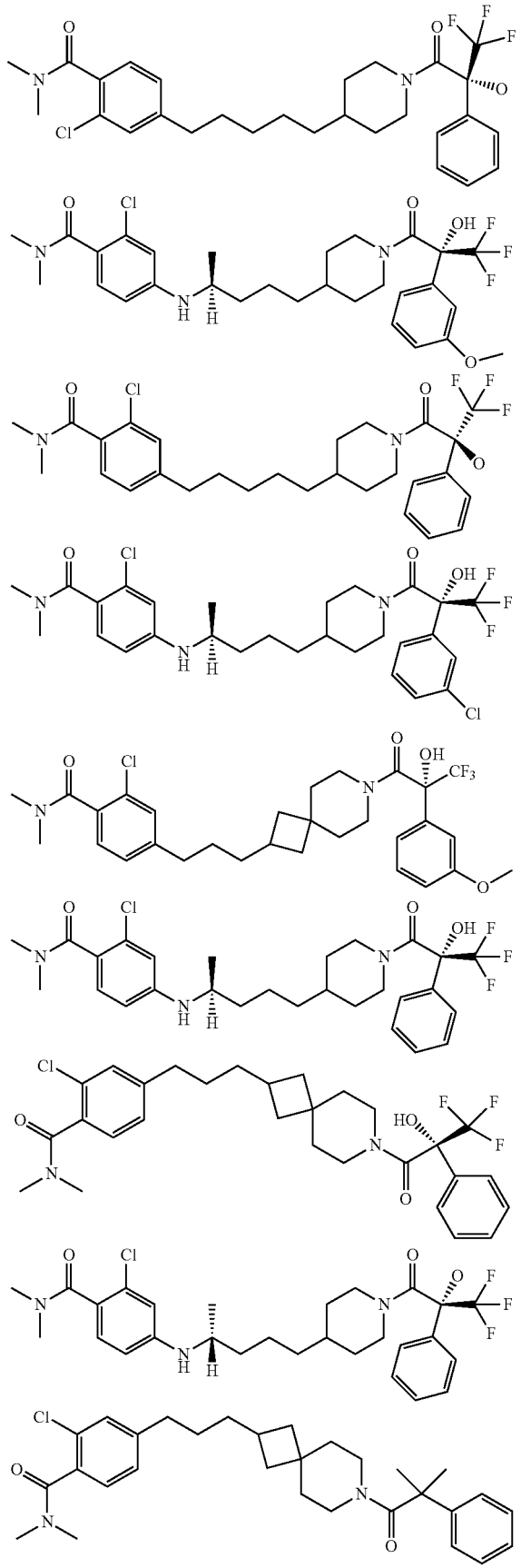
120
-continued
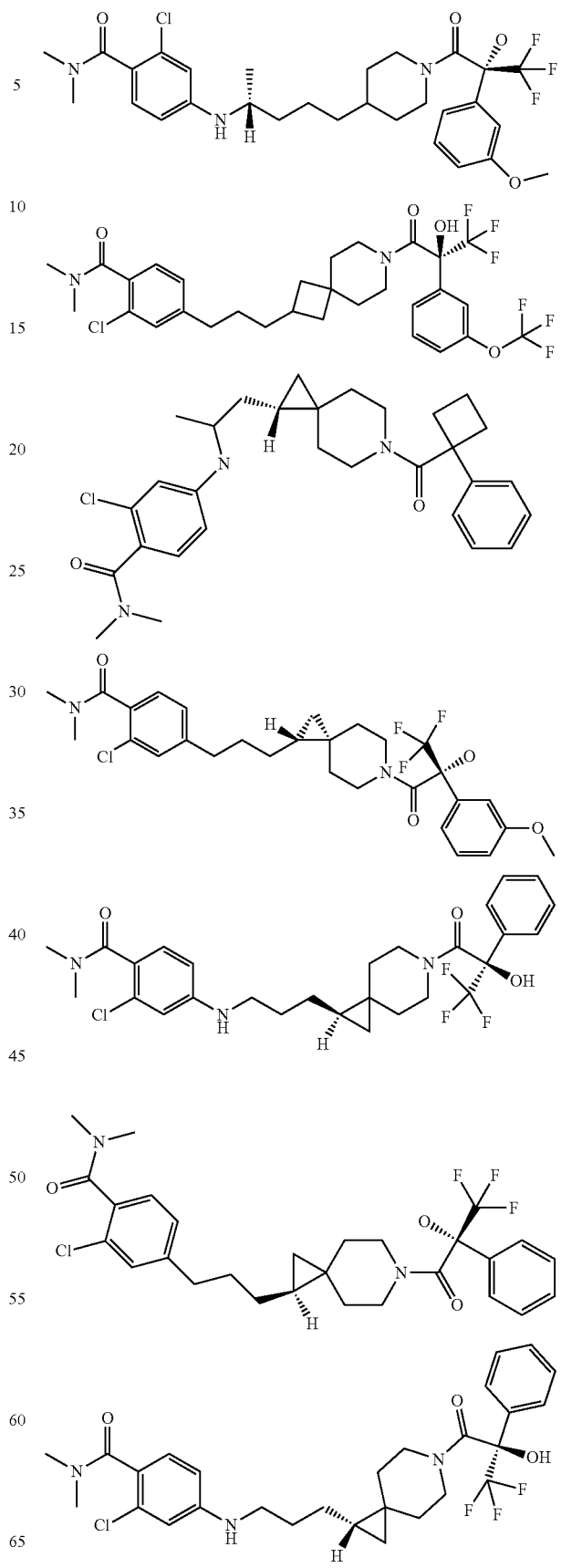

121
-continued
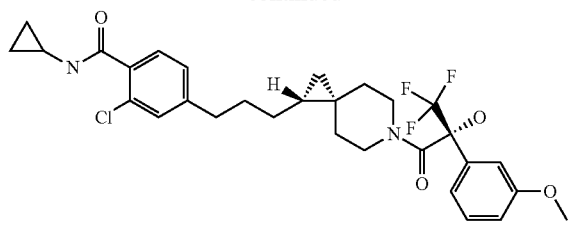
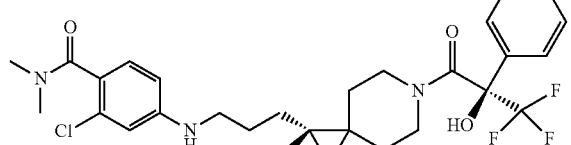
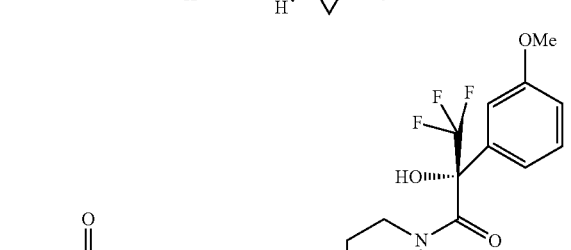
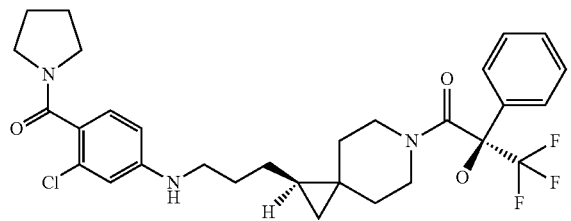
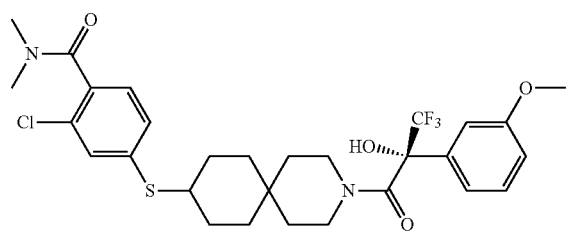
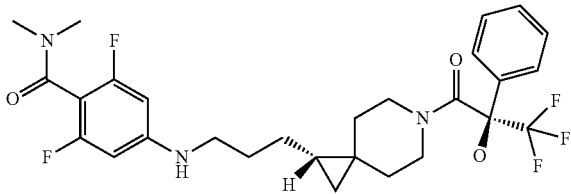
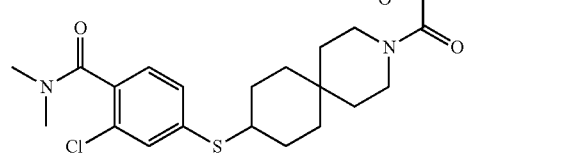
122
-continued
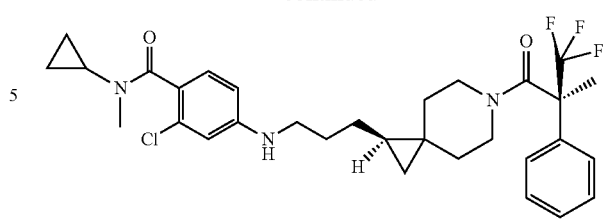
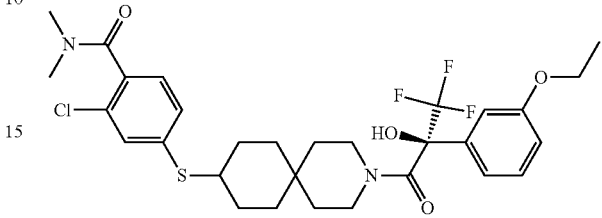
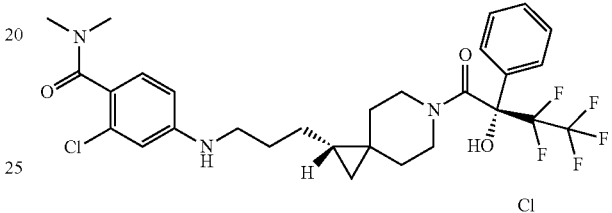
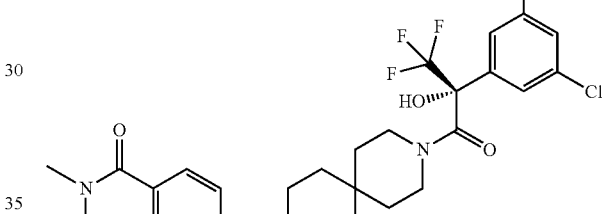
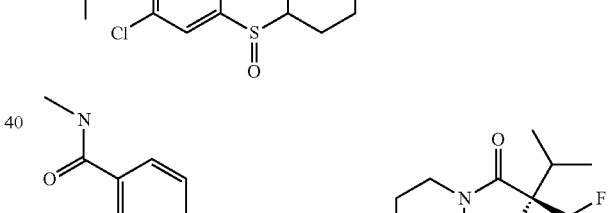
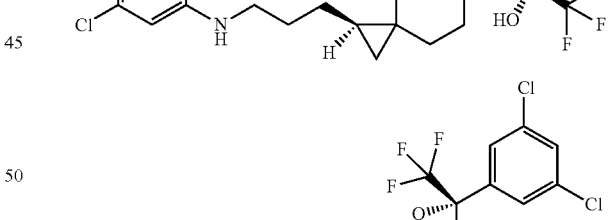
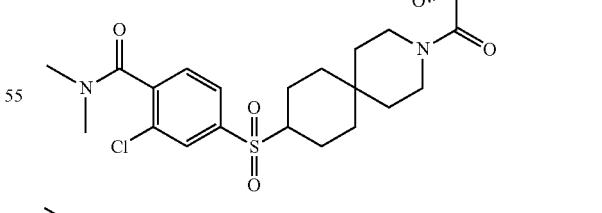
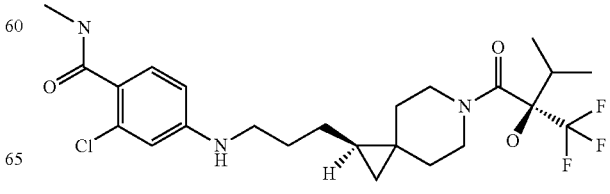

-continued
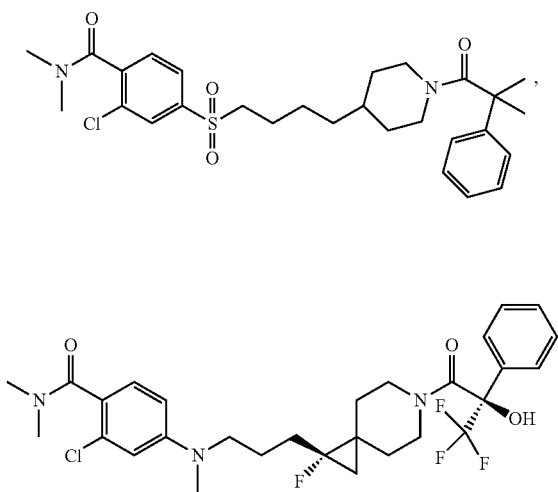
-continued
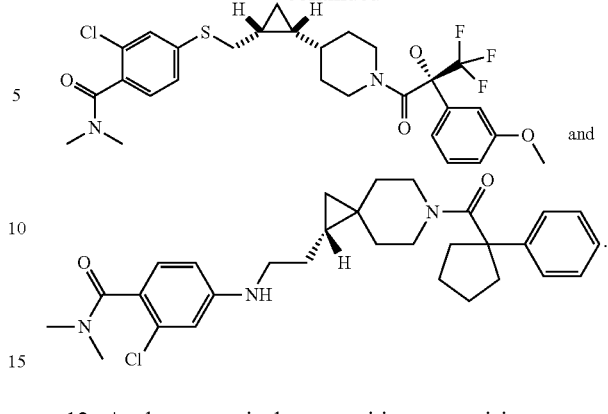
12. A pharmaceutical composition comprising a compound according to claim 1, or a pharmaceutically acceptable salt thereof, and a pharmaceutically acceptable carrier or diluent.
* * * * *

UNITED STATES PATENT AND TRADEMARK OFFICE
CERTIFICATE OF CORRECTION

PATENT NO. : 10,894,775 B2
APPLICATION NO. : 16/341591
DATED : January 19, 2021
INVENTOR(S) : Michael T. Rudd et al.

Page 1 of 1

It is certified that error appears in the above-identified patent and that said Letters Patent is hereby corrected as shown below:

In the Claims

In Column 121, Claim 11: replace second compound with:

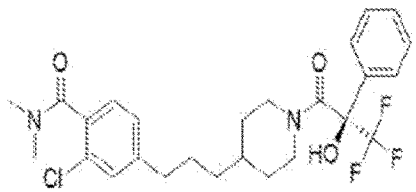

In Column 122, Claim 11: replace First compound with:

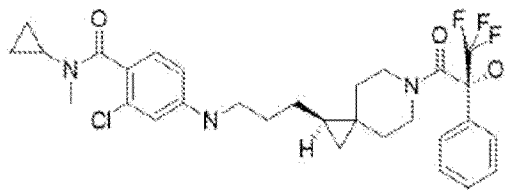

Signed and Sealed this
First Day of June, 2021

Drew Hirshfeld
*Performing the Functions and Duties of the
Under Secretary of Commerce for Intellectual Property and
Director of the United States Patent and Trademark Office*